United States Patent
Borkan et al.

(10) Patent No.: US 11,136,363 B2
(45) Date of Patent: Oct. 5, 2021

(54) COMPOSITIONS AND METHODS FOR DIAGNOSING AND/OR TREATING KIDNEY INJURY

(71) Applicant: Boston Medical Center Corporation, Boston, MA (US)

(72) Inventors: Steven C. Borkan, Medfield, MA (US); Zhiyong Wang, Cambridge, MA (US)

(73) Assignee: Boston Medical Center Corporation, Boston, MA (US)

( * ) Notice: Subject to any disclaimer, the term of this patent is extended or adjusted under 35 U.S.C. 154(b) by 0 days.

(21) Appl. No.: 16/265,413

(22) Filed: Feb. 1, 2019

(65) Prior Publication Data

US 2019/0256567 A1   Aug. 22, 2019

Related U.S. Application Data

(60) Provisional application No. 62/625,536, filed on Feb. 2, 2018, provisional application No. 62/777,514, filed on Dec. 10, 2018.

(51) Int. Cl.

| | |
|---|---|
| *C07K 14/47* | (2006.01) |
| *A61P 9/10* | (2006.01) |
| *A61K 9/00* | (2006.01) |
| *A61P 13/12* | (2006.01) |
| *G01N 33/50* | (2006.01) |
| *G01N 33/543* | (2006.01) |
| *G01N 33/68* | (2006.01) |

(52) U.S. Cl.
CPC ........ *C07K 14/4703* (2013.01); *A61K 9/0019* (2013.01); *A61P 9/10* (2018.01); *A61P 13/12* (2018.01); *C07K 14/47* (2013.01); *G01N 33/5091* (2013.01); *G01N 33/54306* (2013.01); *G01N 33/6875* (2013.01); *C07K 2319/09* (2013.01); *G01N 2440/14* (2013.01); *G01N 2800/347* (2013.01)

(58) Field of Classification Search
None
See application file for complete search history.

(56) References Cited

PUBLICATIONS

Amin et al. "Depletion of nucleophosmin leads to distortion of nucleolar and nuclear structures in HeLa cells" Biochem J 415: 345-351, (2008).
Andreoli "Acute renal failure in the newborn" Semin Perinatol 28: 112-123, (2004).
Ardito et al. "The crucial role of protein phosphorylation in cell signaling and its use as targeted therapy (Review)." Int J Mol Med 40: 271-280, (2017).
Askenazi et al. "3-5 Year longitudinal follow-up of pediatric patients after acute renal failure." Kidney Int 69: 184-189, (2006).
Bacher et al. "Molecular diagnostics in acute leukemias" Clin Chem Lab Med 47: 1333-1341, (2009).
Balusu et al. "Targeting levels or oligomerization of nucleophosmin 1 induces differentiation and loss of survival of human AML cells with mutant NPM1." Blood 118: 3096-3106, (2011).
Banerjee et al. "Asymmetric modulation of protein order-disorder transitions by phosphorylation and partner binding," Angew Chem Int Ed Engl 55: 1675-1679, (2016).
Bleicken et al. "Structural model of active Bax at the membrane." Mol Cell 56: 496-505, (2014).
Bonegio et al. "Role of apoptosis in the pathogenesis of acute renal failure." Curr Opin Nephrol Hypertens 11: 301-308, (2002).
Borkan et al "The role of BCL-2 family members in acute kidney injury" Semin Nephrol 36: 237-250, (2016).
Borkan et al. "Heat stress ameliorates ATP depletion-induced sublethal injury in mouse proximal tubule cells." Am J Physiol 272: F347-F355, (1997).
Box et al. "Nucleophosmin: From structure and function to disease development." BMC Mol Biol 17: 19, (2016).
Brooks et al. "Fragmented mitochondria are sensitized to Bax insertion and activation during apoptosis." Am J Physiol Cell Physiol 300: C447-C455, (2011).
Cha et al."Phosphorylation regulates nucleophosmin targeting to the centrosome during mitosis as detected by cross-reactive phosphorylation-specific MKK1/MKK2 antibodies." Biochem J, 378(Pt 3): 857-65 (2004).
Chou et al. "Increased stability of nucleophosmin/B23 in anti-apoptotic effect of ras during serum deprivation," Mol Pharrnacol, 59(1): 38-45 (2001).
Falini et al. "Altered nucleophosmin transport in acute rnyeloid leukaemia with mutated NPM1: molecular basis and clinical implications." Leukemia, 23(10):1731-43 (2009).
Falini et al., "Cytoplasmic nucleophosmin in acute myelogenous leukemia with a normal karyotype." N Engl J Med, 352 (3): p. 254-66 (2005).
Falini et al., "Immunohistochemistry predicts nucleophosmin (NPM) mutations in acute myeloid leukemia." Blood, 108 (6): p. 1999-2005 (2006).
Ferrara et al. "Clinically useful prognostic factors in acute myeloid leukemia." Crit Rev Oncol Hematol 66: 181-193, (2008).
Frehlick et al. "New insights into the nucleophosmin/ nucleoplasmin family of nuclear chaperones." BioEssays 29: 49-59, (2007).
Gall et al."Conditional knockout of proximal tubule rnitofusin 2 accelerates recoveryand improves survival after renal ischemia" J Am Soc Nephrol26: 1092-1102, (2015).
Galluzzi et al. "Molecular mechanisms of regulated necrosis." Semin Cell Bev Biol 35: 24-32, (2014).

(Continued)

*Primary Examiner* — Christina Bradley
(74) *Attorney, Agent, or Firm* — Nixon Peabody LLP

(57) ABSTRACT

One aspect of the technology relates to methods, assays and kits to identify ischemia and ischemic injury, including kidney injury, and are useful in determining efficacy of cancer treatments. In particular, differential phosphorylation of the nucleophosmin (NPM) polypeptide is an early marker of ischemic injuries such as kidney injury, AKI and ischemic renal cell injury. Another aspect of the technology relates to compositions and methods for the treatment of ischemia and kidney injury, including NPM inhibitory agents, including, but not limited to NPM inhibitory peptides for the treatment of ischemia and kidney injury.

11 Claims, 7 Drawing Sheets
Specification includes a Sequence Listing.

(56) References Cited

PUBLICATIONS

Gardai et al. "Phosphorylation of Bax Ser184 by Akt regulates its activity and apoptosis in neutrophils." J Biol Chem 279: 21085-21095, (2004).
Grisendi et al. "Role of nucleophosmin in embryonic development and tumorigenesis." Nature 437: 147-153, (2005).
Karch et al. "Bax and Bak function as the outer membrane component of the mitochondrial permeability pore in regulating necrotic cell death in mice." eLife 2: e00772, (2013).
Karch et al. "Necroptosis interfaces with MOMP and the MPTP in mediating cell death," PLoS One 10: e0130520, (2015).
Kerr et al. "Nucleophosmin is a novel Bax chaperone that regulates apoptotic cell death." Oncogene 26: 2554-2562, (2007).
Khandelwal et al. "Nucleolar NF-kB/RelA mediates apoptosis by causing cytoplasmic relocalization of nucleophosmin." Cell Death Differ 18: 1889-1903, (2011).
Knudson et al. "Alfred Knudson and his two-hit hypothesis. (Interview by Ezzie Hutchinson)" Lancet Oncol 2: 642-645, (2001).
Koike et al. "Recruitment of phosphorylated NPM1 to sites of DNA damage through RNF8-dependent ubiquitin conjugates." Cancer Res 70: 6746-6756, (2010).
Li et al.: Heatstress prevents mitochondrial injury in ATP-depleted renal epithelialcells. Am J Physiol Cell Physiol 283: C917-C926, (2002).
Lieberthal et al. "Graded ATP depletion can cause necrosis or apoptosis of cultured mouse proximal tubular cells." Am J Physiol 274: F315-F327, (1998).
Lim et al. "Nucleophosmin and human cancer" Cancer Detect Prev 30: 481-490, (2006).
Lindenboim et al. "Regulation of stress-induced nuclear protein redistribution: A new function of Bax and Bak uncoupled from Bcl-x(L)." Cell Death Differ 17: 346-359, (2010).
Linkermann et al. "Rip1 (receptor-interacting protein kinase 1) mediates necroptosis and contributes to renal ischemia/reperfusion injury." Kidney Int 81: 751-761, (2012).
Linkermann et al. "Synchronized renal tubular cell death involves ferroptosis". Proc Natl Acad Sci U S A 111: 16836-16841, (2014).
Mammen et al. "Long-term risk of CKD in children surviving episodes of acute kidney injury in the intensive care unit: A prospective cohort study." Am J Kidney Dis 59: 523-530, (2012).
Naganska et al. "Morphological evidence of the continuum between necrosis and apoptosis in model of anoxia in vitro." J Neurochem 85: 24-24, (2003).
Okuwaki, "The structure and functions of NPM1/Nucleophsmin/B23, a multifunctional nucleolar acidic protein." J Biochem, 143(4): p. 441-8 (2006).
Parikh et al. "Mitochondrial function and disturbances in the septic kidney" Semin Nephrol 35: 108-119, (2015).
Ql et al. "NSC348884, a nucleophosmin inhibitor disrupts oligomer formation and induces apoptosis in human cancer cells." Oncogene 27: 4210-4220, (2008).
Rabb et al. "Acute Dialysis Quality Initiative Consensus XIII Work Group: Inflammation in AKI: Current understanding, key questions, and knowledge gaps." J Am Soc Nephrol 27: 371-379, (2016).
Sutherland et al. "AKI in hospitalized children: Epidemiology and clinical associations in a national cohort." Clin J Am Soc Nephrol 8: 1661-1669, (2013).
Thompson et al. Characterisation of the Bax-nucleophosmin interaction: The importance of the Bax C-terminus, Apoptosis 13: 394-403, (2008).
Tischner et al. "Necrosis-like death can engage multiple pro-apoptotic Bcl-2 protein family members." Apoptosis 17: 1197-1209, (2012).
Van Beek et al. "Acute kidney injury defined according to the 'Risk,' Injury, 'Failure,' 'Loss,' and 'End-stage' (RIFLE) criteria after repair for a ruptured abdominal aortic aneurysm." J Vasc Surg 60: 1159-1167.e1, (2014).
Wang et al. "Acute kidney injury and mortality in hospitalized patients" Am J Nephrol 35: 349-355, (2012).
Wei et al. "Bax and Bak have critical roles in ischemic acute kidney injury in global and proximal tubulespecific knockout mouse models." Kidney Int 84: 138-148, (2013).
Whelan et al. "Bax regulates primary necrosis through mitochondrial dynamics." Proc Natl Acad Sci U S A 109: 6566-6571, (2012).
Yang et al, "Renoprotective approaches and strategies in acute kidney injury" Pharmacol Ther 163: 58-73, (2016).
Zeiss "The apoptosis-necrosis continuum: Insights from genetically altered mice." Vet Pathol 40: 481-495, (2003).
Yamamoto et al."Hypoxia-induced renal epithelial cell death through caspase-dependent pathway: Role of Bcl-2, Bcl-xL and Bax in tubular injury." Int J Mol Med 14: 633-640, (2004).
Phosphonet "NPM1" (Aug. 1, 2017)—[Retrieved on May 7, 2019 from the internet http://www.phosphonet.ca/default.aspx?search=P06748].
Wang et al. "Nucleophosmin a critical Bax cofactor in ischemia-induced cell death." Molecular Cell Biology, 33(10): 1916-1924 (2013).
Zhao et al. "Cell cycle-dependent phosphorylation of nucleophosmin and its potential regulation by peptidyl-prolyl cis/trans isomerase." Journal of Molecular Biochemistry 4: 95-103 (2015).

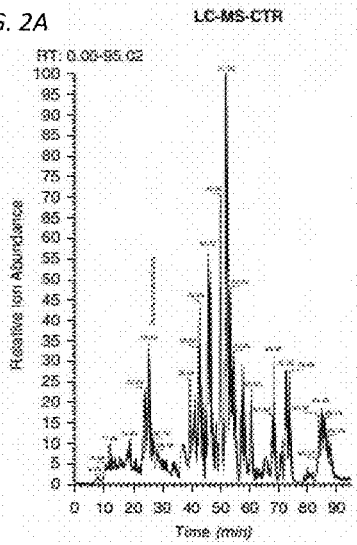
FIG. 2A
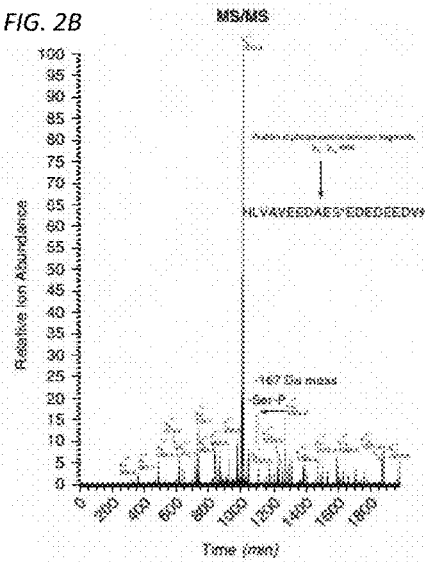
FIG. 2B
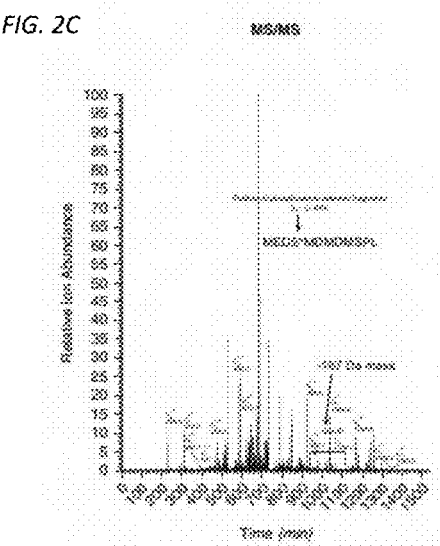
FIG. 2C
FIG. 2D

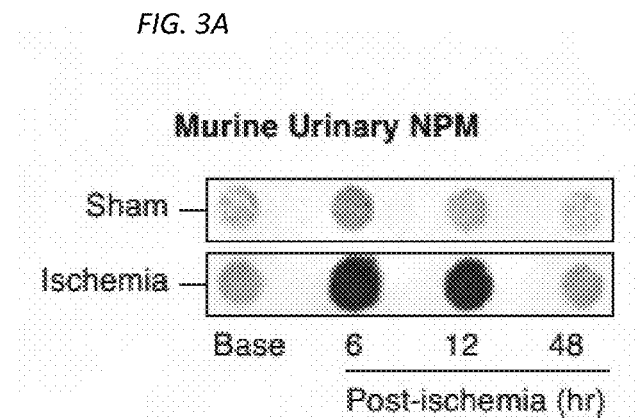
FIG. 3A
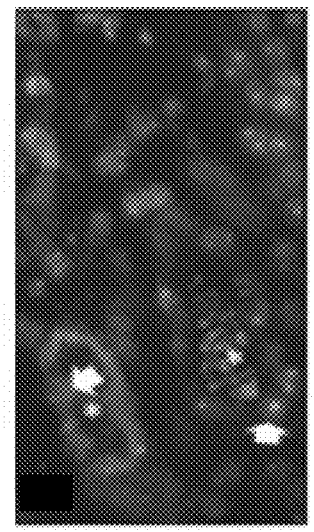
FIG. 3B
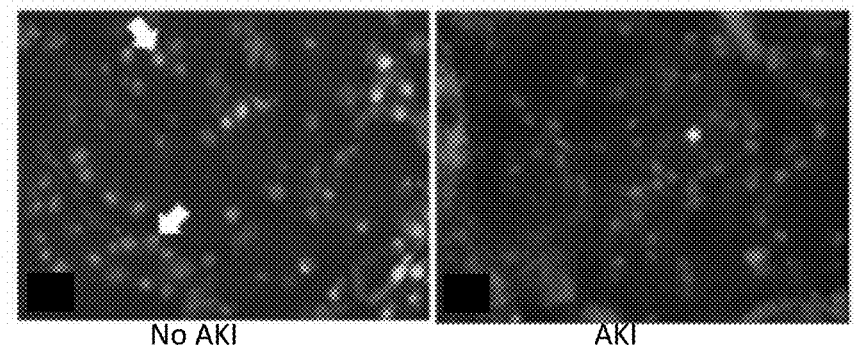
FIG. 3C
No AKI | AKI
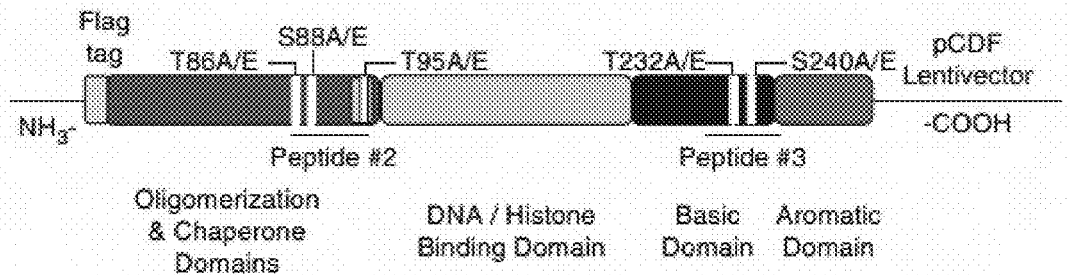
FIG. 4A
FIG. 4B

| | Therapeutic Peptide Sequences* | |
|---|---|---|
| Bax | TVTIFVAGVLTASLTIWKKMG | (SEQ ID NO: 1) |
| #2 | TLKMSVQPTVSLGGFEITPPVVLRLK | (SEQ ID NO: 2) |
| #3 | ESFKKQEKTPKTPKGPSSVEDIKAK | (SEQ ID NO: 3) |

* All N-terminal renal targeting peptides contain: Ac-KKKRKV-(βA)

SEQUENCE LISTING

<160> NUMBER OF SEQ ID NOS: 17

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Thr Val Thr Ile Phe Val Ala Gly Val Leu Thr Ala Ser Leu Thr Ile
1               5                   10                  15

Trp Lys Lys Met Gly
            20

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Leu Lys Met Ser Val Gln Pro Thr Val Ser Leu Gly Gly Phe Glu
1               5                   10                  15

Ile Thr Pro Pro Val Val Leu Arg Leu Lys
            20                  25

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ser Phe Lys Lys Gln Glu Lys Thr Pro Lys Thr Pro Lys Gly Pro
1               5                   10                  15

Ser Ser Val Glu Asp Ile Lys Ala Lys
            20                  25

<210> SEQ ID NO 4
<211> LENGTH: 294
<212> TYPE: PRT
<213> ORGANISM: Homo sapiens

<400> SEQUENCE: 4

Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Glu Glu Glu Asp Val Lys Leu Leu Ser Ile Ser Gly Lys Arg Ser Ala
    130                 135                 140

Pro Gly Gly Gly Ser Lys Val Pro Gln Lys Lys Val Lys Leu Ala Ala
145                 150                 155                 160
```

```
Asp Glu Asp Asp Asp Asp Asp Glu Glu Asp Asp Glu Asp Asp
            165                 170                 175
Asp Asp Asp Asp Phe Asp Glu Glu Ala Glu Glu Lys Ala Pro Val
        180                 185                 190
Lys Lys Ser Ile Arg Asp Thr Pro Ala Lys Asn Ala Gln Lys Ser Asn
    195                 200                 205
Gln Asn Gly Lys Asp Ser Lys Pro Ser Ser Thr Pro Arg Ser Lys Gly
    210                 215                 220
Gln Glu Ser Phe Lys Lys Gln Glu Lys Thr Pro Lys Thr Pro Lys Gly
225                 230                 235                 240
Pro Ser Ser Val Glu Asp Ile Lys Ala Lys Met Gln Ala Ser Ile Glu
                245                 250                 255
Lys Gly Gly Ser Leu Pro Lys Val Glu Ala Lys Phe Ile Asn Tyr Val
                260                 265                 270
Lys Asn Cys Phe Arg Met Thr Asp Gln Glu Ala Ile Gln Asp Leu Trp
            275                 280                 285
Gln Trp Arg Lys Ser Leu
    290

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine

<400> SEQUENCE: 5

Lys Lys Lys Arg Lys Val Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Beta-alanine

<400> SEQUENCE: 6

Pro Lys Lys Lys Arg Lys Val Ala
1               5

<210> SEQ ID NO 7
<211> LENGTH: 1449
<212> TYPE: DNA
<213> ORGANISM: Homo sapiens

<400> SEQUENCE: 7
agaaaggagt gggggtttgaaa agcgcttgcg caggacggct acggtacggg ggtgggaggg    60
cttcggagca cgcgcgcgga ggcgggactt gggaagcgct cgcgagatct tcagggtcta   120
tatataagcg cggggagcct gcgtcctttc cctggtgtga ttccgtcctg cgcggttgtt   180
ctctggagca gcgttctttt atctccgtcc gccttctctc ctacctaagt gcgtgccgcc   240
```

```
acccgatgga agattcgatg gacatggaca tgagccccct gaggccccag aactatcttt    300
tcggttgtga actaaaggcc gacaaagatt atcactttaa ggtggataat gatgaaaatg    360
agcaccagtt atctttaaga acggtcagtt taggggctgg tgcaaaggat gagttgcaca    420
ttgttgaagc agaggcaatg aattacgaag gcagtccaat taaagtaaca ctggcaactt    480
tgaaaatgtc tgtacagcca acggtttccc ttggggcctt tgaaataaca ccaccagtgg    540
tcttaaggtt gaagtgtggt tcagggccag tgcatattag tggacagcac ttagtagctg    600
tggaggaaga tgcagagtca gaagatgaag aggaggagga tgtgaaactc ttaagtatat    660
ctggaaagcg gtctgcccct ggaggtggta gcaaggttcc acagaaaaaa gtaaaacttg    720
ctgctgatga agatgatgac gatgatgatg aagaggatga tgatgaagat gatgatgatg    780
atgattttga tgatgaggaa gctgaagaaa agcgccagt gaagaaatct atacgagata    840
ctccagccaa aaatgcacaa aagtcaaatc agaatggaaa agactcaaaa ccatcatcaa    900
caccaagatc aaaaggacaa gaatccttca agaaacagga aaaaactcct aaaacaccaa    960
aaggacctag ttctgtagaa gacattaaag caaaaatgca agcaagtata gaaaaaggtg   1020
gttctcttcc caaagtggaa gccaaattca tcaattatgt gaagaattgc ttccggatga   1080
ctgaccaaga ggctattcaa gatctctggc agtggaggaa gtctctttaa gaaaatagtt   1140
taaacaattt gttaaaaaat tttccgtctt atttcatttc tgtaacagtt gatatctggc   1200 tgtcctttt ataatgcaga gtgagaactt tccctaccgt gtttgataaa tgttgtccag   1260
gttctattgc caagaatgtg ttgtccaaaa tgcctgttta gtttttaaag atggaactcc   1320 acccttgct tggttttaag tatgtatgga atgttatgat aggacatagt agtagcggtg   1380
gtcagacatg gaaatggtgg ggagacaaaa atatacatgt gaaataaaac tcagtatttt   1440
aataaagta                                                            1449
```

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine

<400> SEQUENCE: 8

Lys Lys Lys Arg Lys Val Ala Thr Val Thr Ile Phe Val Ala Gly Val
1               5                   10                  15

Leu Thr Ala Ser Leu Thr Ile Trp Lys Lys Met Gly
            20                  25

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Beta-alanine

```
<400> SEQUENCE: 9

Pro Lys Lys Lys Arg Lys Val Ala Thr Leu Lys Met Ser Val Gln Pro
1               5                   10                  15

Thr Val Ser Leu Gly Gly Phe Glu Ile Thr Pro Pro Val Val Leu Arg
            20                  25                  30

Leu Lys

<210> SEQ ID NO 10
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Beta-alanine

<400> SEQUENCE: 10

Pro Lys Lys Lys Arg Lys Val Ala Glu Ser Phe Lys Lys Gln Glu Lys
1               5                   10                  15

Thr Pro Lys Thr Pro Lys Gly Pro Ser Ser Val Glu Asp Ile Lys Ala
            20                  25                  30

Lys

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: phospho-Ser

<400> SEQUENCE: 11

His Leu Val Ala Val Glu Glu Asp Ala Glu Ser Glu Asp Glu Asp Glu
1               5                   10                  15

Glu Asp Val

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: phospho-Ser

<400> SEQUENCE: 12

Met Glu Asp Ser Met Asp Met Asp Met Ser Pro Leu
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Leu Lys Met Ser Val Gln Pro Thr Val Ser Leu Gly Gly Phe Glu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Ser Val Gln Pro Thr Val Ser Leu Gly Gly Phe Glu Ile Thr
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Leu Gly Gly Phe Glu Ile Thr Pro Pro Val Val Leu Arg Leu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Phe Lys Lys Gln Glu Lys Thr Pro Lys Thr Pro Lys Gly Pro
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Lys Thr Pro Lys Gly Pro Ser Ser Val Glu Asp Ile Lys Ala
1               5                   10                  15
```

COMPOSITIONS AND METHODS FOR DIAGNOSING AND/OR TREATING KIDNEY INJURY

CROSS REFERENCE TO RELATED APPLICATIONS

This application claims benefit under 35 U.S.C. § 119(e) of U.S. Provisional Application 62/625,536 filed on Feb. 2, 2018 and Provisional Application 62/777,514, filed on Dec. 10, 2018, the contents of each are incorporated herein by reference in their entireties.

GOVERNMENT SUPPORT

This invention was made with Government Support under Contract No. NIH DK-053387 awarded by the National Institutes of Health. The Government has certain rights in the invention.

SEQUENCE LISTING

The instant application contains a Sequence Listing which has been filed electronically in ASCII format. Said ASCII copy, created on Mar. 14, 2019, is named 701586-091560-WOPT_SL.txt and is 10,092 bytes in size.

TECHNICAL FIELD

The present disclosure described herein relates to compositions and methods for the treatment of ischemia and kidney injury. In particular, differential phosphorylation of the nucleophosmin (NPM) polypeptide is an early marker of ischemic injuries such as kidney injury, AKI and ischemic renal cell injury. Nucleophosmin inhibitory peptides can be used for the treatment of such ischemia and kidney injury.

BACKGROUND OF THE INVENTION

Ischemia/reperfusion injury is a leading cause of human AKI.1-3 AKI occurs in 7%-10% of hospitalized patients at average risk for renal injury 4 and between 23% and 74% of high-risk patients.5,6 Even a modest increase in serum creatinine of >0.5 mg/dl increases the length of stay and hospital cost as well as morbidity and mortality.4 In fact, mortality has been reported to be as high as 80% when the serum creatinine acutely rises by >2 mg/d1.4 In children and adults, a single AKI episode risks progressive kidney injury resulting in ESRD.7,8 Less than 60% of children survive >3-5 years after a single AKI episode.9 Surviving children have a 60% chance of developing high BP, proteinuria, and/or CKD that ultimately requires dialysis or kidney transplantation.9

This is partly due to the facts that diagnostic tests of AKI and organ dysfunction are insensitive and that ischemic renal injury lacks effective treatment.10 Tissue ischemia/reperfusion causes proximal tubule epithelial cell (PTEC) injury, a major contributor to organ failure.1,3,11 Experimental evidence implicates Bax, a quintessential BCL2 proapoptotic protein, as an important cause of regulated PTEC death during hypoxic or ischemic stress and contributor to AKI.11-15

As such, ischemic AKI lacks a urinary marker for early diagnosis and an effective therapy. Accordingly, there is a need for more effective and accurate biomarkers for kidney injury and AKI, as well as effective therapeutics for the treatment of kidney injury.

BRIEF DESCRIPTION OF THE INVENTION

The technology described herein relates to methods, compositions and kits for the diagnosis and treatment of kidney injury and acute kidney injury (AKI).

Acute ischemic injuries, such as acute kidney injury (AKI) is associated with high morbidity and mortality. The lack of sensitive and specific injury biomarkers has greatly impeded the development of therapeutic strategies to improve outcomes of ischemic injuries, e.g., AKI. The diagnostic approach to AKI has stagnated and relies upon the biomarkers, such as, BUN, creatinine, KIM-1 and urine output, however, such biomarkers are inadequate to diagnose AKI as they do not directly reflect cell injury but rather delayed functional consequences of the injury. This has greatly impeded therapeutic innovation.

In particular, the inventors have discovered that the nucleophosmin (NPM) polypeptide, undergoes 5 different phosphorylation events during ischemia and hypoxic stress, and the detection of specific phosphorylation events of NPM in a biological sample obtained from a subject can be used to identify a subject with ischemic injury, such as kidney injury, including but not limited to, acute kidney injury (AKI). Additionally, agents which inhibit the function of the NPM polypeptide, including inhibiting the association of the stress-induced phosphorylation changes of NPM, or its subsequent association with Bax, are effective treatments for ischemia and kidney injury, including AKI.

The biologic behavior and toxicity of NPM was assessed using phospho-NPM mutant proteins that either mimic stress-induced or normal NPM phosphorylation. NPM Peptides were shown to interfere with NPM function and demonstrate that inhibiting NPM function, in particular, inhibiting NPM from complexing with Bax, can be used to treat kidney injury and AKI even after injury has occurred. Moreover, the inventors discovered that within hours of stress, virtually identical phosphorylation changes were detected, for example, at distinct serine/threonine sites in NPM harvested from primary renal cells in vitro, and from kidney tissue and urine in vivo. A phosphomimic NPM protein that replicated phosphorylation under stress localized to the cytosol, formed monomers that interacted with Bax, a cell death protein, and coaccumulated with Bax in isolated mitochondria, and significantly increased cell death after stress. In contrast, wild-type NPM or a phosphomimic NPM with a normal phosphorylation configuration did not. Herein, the inventors demonstrate, with three exemplary renal targeted peptides referred to herein as "NPM peptides", interfere with NPM at distinct functional sites and significantly protected cells, e.g., renal cells against cell death, and significantly, demonstrate in vivo evidence that a single dose of one peptide administered several hours after ischemia that would be lethal in untreated mice significantly reduced AKI severity and improved survival. As such, the inventors demonstrate that phosphorylation and/or unphosphorylation at specific sites on the NPM polypeptide serve as a potential early marker of ischemic stress, including kidney injury and ischemic AKI that links early diagnosis with effective therapeutic interventions.

In particular, the present invention is based on, in part, the discovery that phosphorylated NPM is both a marker of acute renal cell injury and an effective target for a range of inhibitors, herein referred to NPM inhibitory agents, such as, e.g., NPM inhibitory peptide therapeutics, siRNA and neutralizaing antibodies designed to inhibit the Bax-NPM complex, or its formation, and ameliorate NPM-Bax-mediated tissue injury. The inventors have discovered that virtually identical stress-induced, site-specific phosphorylation changes (i.e., phosphorylation and dephosphorylation events) render NPM toxic in isolated murine and human renal cells in vitro, as well as fresh kidney tissue and urine in vivo. Furthermore, inhibiting the NPM-Bax-mediated renal cell death and AKI using, for example, NPM inhibitor peptides can be used to treat or prevent kidney injury and/or AKI. In particular, the inventors have discovered that detection of the phosphorylation status of NPM, for example, differential NPM phosphorylation, can be coupled with NPM peptides as disclosed herein, and can be an effective AKI therapeutic treatment, even after the insult has occurred.

In particular, the inventors have discovered stress-induced differential phosphorylation of nucleophosmin (NPM), a chaperone of the apoptotic factor Bax, finding a virtually identical NPM stress-induced phosphorylation pattern in mouse and human primary renal cells, fresh kidney tissue, and urine within hours of injury. An NPM mimetic protein that replicates this stress-induced differential phosphorylation (but not a mimetic with a normal phosphorylation state) is toxic to renal cells. The inventors have demonstrated that administering, for example a targeted NPM inhibitor peptides designed to reduce NPM toxicity, even hours after a typically lethal ischemic insult, improves cell and animal survival. Accordingly, the inventors have demonstrated that stress-induced NPM phosphorylation is a significant contributor to renal cell death in human AKI and identification of specific ischemic-induced NPM phosphorylation changes can be used in early diagnosis and management of ischemic injuries, e.g., ischemic kidney injuries. Moreover, administration of peptides or agents that inhibit the stress-induced NPM phosphorylation can be used to treat, or prevent death or injury to renal cells in subjects with AKI, or after ischemic insult (including hypoxia and the like).

Accordingly, one aspect of the technology described herein relates to a diagnostic assay, method and composition to assess if a subject has AKI, wherein the method comprises assessing the phosphorylation status of the NPM polypeptide, and detecting a change of at least one of the phosphorylation sites as follows: T86, S88, T95, T234 or S242. In particular, under normal conditions (e.g., non-stress conditions) T86, S88, T95 of the NPM polypeptide are unphosphorylated, and become phosphorylated under stressful conditions to become phospho-T86, phospho-S88, phospho-T95. In contrast, under normal conditions (e.g., non-stress conditions) T234 and S242 of the NPM polypeptide are phosphorylated, and become dephosphorylated under stressful conditions. That is, under normal conditions, the phosphorylation state of the NPM polypeptide is T86, S88, T95, phospho-T234, phospho-S242, and under stressful conditions, or after AKI, the phosphorylation state of the NPM polypeptide is phospho-T86, phospho-S88, phospho-T95, T234, S242.

Accordingly, in some embodiments, an assay can comprise a method to detect at least one or more of: phospho-T86, phospho-S88, phospho-T95, unphosporylated-T234 and unphosporylated-S242 of a NPM polypeptide in a biological sample obtained from a subject, wherein detection of at least one, or at least 2, or at least 3 or at least 4 of the above phosphorylation states of NPM polypeptide identifies a subject with kidney injury or AKI. Detection of the phosphorylation states can be by any means, e.g., mass spectrometry, antibodies or antibody fragments, including but not limited to, pan-specific phospho-Ser (anti-pSer) or phospho-Thr (anti-pThr) antibodies, as well as phospho-specific antibodies, e.g., anti-phospho-T86, anti-phospho-S88, anti-phospho-T95, anti-phospho-T234 and anti-phospho-S242 antibodies, or antibody fragments or antigen binding fragments thereof. In one embodiment, one looks for a change in at least one normally unphosphorylated amino acid and one normally phosphorylated amino acid.

Exemplary biological samples include, but are not limited to, a kidney biopsy sample, serum, blood, plasma and urine. Additionally, the inventors have also discovered that interruption of the stress-induced NPM phosphorylation events, e.g., using one of three different blocking peptides, can decrease cell death in the kidney due to metabolic stress (including ischemic stress and hypoxic stress), and can be used as treatment, including therapeutic treatment to treat a subject with AKI, or alternatively, as a prophylactic treatment to prevent the subject developing AKI.

Another aspect of the technology described herein relates to a method to treat a subject any of: acute kidney injury (AKI) or ischemia, comprising administering a subject a composition comprising at least one peptide selected from the group consisting of: TVTIFVAGVLTASLTIWKKMG (SEQ ID NO: 1); TLKMSVQPTVSLGGFEITPPVVLRLK (peptide #2) (SEQ ID NO: 2) and ESFKKQEKTPKTPKGPSSVEDIKAK (peptide #3) (SEQ ID NO: 3), or a peptide with at least 85% or 90% or 95% sequence identity to any of SEQ ID NO: 1-3. In some embodiments, the peptides of SEQ ID NO: 1-3 are conjugated or attached to renal targeting moieties or peptides, including renal targeting nuclear localization sequences (NLS) and/or Cell penetrating peptides (referred to as "CPP") as described herein, so the peptides target the kidney.

One aspect described herein is directed to a method of treating kidney injury or acute kidney injury (AKI) in a subject in need thereof, the method comprising (a) administering a treatment for kidney injury or AKI to a subject who has first been determined to have in a biological sample obtained from the subject, at least one of:
i. phosphorylation of at least one of serine or threonine residue selected from: T86, S88, or T95 of the nucleophosmin (NPM) polypeptide; and
ii. absence of phosphorylation of at least one of at least one serine or threonine residue selected from T234 or S242 on a nucleophosmin (NPM) polypeptide, wherein the treatment for kidney injury or AKI is an inhibitor of the formation of a Bax-NPM complex or is an inhibitor of a NPM polypeptide, wherein the NPM polypeptide comprises at the phosphorylation of at least one of serine or threonine residue selected from: T86, S88, or T95, and absence of phosphorylation of at least one of at least one serine or threonine residue selected from T234 or S242.

In some embodiments, an inhibitor of the NPM polypeptide is a NPM peptide, siRNA or antibody, and can in some embodiments, be an NPM inhibitor peptide. Exemplary NPM inhibitor peptides can be selected from a peptide comprising the amino acid sequences of: TVTIFVAGVL-TASLTIWKKMG (SEQ ID NO: 1); TLKMSVQPTVSLGGFEITPPVVLRLK (SEQ ID NO: 2) and ESFKKQEKTPKTPKGPSSVEDIKAK (SEQ ID NO: 3), or peptide with at least 85% sequence identity to any of SEQ ID NO: 1-3.

One aspect described herein is directed a method of treating a subject with kidney injury, ischemia, or a subject after an ischemic injury, the method comprising administering to a subject a composition comprising at least one peptide comprising the amino acid sequences of: TVTIFVAGVLTASLTIWKKMG (SEQ ID NO: 1);

TLKMSVQPTVSLGGFEITPPVVLRLK (SEQ ID NO: 2) and ESFKKQEKTPKTPKGPSSVEDIKAK (SEQ ID NO: 3), or peptide with at least 85% sequence identity to any of SEQ ID NO: 1-3.

Another aspect described herein is directed a method for inhibiting the formation of a nucleosphosmin (NMP)-Bax complex, the method comprising contacting a cell with at least one peptide from any peptide comprising the amino acid sequences of: TVTIFVAGVLTASLTIWKKMG (SEQ ID NO: 1); TLKMSVQPTVSLGGFEITPPVVLRLK (SEQ ID NO: 2) and ESFKKQEKTPKTPKGPSSVEDIKAK (SEQ ID NO: 3), or peptide with at least 85% or 90% or 95% sequence identity to any of SEQ ID NO: 1-3.

Another aspect described herein is directed a method for inhibiting stress induced cell death, the method comprising the method comprising contacting a cell with at least one peptide from any peptide comprising the amino acid sequences of: TVTIFVAGVLTASLTIWKKMG (SEQ ID NO: 1); TLKMSVQPTVSLGGFEITPPVVLRLK (SEQ ID NO: 2) and ESFKKQEKTPKTPKGPSSVEDIKAK (SEQ ID NO: 3), or peptide with at least 85% sequence identity to any of SEQ ID NO: 1-3.

Another aspect described herein is directed a method to inhibit nucleosphosmin (NMP) forming a complex with Bax, the method comprising contacting a cell with an agent which inhibits the phosphorylation of at least one of: T86, S88, T95 of the NMP polypeptide, and/or inhibits the dephsporylation of at least one of: T232 or S240 of the NMP polypeptide, thereby inhibiting the formation of a NMP-Bax complex.

Another aspect relates to method for inhibiting stress induced cell death, the method comprising contacting a cell with an agent which inhibits the phosphorylation of at least one of: T86, S88, T95 of the NMP polypeptide, and/or inhibits the dephsporylation of at least one of: T232 or S240 of the NMP polypeptide, thereby inhibiting the formation of a NMP-Bax complex.

In all aspects herein, the methods can be used in the treatment of a subject with kidney injury, ischemia, or a subject after an ischemic injury.

In all aspects herein, an NPM inhibitor agent is at least one peptide from any peptide comprising the amino acid sequences of: TVTIFVAGVLTASLTIWKKMG (SEQ ID NO: 1); TLKMSVQPTVSLGGFEITPPVVLRLK (SEQ ID NO: 2) and ESFKKQEKTPKTPKGPSSVEDIKAK (SEQ ID NO: 3), or peptide with at least 85% sequence identity to any of SEQ ID NO: 1-3. In some embodiments, a peptide is fused to a renal targeting nuclear localization sequence (NSL). In some embodiments, a peptide is administered within 48 hours of an ischemic event or ischemic injury. The method of claim 13, wherein the peptide is administered within 12 hours of an ischemic event.

In all aspects herein, a kidney injury is selected from the group consisting of: injury to the proximal tubule of the kidney; acute kidney injury (AKI); chronic kidney disease (CKD); early kidney injury which will progress into chronic kidney disease (CKD).

In all aspects herein, ischemia is due to ischemic stress, hypoxic stress or metabolic stress, e.g., wherein the subject has ischemia in any tissue, such as, e.g., ischemia to any one or more of kidney, brain, muscle, liver, intestines or heart.

Another aspect described herein relates to diagnostic methods. In one embodiment, a method for treating kidney injury or acute kidney injury (AKI) in a subject is described, the method comprising: (a) first detecting, in a biological sample obtained from the subject, at least one of:

i. the presence of phosphorylation of at least one of serine or threonine residue selected from: T86, S88, or T95 of the nucleophosmin (NPM) polypeptide; or ii. the absence of phosphorylation of at least one of at least one serine or threonine residue selected from T234 or S242 on a nucleophosmin (NPM) polypeptide; and and (b) administering to the subject a pharmaceutical composition comprising at least one peptide from any peptide comprising the amino acid sequences of: TVTIFVAGVLTASLTIWKKMG (SEQ ID NO: 1); TLKMSVQPTVSLGGFEITPPVVLRLK (SEQ ID NO: 2) and ESFKKQEKTPKTPKGPSSVEDIKAK (SEQ ID NO: 3) or peptide with at least 85% sequence identity to any of SEQ ID NO: 1-3, when there is the presence of phosphorylation of at least one of serine or threonine residue selected from T86, S88, or T95 of the NPM polypeptide, or when there is the absence of phosphorylation on serine residues T234 or S242 of the NPM polypeptide.

In some embodiments, the treatment for kidney injury or AKI is administering an agent which inhibits the phosphorylation of at least one of: T86, S88, T95 of the NMP polypeptide, and/or inhibits the dephsporylation of at least one of: T232 or S240 of the NMP polypeptide, thereby inhibiting the formation of a NMP-Bax complex.

Another aspect described herein relates to a method of determining if a subject has kidney injury or acute kidney injury (AKI), the method comprising:

a. using an assay to detect at least on of:

i. the presence of phosphorylation of at least one of serine or threonine residue selected from: T86, S88, or T95 of the nucleophosmin (NPM) polypeptide in a biological sample obtained from a subject;

ii. the absence of phosphorylation of at least one of at least one serine or threonine residue selected from T234 or S242 on a nucleophosmin (NPM) polypeptide; and b. selecting the subject as having kidney injury or acute kidney injury (AKI), if the subject has the presence of phosphorylation of at least one of: T86, S88, or T95 of the nucleophosmin (NPM) polypeptide is detected, or the absence of phosphorylation of at least one of at least one serine or threonine residue selected from T234 or S242 on a nucleophosmin (NPM) polypeptide, or both, and c. administering an effective amount of a treatment for kidney injury or AKI to the subject diagnosed in step (b).

In some embodiments of the methods described herein, a subject is diagnosed with kidney injury or acute kidney injury (AKI) when the presence of phosphorylation of at least two of: T86, S88, or T95 of the nucleophosmin (NPM) polypeptide is detected, or when the presence of phosphorylation of residues T86, S88, and T95 of the nucleophosmin (NPM) polypeptide is detected, or when the absence of phosphorylation of serine residues T234 and S242 of the nucleophosmin (NPM) polypeptide is detected, or when the presence of phosphorylation of residues of at least one of T86, S88, and T95 of the nucleophosmin (NPM) polypeptide is detected and the absence of phosphorylation of at least one of serine residues T234 and S242 of the nucleophosmin (NPM) polypeptide is detected.

In some embodiments of the methods described herein, an effective amount of a treatment for kidney injury or AKI is administering to the subject is an agent which inhibits the phosphorylation of at least one of: T86, S88, T95 of the NMP polypeptide, and/or inhibits the dephsporylation of at least one of: T232 or S240 of the NMP polypeptide, thereby inhibiting the formation of a NMP-Bax complex.

In some embodiments of the methods described herein, an effective amount of a treatment for kidney injury or AKI is administering to the subject a composition comprising at least one peptide from any peptide comprising the amino acid sequences of: TVTIFVAGVLTASLTIWKKMG (SEQ ID NO: 1); TLKMSVQPTVSLGGFEITPPVVLRLK (SEQ ID NO: 2) and ESFKKQEKTPKTPKGPSSVEDIKAK (SEQ ID NO: 3), or peptide with at least 85% sequence identity to any of SEQ ID NO: 1-3.

Another aspect described herein relates to a method comprising obtaining a biological sample from a subject, and measuring for the presence of phosphorylation of at least one serine or threonine residue on the nucleophosmin (NPM) polypeptide at residues T86, S88, or T95, or measuring the absence of phosphorylation of at least one serine or threonine residue T234 and S242 on the nucleophosmin (NPM) polypeptide, or both. In some embodiments, the method further comprises detecting the presence of phosphorylation of at least two residues on the NMP polypeptide at residues T86, S88, or T95, or detecting the presence of phosphorylation at residues T86, S88, or T95 on the NMP polypeptide, or further comprises detecting the absence of phosphorylation at residues T234 or S242 on the NMP polypeptide.

Another aspect described herein relates to a method comprising obtaining a biological sample from a subject, and measuring for the presence of phosphorylation of at least one serine or threonine residue on the nucleophosmin (NPM) polypeptide at residues T86, S88, or T95, and measuring the absence of phosphorylation of at least one serine or threonine residue T234 and S242 on the nucleophosmin (NPM) polypeptide.

In some embodiments of the methods described herein, the subject is a mammal, e.g., a human. In some embodiments, the subject is at risk of developing renal injury or acute kidney injury (AKI).

In some embodiments of the methods described herein, the biological sample is a urine sample or blood sample, e.g., a blood sample selected from any of the group consisting of; a whole blood sample a plasma sample, a serum sample or a fractionated blood sample.

In some embodiments of the methods described herein, the presence of phosphorylation of at least one residues on the NMP polypeptide at residues T86, S88, or T95 is determined by detecting the presence of binding of a phosphorylation specific antibody that preferentially bind to any one of: phospho-T86, phopho-S88 or phospho-T95 on the NMP polypeptide.

In some embodiments of the methods described herein, the absence of phosphorylation of at least one serine or threonine residue T234 and S242 on the nucleophosmin (NPM) polypeptide is determined by detecting the absence of binding of a phosphorylation specific antibody that preferentially bind to any one of: phospho-T234 or phopho-S242 on the NPM polypeptide.

In some embodiments of the methods described herein, the presence of phosphorylation of at least one residues on the NMP polypeptide at residues T86, S88, or T95 is determined by the presence of binding with at least one of:
 a. a phosphorylation specific antibody or antigen-binding fragment thereof that specifically binds to phospho-T86 on the NMP polypeptide;
 b. a phosphorylation specific antibody or antigen-binding fragment thereof that specifically binds to phospho-S886 on the NMP polypeptide; or
 c. a phosphorylation specific antibody or antigen-binding fragment thereof that specifically binds to phospho-T95 on the NMP polypeptide.

In some embodiments of the methods described herein, the absence of phosphorylation of at least one serine or threonine residue selected from T234 and S242 on the NPM polypeptide is determined by the absence of binding with at least one of:
 a. a phosphorylation specific antibody or antigen-binding fragment thereof that specifically binds to phospho-T234 on the NMP polypeptide; or
 b. a phosphorylation specific antibody or antigen-binding fragment thereof that specifically binds to phospho-S242 on the NMP polypeptide.

In some embodiments of the methods described herein, a site-specific phosphorylation specific antibody or antigen-binding fragment thereof are selected from the group consisting of: a polyclonal antibody, a chimeric antibody, an Fab antigen-binding fragment thereof, fragment, an F(ab')2 antigen-binding fragment thereof, an Fab'antigen-binding fragment thereof, an Fsc antigen-binding fragment thereof, or an Fv antigen-binding fragment thereof. In some embodiments, a site-specific phosphorylation specific antibody or antigen-binding fragment thereof is selected from the group consisting of: a recombinant antibody, a chimeric antibody, a tribody, a midibody or a monoclonoal antibody. In some embodiments, a phosphorylation specific antibody or antigen-binding fragment thereof is a humanized antibody or a human antibody. In some embodiments, antibodies, including but not limited to, a phosphorylation specific antibody or antigen-binding fragment thereof is immobilized on, or attached to, the surface of a solid support, including, but not limited to a solid support surface in the format of a dipstick, a test strip, paper-based assay, a latex bead, a microsphere, or a multi-well plate.

In some embodiments, an antibody, including, but not limited to, phosphorylation specific antibody or antigen-binding fragment thereof comprise a detectable label, or can be bound by a secondary agent which comprises a detectable label.

In some embodiments of the methods described herein, detecting the presence of phosphorylation of at least one serine or threonine residue on the nucleophosmin (NPM) polypeptide at residues T86, S88, or T95, or detecting the absence of phosphorylation of at least one serine or threonine residue T234 and S242 on the nucleophosmin (NPM) polypeptide, or both uses an immunoassay selected from the group consisting of: an ELISA assay, multiplex bead assay, dipstick assay, Western blot analysis, radioimmunoassay (RIA), Immunoradiometric assay (IRMA), chemiluminescent immunoassays, a fluorescence antibody method, passive haemagglutination.

Another aspect relates to a kit comprising a solid support and affixed to the solid support at least one antibody selected from:
 a. a phosphorylation specific antibody or antigen-binding fragment thereof that specifically binds to phospho-T86 on the NMP polypeptide,
 b. a phosphorylation specific antibody or antigen-binding fragment thereof that specifically binds to phospho-S886 on the NMP polypeptide,
 c. a phosphorylation specific antibody or antigen-binding fragment thereof that specifically binds to phospho-T95 on the NMP polypeptide,
 d. a phosphorylation specific antibody or antigen-binding fragment thereof that specifically binds to phospho-T234 on the NMP polypeptide; or
 e. a phosphorylation specific antibody or antigen-binding fragment thereof that specifically binds to phospho-S242 on the NMP polypeptide, f. a specific antibody or antigen-binding fragment thereof that specifically binds to non-phosphorylated T234 (nT234) on the NMP polypeptide; or
g. a specific antibody or antigen-binding fragment thereof that specifically binds to non-phosphorylated S242 (nS242) on the NMP polypeptide, and and an antibody that specifically binds to total NMP polypeptide, and one or more detection means to detect one or more of the antibodies.

In some embodiments, the kit comprises, affixed to the solid support, at least one antibody selected from:
a. a phosphorylation specific antibody or antigen-binding fragment thereof that specifically binds to phospho-T86 on the NMP polypeptide,
b. a phosphorylation specific antibody or antigen-binding fragment thereof that specifically binds to phospho-S886 on the NMP polypeptide,
c. a phosphorylation specific antibody or antigen-binding fragment thereof that
   specifically binds to phospho-T95 on the NMP polypeptide, at least one antibody selected from:
d. a phosphorylation specific antibody or antigen-binding fragment thereof that specifically binds to phospho-T234 on the NMP polypeptide; or
e. a phosphorylation specific antibody or antigen-binding fragment thereof that specifically binds to phospho-S242 on the NMP polypeptide.

In alternative embodiments, the kit comprises, affixed to the solid support:
at least one antibody selected from:
f. a phosphorylation specific antibody or antigen-binding fragment thereof that specifically binds to phospho-T86 on the NMP polypeptide,
g. a phosphorylation specific antibody or antigen-binding fragment thereof that specifically binds to phospho-S886 on the NMP polypeptide,
h. a phosphorylation specific antibody or antigen-binding fragment thereof that specifically binds to phospho-T95 on the NMP polypeptide,
at least one antibody selected from:
a. a specific antibody or antigen-binding fragment thereof that specifically binds to non-phosphorylated T234 (nT234) on the NMP polypeptide; or
b. a specific antibody or antigen-binding fragment thereof that specifically binds to non-phosphorylated S242 (nS242) on the NMP polypeptide.

In some embodiments, the kit can comprise at least 2, or at least 3, or at least 4, or at least 5 specific antibody or antigen-binding fragment thereof described herein.

DESCRIPTION OF THE DRAWINGS

FIG. 1A shows quantitative assessment of NPM in the nuclear and cytosolic cell fractions of primary human proximal tubule epithelial cells (PTECs) subjected to 60 minutes ATP depletion; identical amounts of proteins were loaded in each lane, and densitometric analysis was used to assess the relative amount of NPM present in the cytosolic and noncytosolic fractions before (Base) and after ATP depletion (ATP Depl; n=3). FIG. 1B shows NPM accumulation detected in the cytosolic fraction of renal cortical homogenates harvested from paired donor kidneys with either normal perfusion (normal) or perfusion pump failure (ischemic; results represent four kidneys from two human donors), FIG. 1C shows NPM accumulation in primary murine or human PTECs subjected to ATP depletion 360 minutes, and FIG. 1D shows NPM accumulation in murine and human PTECs subjected to 70 minutes of hypoxia. In B-D, glyceraldehyde-3-phosphate dehydrogenase (GAPDH) serves as a loading control; densitometry represents three independent experiments in each study. Cytosolic fractions were harvested using digitonin (see Methods); noncytosolic extracts were harvested by exposing cells to RIPA buffer after extracting the cytosolic fraction. CTL, control; RDU, relative density unit FIGS. 2A-2D show mass spectrometry reveals consistent differential phosphorylation changes in NPM harvested from in renal cells, kidney tissue, and urine. Representative tracings used to perform differential phosphoproteomic analysis of purified NPM harvested from the renal cortex of an ischemic human kidney are shown. FIG. 2A shows liquid chromatography/mass spectrometry base peak peptide profile of an NPM amino acid fragment. FIG. 2B and FIG. 2C show liquid chromatography/tandem mass spectrometry (MS/MS) peptide collision-induced dissociation fragment ions providing de novo peptide sequence and specific serine phosphorylation sites represented by loss of 2167 D (S-87+ P-80 D). FIG. 2D shows a summary of five differentially NPM-phosphorylated sites altered in a virtually identical manner by ischemic stress in primary murine cells or human proximal tubule epithelial cells (PTECs), murine kidney (mKdy), and human kidney (hKdy) versus control (CTL; murine PTEC, mKdy, and hKdy controls were identical and are shown together). Murine AKI urine (mAKI), human AKI urine (hAKI), and human non-AKI urine (hNonAKI) are also shown. Phosphorylation absent is indicated by a cross; phosphorylation present is indicated by a star. Asterisks show homology between human NPM and murine NPM at residues T234/T232 and S242/S240, respectively. The kinase consensus sequences for each of the five phosphorylation NPM sites are identical between these two species. N/D, not detected.

FIG. 3A-3C shows renal ischemia increases urinary nucleophosmin (NPM). FIG. 3A shows marked accumulation of total NPM in murine urine was detected by dot blot analysis 6 and 12 hours after 25 minutes of transient bilateral renal ischemia, but it disappeared within 48 hours postischemia. In contrast, no urinary NPM was detected at the same time points in sham-operated animals. FIG. 3B is immunohistochemistry showing NPM leakage into the urine in ischemic human kidney after AKI. * identifies that NPM is localized in the urinary space, and arrows indicate medullary tubule cell nuclei. (400× magnification). FIG. 3C shows that ischemic AKI causes NPM re-distrubution. Fresh frozen kidney biopsy sections were double immunostained with a NPM antibody and dectected with a flurescent goat anti-mouse IgG antibody (red) and Hoechst dye #33342. The left pannel shows the NPM localization from a patient with no AKI showing nucleolar localization of NPM distribution typical for normal renal cells (white arrows), whereas the right panel shows ischemic AKI showing NPM diffusely distributed in virtually all cells and the nuclei are negative as reported in ischemic PTEC, and indicates luminal NPM staining (i.e., NPM is localized in the urinary space of kidneys from a subject with AKI).

FIG. 4A-4B shows differentially phosphorylated nucleophosmin (NPM) sites localize near its structural and functional domains. FIG. 4A shows the location of NPM phosphosites detected in postischemic proximal tubule epithelial cells (PTECs), kidney tissue, and urine. Therapeutic peptide #2 (representing NPM amino acids 78-103 (SEQ ID NO: 2)) and 3 (representing NPM amino acids 226-246 (SEQ ID NO: 3)) were designed to interfere with NPM functions at the indicated phospho-sites differentially phosphorylated during ischemic stress. Site-specific amino acid substitutions were made to render each site either constitutively phosphorylated (E substituted for S or T) or constitutively dephosphorylated (A substituted for S or T) to replicate the phosphorylation status of wild-type NPM under resting or ischemic stress conditions (as described in FIG. 2D). FIG. 4B shows a table of all possible combinations of different NPM-phospho-mimics (32 total). Amino acid substitutions mimic each site in either is constitutively phosphorylated state (S or T to E) or constitutively de-phosphorylated state (S or T to A). Therapeutic peptides #2 (SEQ ID NO: 2) (NPM (78-103)) and peptide #3 (SEQ ID NO: 3) (NPM (226-246) replicate native NPM consensus sequences. Peptide #10 is the "normal NPM mimic", and Peptide #22 is the "stress NPM mimetic".

FIG. 5A shows NPM localization in intact renal cells in the absence of stress. FIG. 5B shows NPM oligomers and monomers detected in lysates harvested from nonstressed cells in a native gel; total NPM content is unchanged in each lane, and the increase in monomeric NPM is accompanied by a reciprocal decrease in the oligomeric form of NPM. FIG. 5C shows NPM-Bax complex formation assessed after immunoprecipitation (IP) of flagtagged NPM followed by immunoblot (IB) of conformationally activated Bax (Bax 6A7) after ischemic stress; input protein amounts were similar in each sample. FIG. 5D shows accumulation of NPM and 6A7 Bax in isolated PTEC mitochondria after ischemic stress; VDAC, a mitochondrial membrane protein, serves as loading control. FIG. 5E shows cell survival after 60 minutes ATP depletion (n=6). EV, empty sgOpti vector; RDU, relative density unit. *P, 0.05 for Nor-M and Stress-M NPM phosphomimics versus control (CTL).

FIG. 8A shows that after 28 minutes of bilateral renal pedicle clamping, a single dose (100 μg/g body weight) of NPM-Bax blocking peptide (Peptide #1) was intravenously administered to each of seven paired animal groups at 0, 1, 2, 3, 4, 5, or 6 hours (n=8 animals for each group; total of 56 mice) or control (n=6 animals for each group; total of 42 mice). Blocking peptide administered within 3 hours postischemia significantly improved renal function (i.e., lowered serum BUN) on days 1-7 and dramatically improved animal survival (P, 0.05 versus control). The magnitude of renoprotection was similar with peptide given at 0, 1, and 3 hours postischemia (P, 0.05 for 0 versus 1 or 3 hours); only data for blocking and control peptides administered 3 hours after ischemia are shown. FIG. 8B shows serum creatinine on day 1 (the time of peak kidney dysfunction) was significantly reduced when the blocking peptide was administered 3 hours after ischemia; *P, 0.05 versus control (CTL).

FIG. 9A shows that active Bax immunoprecipitates harvested from human proximal tubule epithelial cell (PTEC) lysates after 60 minutes of ATP depletion plus 30 minutes of recovery. FIG. 9B shows Bax immunoprecititates from renal cortical homogenates after ischemia in the absence of a peptide (None), a control peptide (CTL), or a NPM-Bax blocking peptide (Peptide #1) (Block) injected 3 hours after bilateral renal ischemia. Similar amounts of Bax were detected in each lane, and input protein amounts for each sample were identical. IB, immunoblot; IP, immunoprecipitation.

DETAILED DESCRIPTION OF THE INVENTION

I. Definitions

Figure 1A:
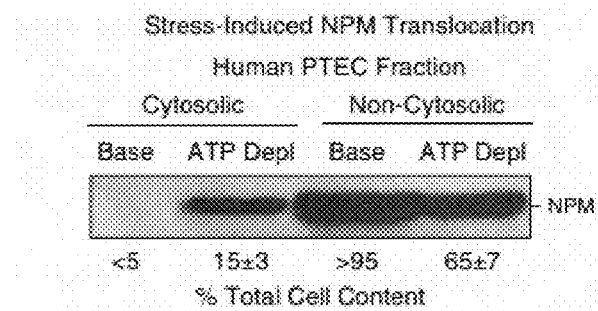
FIGS. 1A-1D show stress causes cytosolic nucleophosmin (NPM) translocation.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-O-911910-19-3); Robert S. Porter et al. (eds.), Fields Virology, 6th Edition, published by Lippincott Williams & Wilkins, Philadelphia, Pa., USA (2013), Knipe, D. M. and Howley, P. M. (ed.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, "kidney injury" includes any injury to the proximal tubule of the kidney and includes, but is not limited to, acute kidney injury (AKI), chronic kidney disease (CKD) and kidney fibrosis.

As used herein, "acute kidney injury", also known as "AKI" or "acute renal failure (ARF)" or "acute kidney failure", refers to a disease or condition where a rapid loss of renal function occurs due to damage to the kidneys, resulting in retention of nitrogenous (urea and creatinine) and non-nitrogenous waste products that are normally excreted by the kidney. Depending on the severity and duration of the renal dysfunction, this accumulation is accompanied by metabolic disturbances, such as metabolic acidosis (acidification of the blood) and hyperkalaemia (elevated potassium levels), changes in body fluid balance, and effects on many other organ systems. It can be characterized by oliguria or anuria (decrease or cessation of urine production), although nonoliguric ARF may occur. Acute kidney injury may be a consequence of various causes including a) pre-renal (causes in the blood supply), which includes, but is not limited to, hypovolemia or decreased blood volume, usually from shock or dehydration and fluid loss or excessive diuretics use; hepatorenal syndrome, in which renal perfusion is compromised in liver failure; vascular problems, such as atheroembolic disease and renal vein thrombosis, which can occur as a complication of nephrotic syndrome; infection, usually sepsis, and systemic inflammation due to infection; severe burns; sequestration due to pericarditis and pancreatitis; and hypotension due to antihypertensives and vasodilators; b) intrinsic renal damage, which includes, but is not limited to, toxins or medication (e.g. some NSAIDs, aminoglycoside antibiotics, iodinated contrast, lithium, phosphate nephropathy due to bowel preparation for colonoscopy with sodium phosphates); rhabdomyolysis or breakdown of muscle tissue, where the resultant release of myoglobin in the blood affects the kidney, which can also be caused by injury (especially crush injury and extensive blunt trauma), statins, stimulants and some other drugs; hemolysis or breakdown of red blood cells, which can be caused by various conditions such as sickle-cell disease, and lupus erythematosus; multiple myeloma, either due to hypercalcemia or "cast nephropathy"; acute glomerulonephritis which may be due to a variety of causes, such as anti-glomerular basement membrane disease/Goodpasture's syndrome, Wegener's granulomatosis or acute lupus nephritis with systemic lupus erythematosus; and c) post-renal causes (obstructive causes in the urinary tract) which include, but are not limited to, medication interfering with normal bladder emptying (e.g. anticholinergics); benign prostatic hypertrophy or prostate cancer; kidney stones; abdominal malignancy (e.g. ovarian cancer, colorectal cancer); obstructed urinary catheter; or drugs that can cause crystalluria and drugs that can lead to myoglobinuria & cystitis.

As used herein, the term "kidney fibrosis" also known as "renal fibrosis" refers to any condition having kidney fibrosis as a symptom or cause of the condition, or a condition that can be worsened by the development of kidney fibrosis, or a condition the progression of which is linked to the progression of kidney fibrosis. Kidney fibrosis is the formation of excess fibrous connective tissue in kidney characterized by glomerulosclerosis and tubulointerstitial fibrosis. The pathogenesis of kidney fibrosis is a monotonous process that is characterized by an excessive accumulation and deposition of extracellular matrix (ECM) components (see e.g., Y. Liu, Kidney International 2006, 69, 213-217). Kidney fibrosis can be evaluated by methods including, but not limited to, histology, immunohistochemistry, Western blot, and real-time PCR for mRNA and protein expression of extracellular matrix including collagen I and alpha-smooth muscle actin, and activation of TGF beta/Smad signaling. Kidney fibrosis can result from various diseases and insults to the kidneys. Examples of such diseases and insults include chronic kidney disease, metabolic syndrome, vesicoureteral reflux, tubulointerstitial renal fibrosis, diabetes (including diabetic nephropathy), and resultant glomerular nephritis (GN), including, but not limited to, focal segmental glomerulosclerosis and membranous glomerulonephritis, mesangiocapillary GN. Since kidney fibrosis is associated with loss of blood vessels, this results in secondary ischemia which can also result in glomerulare disease with loss of glomerular function. Regardless of the primary cause, insults to the kidneys may result in kidney fibrosis and the concomitant loss of kidney function. (Schena, F. and Gesualdo, L., Pathogenic Mechanisms of Diabetic Nephropathy, J. Am. Soc. Nephrol., 16: S30-33 (2005); Whaley-Connell, A., and Sower, J R., Chronic Kidney Disease and the Cardiometabolic Syndrome, J. Clin. Hypert., 8(8): 546-48 (2006)). Conditions associated with kidney fibrosis include, but are not limited to, diabetic nephropathy, chronic kidney disease, end-stage renal disease, systemic lupus erythematosis, vasculitis, IgA nephropathy, other autoimmune diseases, paraprotein diseases, diabetes. In some embodiments, a condition associated with kidney fibrosis results from persistent KIM-1 expression in kidney cells. Renal Fibrosis has three stages which are inflammation reaction stage, formation of fibrosis stage and cicatricial stage respectively. Symptoms vary depending on the stage. There are no obvious symptoms in the inflammation reaction stage. In the formation stage, symptoms occur such as frequent night urine, high potassium, high blood pressure and itchy skin and so on. In the cicatricial stage, renal failure may occur.

As used herein, a "subject" refers to a mammal, preferably a human. The term "individual", "subject", and "patient" are used interchangeably herein, and refer to an animal, for example a mammal, such as a human. The term "mammal" is intended to encompass a singular "mammal" and plural "mammals," and includes, but is not limited: to humans, non-human primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears, as well as commercial livestock and companion animals.

A "subject in need" of treatment for a particular condition can be a subject having that condition, diagnosed as having that condition, or at risk of developing that condition.

As used herein, the terms "sample" or "biological sample" refers to a sample of tissue or fluid obtained from the subject. In some embodiments, the term "blood samples" include, but are not limited to, whole blood, serum or plasma. In some embodiments, the whole blood sample is further processed into serum or plasma samples. The term also includes a mixture of the above-mentioned samples. The term "sample" also includes untreated or pretreated (or pre-processed) samples. In some embodiments, a sample can comprise one or more cells from the subject. In some embodiments, a sample is taken from a human subject, and in alternative embodiments the sample is taken from any mammal, such as rodents, animal models of diseases, commercial animals, companion animals, dogs, cats, sheep, cattle, and pigs, etc. The sample can be pretreated as necessary for storage or preservation, by dilution in an appropriate buffer solution or concentrated, if desired. Any of a number of standard aqueous buffer solutions, employing one of a variety of buffers, such as phosphate, Tris, or the like, at physiological pH can be used. The sample can in certain circumstances be stored for use prior to use in the assays as disclosed herein. Such storage can be at +4° C. or frozen, for example at −20° C. or −80° C. In some embodiments, the biological sample is cryopreserved. In some embodiments, the biological sample is "fixed" or otherwise preserved as to preserve the phosphorylation status of the biological sample, and/or treated with phosphatase inhibitors and/or kinase inhibitors to prevent dephosphorylation or phosphorylation events from occurring after obtaining the biological sample from the subject. In some embodiments, the biological sample is immediately frozen in liquid nitrogen or dry ice to preserve the phosphorylation status of the biological sample.

As used herein, the term "biomarker" or refers to a phenotype of a polypeptide expressed endogenously in an individual or found or sequestered in a sample from an individual. The term "acute kidney injury biomarker" is used throughout the specification as an example of a type of biomarker useful with the methods described herein. Acute kidney injury and pyelonephritis are examples of conditions associated with a biomarker as the term "biomarker" is used herein. A biomarker or acute kidney injury biomarker can include the NPM polypeptide with at least 1, 2, 3, 4 or all 5 of the phosphorylation states of: pT86, pS88, pT95, nT234, nS242. The phosphorylation status of the NPM polypeptide as a biomarker useful for diagnosing AKI also encompasses domains or fragments of NPM polypeptide, as well as species, variants, homologues, allelic forms, mutant forms, and equivalents of NPM polypeptide. In some embodiments, the NPM polypeptide is human NPM polypeptide.

The terms "polynucleotide" and "nucleic acid," used interchangeably herein, refer to a polymeric form of nucleotides of any length, either ribonucleotides or deoxyribonucleotides. Thus, this term includes single, double, or multi-stranded DNA or RNA, genomic DNA, cDNA, DNA-RNA hybrids, or a polymer including purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present disclosure. An "expression cassette" includes a DNA coding sequence operably linked to a promoter.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A DNA sequence that "encodes" a particular RNA or protein gene product is a DNA nucleic acid sequence that is transcribed into the particular RNA and/or protein. A DNA polynucleotide may encode an RNA (mRNA) that is translated into protein, or a DNA polynucleotide may encode an RNA that is not translated into protein (e.g., tRNA, rRNA, or a DNA-targeting RNA; also called "non-coding" RNA or "ncRNA").

As used herein the term "agent" refers to a protein-binding agent that specifically binds to a target protein and permits detection and/or quantification of phosphorylation levels, as well as protein concentrations, expression levels, or activity of the total protein in a biological sample. Such protein-binding agents include, but are not limited to, small molecules, antibodies, antibody fragments (e.g., antigen-binding fragments of antibodies), recombinant antibodies, chimeric antibodies, tribodies, midibodies, protein-binding agents, small molecules, recombinant protein, peptides, aptamers, avimers and protein-binding derivatives or fragments thereof.

The terms "protein-binding molecule" refers to an agent or protein which specifically binds to a protein, such as a protein-binding molecule which specifically binds a NPM polypeptide or a particular phosphorylation site on the NPM polypeptide (any one or more of: pT86, pS88, pT95, nT234, nS242). Protein-binding molecules are well known in the art, and include antibodies, protein-binding peptide and the like. The region on the protein which binds to the protein-binding molecule is referred to as the epitope, and the protein which is bound to the protein-binding molecule is often referred to in the art as an antigen.

As used herein, the term "antibody" refers to immunoglobulin molecules and immunologically active portions of immunoglobulin molecules, i.e., molecules that contain an antigen binding site that specifically bind an antigen. The terms also refers to antibodies comprised of two immunoglobulin heavy chains and two immunoglobulin light chains as well as a variety of forms besides antibodies; including, for example, Fv, Fab, and F(ab)'2 as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). In some embodiments, antibody reagents, e.g. antibodies, monoclonal and chimeric antibodies useful in the methods as disclosed herein can be manufactured using well-known methods, e.g., as described in Howard and Kaser "Marking and Using Antibodies: A Practical Handbook" CRC Press (2006); which is incorporated by reference herein in its entirety. Antibody fragments or antigen-binding antibody fragments includes any protein or peptide containing molecule that comprises at least a portion of an immunoglobulin molecule, and include, but are not limited to a complementarily determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The antibodies can be polyclonal or monoclonal and can be isolated from any suitable biological source, e.g., murine, rat, sheep and canine. Additional sources are identified infra. The term "antibody" is further intended to encompass digestion fragments, specified portions, derivatives and variants thereof, including antibody mimetics or comprising portions of antibodies that mimic the; structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab') 2 fragment, a bivalent fragment comprising two Fab fragments linked by a disulfide bridge at the hinge region; a Ed fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarily determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad. Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The terms "antigen-binding fragment" or "antigen-binding domain", which are used interchangeably herein to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. The phrase can also refer to continuous or discontinuous epitopes in which the primary sequence (i.e., the amino acid sequence) is not similar but nonetheless the epitopes are still recognized by the same antibody.

The term "antibody variant" is intended to include antibodies produced in a species other than a mouse. It also includes antibodies containing post translational modifications to the linear polypeptide sequence of the antibody or fragment. It further encompasses fully human antibodies. The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies, chimeric, recombinant and humanized.

The term "human antibody" as used herein, is intended to include antibodies having variable and constant regions derived from human germline immunoglobulin sequences. The human antibodies of the present invention can include amino acid residues not encoded by human germline immunoglobulin sequences (e.g., mutations introduced by random or site-specific mutagenesis in vitro or by somatic mutation in viva). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, CL, CH domains (e.g., CH1, CH2, CH3), hinge, (Via, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain); genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody can be at least about 95%, or even at least about 96%, or least about 97%, or least about 98%, or least about 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody can display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human monoclonal antibody" refers to antibodies displaying a single binding specificity which have variable and constant regions derived from human germline immunoglobulin sequences. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in viva somatic mutagenesis) and thus the amino acid sequences of the VH and VL regions of the recombinant antibodies are sequences that, while derived from and related to human germline VH and VL sequences, can not naturally exist within the human antibody germline repertoire in vivo. As used herein, "isotype" refers to the antibody class (e.g., IgM or IgG1) that is encoded by heavy chain constant region genes.

An "antigen-binding site" or "binding portion" refers to the part of an immunoglobulin molecule that participates in antigen binding. The antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

As used herein, the term "specific binding" refers to a chemical interaction between two molecules, compounds, cells and/or particles wherein the first entity (e.g., antibody or antigen-binding fragment) binds to the second, target entity (e.g., NPM polypeptide, and/or the specific phosphorylation sites of pT86, pS88, pT95, nT234, nS242 the NPM polypeptide) with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. In particular, the terms "specifically binds," "specific binding affinity" (or simply "specific affinity"), and "specifically recognize," and other related terms when used to refer to binding between a protein and an antibody, refers to a binding reaction that is determinative of the presence of the protein in the presence of a heterogeneous population of proteins and other biologics. Thus, under designated conditions, a specified antibody binds preferentially to a particular epitope (e.g., any one of pT86, pS88, pT95, nT234, nS242 on the NPM polypeptide) and does not bind in a significant amount to other proteins present in the sample. An antibody that specifically binds to a protein has an association constant of at least $10^3 M^{-1}$ or $10^4 M^{-1}$, sometimes $10^5 M^{-1}$ or $10^6 M^{-1}$, in other instances $10^6 M^{-1}$ or $10^{10} M^{-1}$, preferably $10^8 M^{-1}$ to $10^9 M^{-1}$, and more preferably, about $10^{10} M^{-1}$ to $10^{11} M^{-1}$ or higher. Protein-binding molecules with affinities greater than $10^8 M^{-1}$ are useful in the methods of the present invention. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

An "array" broadly refers to an arrangement of agents (e.g., proteins, antibodies, replicable genetic packages) in positionally distinct locations on a substrate. In some instances the agents on the array are spatially encoded such that the identity of an agent can be determined from its location on the array. A "microarray" generally refers to an array in which detection requires the use of microscopic detection to detect complexes formed with agents on the substrate. A "location" on an array refers to a localized area on the array surface that includes agents, each defined so that it can be distinguished from adjacent locations (e.g., being positioned on the overall array, or having some detectable characteristic, that allows the location to be distinguished from other locations). Typically, each location includes a single type of agent but this is not required. The location can have any convenient shape (e.g., circular, rectangular, elliptical or wedge-shaped). The size or area of a location can vary significantly. In some instances, the area of a location is greater than 1 cm2, such as 2 cm2, including any area within this range. More typically, the area of the location is less than 1 cm2, in other instances less than 1 mm2, in still other instances less than 0.5 $mm^2$, in yet still other instances less than 10,000 $mm^2$, or less than 100 $mm^2$.

A "label" refers to an agent that can be detected by using physical, chemical, optical, electromagnetic and/or other methods. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

As used herein, the terms "proteins" and "polypeptides" are used interchangeably to designate a series of amino acid residues connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, affectation.

The term "cancer" or "malignancy" are used interchangeably herein, refers to diseases that are characterized by uncontrolled, abnormal growth of cells which results in an increase in a particular cell type or increase in a tissue growth or tissue mass. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

As used herein, the term "tumor" refers to a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and showing a high degree of anaplasia. Anaplasia is the reversion of cells to an immature or a less differentiated form, and it occurs in most malignant tumors.

The term "renal cell carcinoma" and "RCC" are used interchangeably herein, refers to a tumor of the kidney. Tumors of the kidney can be malignant or benign and are the most common primary malignant kidney tumor. RCC usually begins in the cells that line the small tubes of each nephron. Renal cell tumors can grow as a single mass, and can multiple RCC tumors can develop on a single kidney or both kidneys. The term RCC encompasses different subtypes of RCC, such as, but not limited to epithelial renal cell carcinoma (RCC), clear cell (conventional), papillary RCC (chromophil), chromophobe RCC, collecting duct RCC (<1%) and unclassified RCC subtypes.

The term "clear cell RCC" also referred to as "ccRCC" refers to the most common renal neoplasm seen in adults (70% of tumors derived from tubular epithelium). Clear cell RCC can be as small as 1 cm or less and discovered incidentally, or it can be as bulky as several kilograms, and often presents pain, as a palpable mass or with hematuria, but a wide variety of paraneoplastic syndromes have been described. Clear cell RCC might be clinically silent for years and may present with symptoms of metastasis. Clear cell RCC has a characteristic gross appearance; the tumor is solid, lobulated, and yellow, with variegation due to necrosis and hemorrhage, with in some instances, the tumor circumscribed, or invade the perirenal fat or the renal vein.

As used herein, the terms "treat," "treatment," "treating," or "amelioration" refer to therapeutic treatments, wherein the object is to reverse, alleviate, ameliorate, inhibit, slow down or stop the progression or severity of a condition associated with kidney injury, e.g., AKI, chronic kidney disease or RCC. The term "treating" is not intended to cure disease or condition associated with AKI or chronic kidney disease. The term "treating" includes reducing or alleviating at least one adverse effect or symptom of a condition, disease or disorder, e.g., a condition associated with AKI or chronic kidney disease. Treatment is generally "effective" if one or more symptoms or clinical markers are reduced. Alternatively, treatment is "effective" if the progression of a disease is reduced or halted. That is, "treatment" includes not just the improvement of symptoms or markers (e.g., a decrease in NPM polypeptide having a ischemic-induced phosphorylation state), but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. For example, treatment is considered effective if the extent or amount of AKI or chronic kidney disease is reduced, or the progression of AKI or chronic kidney disease is halted. In another example, treatment is considered effective if renal function is improved. The term "treatment" of a disease also includes providing relief from the symptoms or side-effects of the disease (including palliative treatment).

As used herein, the term "treating" with respect to treatment of kidney injury or ischemia includes reducing or alleviating at least one adverse effect or symptom of a condition, disease or disorder associated with kidney injury or ischemia. As used herein, the term treating is used to refer to the reduction of a symptom and/or a biochemical of kidney injury or ischemia by at least 10%. As a non-limiting example, a treatment can be measured by a decrease the presence of one or more of: pT86, pS88, pT95 on the NPM polypeptide and/or an increase in one or more of pT234, pS242 of the NPM polypeptide as disclosed herein, for example a decrease by at least 10% of the presence of one or more of: pT86, pS88, pT95 on the NPM polypeptide, or an increase by at least 10% of pT234, pS242 of the NPM polypeptide as compared to the phosphorylation status of the NPM polypeptide obtained from the subject at an earlier timepoint. In some embodiments, the terms "treat" and "treatment" is administration of an appropriate therapy to the subject identified with RCC for a beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total). "Treatment" can also mean prolonging survival as compared to expected survival if not receiving treatment. Those in need of treatment include those already diagnosed with cancer as well as those likely to develop secondary tumors due to metastasis.

The term "effective amount" as used herein refers to the amount of therapeutic agent or pharmaceutical composition to reduce or alleviate or at least one symptom or marker of the disease or disorder, for example a symptom of ischemia, kidney injury or AKI. For example, an effective amount using the methods as disclosed herein would be considered as the amount sufficient to reduce a symptom or marker of the disease or disorder by at least 10%. An effective amount as used herein would also include an amount sufficient to prevent or delay the development of a symptom of the disease, alter the course of a symptom disease (for example but not limited to, slowing the progression of a symptom of the disease), or reverse a symptom of the disease.

The term "effective amount" as used herein refers to the amount of an agent which inhibits the formation of the Bax-NPM complex, or a NPM inhibitory peptide as described herein, needed to alleviate at least one or more symptom of the disease or disorder being treated, and relates to a sufficient amount of pharmacological composition to provide the desired effect. The term "therapeutically effective amount" therefore refers to an amount of an agent which inhibits the formation of the Bax-NPM complex, or a NPM inhibitory peptide as described herein, using the methods as disclosed herein, that is sufficient to provide a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an agent which inhibits the formation of the Bax-NPM complex, or a NPM inhibitory peptide, as described herein, which achieves a half-maximal inhibition of measured function or activity) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment. Depending on the type and severity of the chronic kidney disease, about 1 µg/kg to 100 mg/kg (e.g., 0.1-20 mg/kg) of an agent which inhibits the formation of the Bax-NPM complex, or a NPM inhibitory peptide as described herein is an initial candidate dosage range for administration to the subject, whether, for example, by one or more separate administrations, or by continuous infusion.

As used herein, the term "pharmaceutical composition" refers to the one or more active agents in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject, e.g. parenteral, intravenous, intralesional, or intratumoral. Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection. The administration can be systemic or local.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutically active substances is well known in the art. Supplementary active ingredients can also be incorporated into the compositions. The phrase "pharmaceutically-acceptable" refers to molecular entities and compositions that do not produce a toxic, an allergic, or similar untoward reaction when administered to a host.

The term "in vivo" refers to assays or processes that occur in or within an organism, such as a multicellular animal. In some of the aspects described herein, a method or use can be said to occur "in vivo" when a unicellular organism, such as a bacterium, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing of a programmable synthetic biological circuit in a non-cellular system, such as a medium not comprising cells or cellular systems, such as cellular extracts.

The term "subject" as used herein refers to a human or animal, to whom treatment, including prophylactic treatment, according to the present invention, is provided. Usually the animal is a vertebrate such as, but not limited to a primate, rodent, domestic animal or game animal. Primates include but are not limited to, chimpanzees, cynomologous monkeys, spider monkeys, and macaques, e.g., Rhesus. Rodents include mice, rats, woodchucks, ferrets, rabbits and hamsters. Domestic and game animals include, but are not limited to, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate or a human. A subject can be male or female. Additionally, a subject can be an infant or a child. In some embodiments, the subject can be a neonate or an unborn subject, e.g., the subject is in utero. Preferably, the subject is a mammal. The mammal can be a human, non-human primate, mouse, rat, dog, cat, horse, or cow, but is not limited to these examples. Mammals other than humans can be advantageously used as subjects that represent animal models of diseases and disorders. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. In some embodiments, the subject can be a patient or other subject in a clinical setting. In some embodiments, the subject is already undergoing treatment. In some embodiments, the subject is an embryo, a fetus, neonate, infant, child, adolescent, or adult. In some embodiments, the subject is a human fetus, human neonate, human infant, human child, human adolescent, or human adult. In some embodiments, the subject is an animal embryo, or non-human embryo or non-human primate embryo. In some embodiments, the subject is a human embryo.

The term "derivative" as used herein refers to proteins or peptides (e.g., NPM inhibitory peptides or fusion proteins thereof) which have been chemically modified, for example but not limited to by techniques such as ubiquitination, labeling, pegylation (derivatization with polyethylene glycol) or addition of other molecules.

As used herein, "variant" with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a NPM inhibitory peptides for example, is meant to refer to a molecule substantially similar in structure and function, i.e. where the function is the ability to bind to biotin or a biotin derivative, or to a lipoic acid compound as disclosed herein. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical.

For example, a variant of NPM inhibitory peptides can contain a mutation or modification that differs from a reference amino acid of SEQ ID NO: 1 or SEQ ID NO: 2 or SEQ ID NO: 3. In some embodiments, a variant can be a different isoform of a NPM protein or can comprise different isomer amino acids. Variants can be naturally-occurring, synthetic, recombinant, or chemically modified polynucleotides or polypeptides isolated or generated using methods well known in the art. Variants can include conservative or nonconservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins.

The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the BBB). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In some embodiments, individual substitutions, deletions or additions that alter, add or delete a single amino acid or a small percentage of amino acids can also be considered "conservative substitutions" is the change does not reduce the activity of the peptide (i.e. the ability of, for example MIS to bind and activate MISRII). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents. As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

The terms "insertion" or "deletion" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "functional derivative" and "mimetic" are used interchangeably, and refers to a compound which possess a biological activity (either functional or structural) that is substantially similar to a biological activity of the entity or molecule its is a functional derivative of The term functional derivative is intended to include the fragments, variants, analogues or chemical derivatives of a molecule. 1001091A "fragment" of a molecule, is meant to refer to any contagious polypeptide subset of the molecule. Fragments of, for example a NPM polypeptide of SEQ ID NO: 4 which have the same activity as that of amino acid of SEQ ID NO: 2 or SEQ ID N: 3 are also encompassed for use in the present invention.

An "analog" of a molecule such as a NPM inhibitory peptide, for example an analogue of the protein of amino acid of SEQ ID NO: 1 or SEQ ID NO: 2 or SEQ ID NO: 3 is meant to refer to a molecule similar in function to either the entire molecule or to a fragment thereof of SEQ ID NO: 1 or SEQ ID NO: 2 or SEQ ID NO: 3, respectively. As used herein, a molecule is said to be a "chemical derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

As used herein, "homologous", when used to describe a polypeptide or polynucleotide, indicates that two polypeptides or two polynucleotides, or designated sequences thereof, when optimally aligned and compared, are identical, with appropriate amino acid or nucleotide insertions or deletions, in at least 70% of the amino acids or nucleotides, usually from about 75% to 99%, and more preferably at least about 98 to 99% of the amino acids or nucleotides.

The term "homolog" or "homologous" can also be used with respect to structure and/or function. With respect to amino acid sequence homology, amino acid sequences are homologs if they are at least 50%, at least 60 at least 70%, at least 80%, at least 90%, at least 95% identical, at least 97% identical, or at least 99% identical. The term "substantially homologous" refers to sequences that are at least 90%, at least 95% identical, at least 97% identical or at least 99% identical. Homologous sequences can be the same functional gene in different species.

As used herein, the term "substantial similarity" in the context of polypeptide sequences, indicates that the polypeptide comprises a sequence with at least 60% sequence identity to a reference sequence, or 70%, or 80%, 85% or 87% sequence identity to the reference sequence, or most preferably 90% identity over a comparison window of about 10-20 amino acid residues. In some embodiments, a NPM inhibitory peptide with substantial similarity to SEQ ID NO: 1 is a peptide that has at least about 70%, or about 80%, or about 85% or about 87% or about 90% or more sequence identity to SEQ ID NO: 1, and can have a similar biological function or activity, e.g., at least 80% ability to inhibit the Bax-NPM complex formation as compared to the inhibitory NPM peptide of SEQ ID NO: 1.

In the context of amino acid sequences, "substantial similarity" further includes conservative substitutions of amino acids. Thus, a polypeptide is substantially similar to a second polypeptide, for example, where the two peptides differ by one or more conservative substitutions. The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

Determination of homologs of the genes or peptides of the present invention can be easily ascertained by the skilled artisan. The terms "homology" or "identity" or "similarity"

are used interchangeably herein and refers to sequence similarity between two peptides or between two nucleic acid molecules. Homology and identity can each be determined by comparing a position in each sequence which can be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present application.

In one embodiment, the term "NPM inhibitory peptide homolog" refers to an amino acid sequence that has 40% homology to the reference sequence of the NPM inhibitory peptide. Using SEQ ID NO: 1 as the exemplary NPM inhibitory peptide as disclosed herein, a NPM inhibitory peptide homolog has 40% sequence identity or more preferably at least about 50%, still more preferably, at least about 60% sequence identity, still more preferably, at least about 70% sequence identity, even more preferably, at least about 75% sequence identity, yet more preferably, at least about 80% sequence identity, even more preferably at least about 85% homology, still more preferably, at least about 90% sequence identity, and more preferably, at least about 95% sequence identity to the amino acids of SEQ ID NO: 1. As discussed above, homology refers to a sequence identity of between about 40% to 100% and all intervals in between (i.e., 55%, 60%, 70%, 75%, 80%, 85%, 90%, 95%, 98%, etc.).

The term "sequence identity" with reference to nucleic acid sequences refers to the relatedness between two nucleotide sequences. For purposes of the present disclosure, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows: (Identical Deoxyribonucleotides-.times.100)/(Length of Alignment-Total Number of Gaps in Alignment). The length of the alignment is preferably at least 10 nucleotides, preferably at least 25 nucleotides more preferred at least 50 nucleotides and most preferred at least 100 nucleotides.

The term "homology" or "homologous" as used herein is defined as the percentage of nucleotide residues in the homology arm that are identical to the nucleotide residues in the corresponding sequence on the target chromosome, after aligning the sequences and introducing gaps, if necessary, to achieve the maximum percent sequence identity. Alignment for purposes of determining percent nucleotide sequence homology can be achieved in various ways that are within the skill in the art, for instance, using publicly available computer software such as BLAST, BLAST-2, ALIGN, ClustalW2 or Megalign (DNASTAR) software. Those skilled in the art can determine appropriate parameters for aligning sequences, including any algorithms needed to achieve maximal alignment over the full length of the sequences being compared. In some embodiments, a nucleic acid sequence (e.g., DNA sequence), for example of a homology arm of a repair template, is considered "homologous" when the sequence is at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to the corresponding native or unedited nucleic acid sequence (e.g., genomic sequence) of the host cell.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference sample), or any decrease between 10-100% as compared to a reference level. In the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to a standard definition of statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties. Other terms are defined herein within the description of the various aspects of the invention.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

II. NPM

Nucleophosmin (NPM), also known as B23, NO38, or numatrin (Lim and Wang, 2006), is a nucleolar phosphoprotein composed of an N-terminal globular domain (1-110 residues) and a C-terminal domain (111-294 residues) rich in acidic residues. NPM was initially identified as a critical player in ribosome biogenesis (Lim and Wang, 2006). Since then a number of cellular activities associated with NPM indicate that this protein has multiple functions, especially in cell proliferation, cytoplasmic/nuclear shuttle transportation, nucleic acid binding, ribonucleic cleavage, centrosome duplication and molecular chaperoning; (Okuda, 2002; Okuwaki et al, 2001; Ye, 2005). NPM shuttles between the nucleolus and the cytoplasm, and it also translocates from the nucleolus to the nucleoplasm during the stationary phase of growth or during treatment with certain antitumor drugs (Chou and Yung, 1995; Yung et al, 1990).

Nucleophosmin is also known as, NPM, NPM1, nucleophosmin 1, B23, nucleolar phosphoprotein B23, numatrin, nucleophosmin/nucleoplasmin family, member 1. The sequence of NPM for a number of species is well known in the art, e.g. human NPM (e.g. SEQ ID NO: 4, NCBI Ref Seq: NP_002511.1), and is encoded by NM_002520.6. The amino acid sequence of human NPM polypeptide is as follows, with the 5 serine (S) or threonine (T) sites (T86, S88, T95, T234 or S242) that are differentially phosphorylated under ischemic condition highlighted in bold and italics:

The inventors have previously discovered that nucleophosmin (NPM), a highly conserved, ubiquitously expressed nucleolar protein essential for mammalian cell survival, 16-18 also facilitates PTEC death in a Bax-dependent manner.13 In normal cells, NPM acts as a protein chaperone that shuttles between the nucleus and cytosol to promote protein synthesis, ribosomal biogenesis, and cell proliferation.13, 17,19,20, During ischemic stress, however, NPM rapidly enters the cytosol and complexes with conformationally activated Bax, and together, NPM and Bax cause mitochondrial injury and cell death.13 NPM exists in two forms: large

```
                                                                  (SEQ ID NO: 4)
medsmdmdms plrpqnylfg celkadkdyh fkvdndeneh qlslrtvslg agakdelhiv eaeamnyegs pikvtlatlk msvqptvslg gfeitppvvl rlkcgsgpvh isgqhlvave edaesedeee edvkllsisg krsapgggsk vpqkkvklaa dedddddee dddeddddd fddeeaeeka pvkksirdtp aknaqksnqn gkdskpsstp rskgqesfkk qektpktpkg pssvedikak mqasiekggs lpkveakfin yvkncfrmtd qeaiqdlwqw rksl
```

The NPM polypeptide of SEQ ID NO: 4 is encoded by RefSeq ID: NM_002520.6, which is as follows:

multimers which are restricted to the nucleus and monomers capable of entering the cytosol.21 In general, oligomeric

```
                                                                  (SEQ ID NO: 7)
   1    agaaaggagt ggggttgaaa agcgcttgcg caggacggct acggtacggg ggtgggaggg 61    cttcggagca cgcgcgcgga ggcgggactt gggaagcgct cgcgagatct tcagggtcta 121    tatataagcg cggggagcct gcgtcctttc cctggtgtga ttccgtcctg cgcggttgtt 181    ctctggagca gcgttctttt atctccgtcc gccttctctc ctacctaagt gcgtgccgcc 241    acccgatgga agattcgatg gacatggaca tgagccccct gaggcccag aactatcttt 301    tcggttgtga actaaaggcc gacaaagatt atcactttaa ggtggataat gatgaaaatg 361    agcaccagtt atctttaaga acggtcagtt taggggctgg tgcaaaggat gagttgcaca 421    ttgttgaagc agaggcaatg aattacgaag gcagtccaat taaagtaaca ctggcaactt 481    tgaaaatgtc tgtacagcca acggtttccc ttgggggctt tgaaataaca ccaccagtgg 541    tcttaaggtt gaagtgtggt tcagggccag tgcatattag tggacagcac ttagtagctg 601    tggaggaaga tgcagagtca gaagatgaag aggaggagga tgtgaaactc ttaagtatat 661    ctggaaagcg gtctgcccct ggaggtggta gcaaggttcc acagaaaaaa gtaaaacttg 721    ctgctgatga agatgatgac gatgatgatg aagaggatga tgatgaagat gatgatgatg 781    atgattttga tgatgaggaa gctgaagaaa aagcgccagt gaagaaatct atacgagata 841    ctccagccaa aaatgcacaa aagtcaaatc agaatggaaa agactcaaaa ccatcatcaa 901    caccaagatc aaaaggacaa gaatccttca gaaacagga aaaaactcct aaaacaccaa 961    aaggacctag ttctgtagaa gacattaaag caaaaatgca agcaagtata gaaaaaggtg 1021    gttctcttcc caaagtggaa gccaaattca tcaattatgt gaagaattgc ttccggatga 1081    ctgaccaaga ggctattcaa gatctctggc agtggaggaa gtctctttaa gaaaatagtt 1141    taaacaattt gttaaaaaat tttccgtctt atttcatttc tgtaacagtt gatatctggc 1201    tgtcctttt ataatgcaga gtgagaactt tccctaccgt gtttgataaa tgttgtccag 1261    gttctattgc caagaatgtg ttgtccaaaa tgcctgttta gtttttaaag atggaactcc 1381    acccttttgct tggttttaag tatgtatgga atgttatgat aggacatagt agtagcggtg 1381    gtcagacatg gaaatggtgg ggagacaaaa atatacatgt gaaataaaac tcagtatttt 1441    aataaagta
```

NPM promotes cell proliferation, whereas monomeric NPM enhances death21 after proapoptotic insults that activate Bax in both cancer 22,23 and noncancer 13 cells. The post-translational modifications that convert NPM from its essential role in normal cell housekeeping to a cytotoxin during stress are completely unknown.

Interestingly, neither conformational Bax activation or cytosolic NPM accumulation alone are toxic, suggesting that both events are required to induce cell death[13]. Prior experimental evidence shows that NPM de-oligomerizes to form monomers, translocates from the nucleus to the cytosol in order to bind Bax in its conformationally altered, i.e., "active" form that exposes the 6A7 epitope[22, 23, 24, 25].

In particular, the authors investigated stress-induced differential phosphorylation of nucleophosmin (NPM), a chaperone of the apoptotic factor Bax, finding a virtually identical NPM stress-induced phosphorylation pattern in mouse and human primary renal cells, fresh kidney tissue, and urine within hours of injury. An NPM mimic protein that replicates this pattern (but not a mimic with a normal pattern) is toxic to renal cells. Administering targeted peptides designed to reduce NPM toxicity, even hours after a typically lethal ischemic insult, improves cell and animal survival. As such, the inventors demonstrate that stress-induced NPM phosphorylation is a contributor to renal cell death in human AKI and specific ischemic-induced NPM phosphorylation changes that potentially guide early diagnosis and management

III. NPM Inhibitor Agents and Inhibitors of Bax-NPM Complex Formation as Therapeutics for AKI and Renal Injury One aspect of the technology described herein relates to a method to treat a subject any of: acute kidney injury (AKI) or ischemia, comprising administering a subject a composition comprising at least one agent which inhibits the formation of the Bax-NPM complex. In some embodiments, an inhibitor of a Bax-NPM complex is a NPM inhibitory peptide as discussed herein. In some embodiments, a NPM inhibitory peptide selected from the group consisting of: TVTIFVAGVLTASLTIWKKMG (SEQ ID NO: 1); TLKMSVQPTVSLGGFEITPPVVLRLK (peptide #2) (SEQ ID NO: 2) and ESFKKQEKTPKTPKGPSSVEDIKAK (peptide #3) (SEQ ID NO: 3), or a peptide with at least 85% or 90% or 95% sequence identity to any of SEQ ID NO: 1-3.

As used herein, an agent which inhibits the formation of the Bax-NPM complex, or a NPM inhibitory peptide as disclosed herein has the ability to reduce the activity of the ischemic-induced phosphorylated form of the NPM polypeptide (i.e., having the phosphorylation status of one or more of pT86, pS88, pT95, nT234, nS242) and/or its binding to Bax (i.e., inhibit Bax-NPM complex formation) by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or more, relative to the activity of the normal form of the NPM polypeptide (i.e., having the phosphorylation status of nT86, nS88, nT95, pT234, pS242) or binding of the normal NPM polypeptide to Bax level in the absence of the NPM peptide.

As used herein, the terms an "agent which inhibits the formation of the Bax-NPM complex", 'Bax-NPM complex inhibitor", "NPM antagonist," "NPM inhibitor peptide," and "NPM inhibitor agent" refer to a molecule or agent that significantly blocks, inhibits, reduces, or interferes with the ischemic-induced phosphorylated form of the NPM polypeptide (i.e., having the phosphorylation status of one or more of pT86, pS88, pT95, nT234, nS242) biological activity in vitro, in situ, and/or in vivo, including activity of downstream signalling pathways mediated by the phosphorylated form of the NPM polypeptide, such as, for example, NPM interaction with Bax and/or complex formation with Bax to form a Bax-NPM complex, and down stream Bax-mediated cell death, and/or elicitation of a cellular response to Bax or the Bax-NPM complex.

The term "agent" as used herein in reference to an agent which inhibits the formation of the Bax-NPM complex, or a NPM inhibitor agent means any compound or substance such as, but not limited to, a small molecule, nucleic acid, polypeptide, peptide, drug, ion, etc. An "agent" can be any chemical, entity, or moiety, including, without limitation, synthetic and naturally-occurring proteinaceous and non-proteinaceous entities. In some embodiments of the aspects described herein, an agent is a nucleic acid, a nucleic acid analogue, a protein, an antibody, a peptide, an aptamer, an oligomer of nucleic acids, an amino acid, or a carbohydrate, and includes, without limitation, proteins, oligonucleotides, ribozymes, DNAzymes, glycoproteins, antisense RNAs, siRNAs, lipoproteins, aptamers, and modifications and combinations thereof etc. Compounds for use in the therapeutic compositions and methods described herein can be known to have a desired activity and/or property, or can be selected from a library of diverse compounds, using screening methods known to one of ordinary skill in the art.

Exemplary agents which inhibits the formation of the Bax-NPM complex, or a NPM inhibitor agent contemplated for use in the various aspects and embodiments described herein include, but are not limited to, anti-NPM antibodies or antigen-binding fragments thereof that specifically bind to the ischemic-induced phosphorylated form of the NPM polypeptide (i.e., having the phosphorylation status of one or more of pT86, pS88, pT95, nT234, nS242); anti-sense molecules directed to a nucleic acid encoding NPM polypeptide; short interfering RNA ("siRNA") molecules directed to a nucleic acid encoding NPM polypeptide; RNA or DNA aptamers that bind to the ischemic-induced phosphorylated form of the NPM polypeptide (i.e., having the phosphorylation status of one or more of pT86, pS88, pT95, nT234, nS242), and inhibit/reduce/block signaling by the ischemic-induced phosphorylated form of the NPM polypeptide (i.e., having the phosphorylation status of one or more of pT86, pS88, pT95, nT234, nS242) structural analogs of the ischemic-induced phosphorylated form of the NPM polypeptide (i.e., having the phosphorylation status of one or more of pT86, pS88, pT95, nT234, nS242); and soluble proteins of the ischemic-induced phosphorylated form of the NPM polypeptide (i.e., having the phosphorylation status of one or more of pT86, pS88, pT95, nT234, nS242), inhibitory NPM polypeptides, NPM inhibitory peptides as disclosed herein, e.g., dominant negative NPM inhibitory peptides, or fusion polypeptides thereof. In some embodiments of these aspects and all such aspects described herein, an inhibitor of the formation of the Bax-NPM complex, or a NPM inhibitor agent (e.g., an antibody or antigen-binding fragment thereof) binds (physically interacts with) the ischemic-induced phosphorylated form of the NPM polypeptide (i.e., having the phosphorylation status of one or more of pT86, pS88, pT95, nT234, nS242), targets downstream signaling of the ischemic-induced phosphorylated form of the NPM polypeptide (i.e., having the phosphorylation status of one or more of pT86, pS88, pT95, nT234, nS242), and/or inhibits (reduces) the change of phosphorylation states of the NPM polypeptide from the normal phosphorylation state (e.g., nT86, nS88, nT95, pT234, pS242) to the ischemic-induced phosphorylated form having the phosphorylation status of one or more of pT86, pS88, pT95, nT234, nS242), as well as NPM polypeptide production or release. In some embodiments of these aspects and all such aspects described herein, an inhibitor of the formation of the Bax-NPM complex, or a NPM inhibitor agent binds and prevents its binding Bax. In some embodiments of these aspects and all such aspects described herein, an inhibitor of the formation of the Bax-NPM complex, or a NPM inhibitor agent specifically reduces or eliminates cell death mediated by the Bax-NPM complex.

As used herein, an inhibitor of the formation of the Bax-NPM complex, or a NPM inhibitor agent has the ability to reduce the formation of the Bax-NPM complex in a cell (e.g., in a ischemic cell, e.g., a podocytes) by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or more, relative to the amount of Bax-NPM complex formed in the absence of the an inhibitor of the formation of the Bax-NPM complex, or a NPM inhibitor agent.

In some embodiments of the compositions and methods described herein, an agent which inhibits the formation of the Bax-NPM complex is a small molecule compound or agent that targets or binds to ischemic-induced phosphorylated form of the NPM polypeptide (i.e., having the phosphorylation status of one or more of pT86, pS88, pT95, nT234, nS242), including, but not limited to, small peptides or peptide-like molecules, soluble peptides, and synthetic non-peptidyl organic or inorganic compounds. As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Exemplary sites of small molecule binding include, but are not limited to, the portion of NPM polypeptide that binds to Bax, or portions of the NPM polypeptide comprising any one or more of T86, S88, T95, T234, S242, or bind to at least 5 amino acids anywhere within amino acids 78-103 of SEQ ID NO: 4 or bind to at least 5 amino acids anywhere within amino acids 226-246 of SEQ ID NO: 4.

In some embodiments of the compositions and methods described herein, an inhibitor of Bax-NPM complex formation comprises a small molecule that binds to the ischemic-induced phosphorylated form of the NPM polypeptide (i.e., having the phosphorylation status of one or more of pT86, pS88, pT95, nT234, nS242) and inhibits its biological activity.

In some embodiments of the compositions and methods described herein, the binding sites of an inhibitor of the formation of the Bax-NPM complex, or a NPM inhibitor agent, such as an antibody or antigen-binding fragment thereof, are directed against a NPM interaction site, such as its binding site with Bax. In some embodiments of the compositions and methods described herein, the binding sites of an inhibitor of the formation of the Bax-NPM complex, or a NPM inhibitor agent are directed against at least one of the stress-induced phosphorylation sites, e.g., any one or more of T86, S88, T95, T234, S242 on the NPM polypeptide of SEQ ID NO: 4, or a site in close proximity of these phosphorylation sites, in order to provide steric hindrance for the interaction of kinases, and/or phosphatases, or interaction with Bax. By binding to a Bax binding site, or to a region on the NPM polypeptide of SEQ ID NO: 4 that is confirmationally located close to one or more sites of T86, S88, T95, T234, S242 on SEQ ID NO: 4, an inhibitor of the formation of the Bax-NPM complex, or a NPM inhibitor agent described herein can reduce or inhibit the binding of the ischemic-induced phosphorylated form of the NPM polypeptide (i.e., having the phosphorylation status of one or more of pT86, pS88, pT95, nT234, nS242) to Bax, and downstream signaling consequences of the Bax-NPM complex. For example, in some embodiments of the compositions and methods described herein, the binding sites of an inhibitor of the formation of the Bax-NPM complex, or a NPM inhibitor agent block or target amino acids 78-103 of SEQ ID NO: 4 or amino acids 226-246 of SEQ ID NO: 4, and preferably both amino acids 78-103 of SEQ ID NO: 4 or amino acids 226-246 of SEQ ID NO: 4, i.e., NPM(78-103) and/or NPM(226-246) respectively of SEQ ID NO: 4, for example. This can be accomplished by a variety of means well known in the art, such as antibodies and antigen-binding fragments thereof, inhibitor RNAs, etc., and as described herein.

Accordingly, in some embodiments of the compositions and methods described herein, an inhibitor of the formation of the Bax-NPM complex, or a NPM inhibitor agent is an antibody or antigen-binding fragment thereof that selectively binds or physically interacts with the ischemic-induced phosphorylated form of the NPM polypeptide (i.e., having the phosphorylation status of one or more of pT86, pS88, pT95, nT234, nS242). In some embodiments of the compositions and methods described herein, an inhibitor of the formation of the Bax-NPM complex, or a NPM inhibitor agent is an antibody or antigen-binding fragment thereof that binds to the oligomeric form of the NPM polypeptide and inhibits and/or blocks and/or prevents interaction with Bax or Bax-NPM complex formation. In some embodiments of the compositions and methods described herein, the antibody or antigen-binding fragment thereof binds to the ischemic-induced phosphorylated form of the NPM polypeptide (i.e., having the phosphorylation status of one or more of pT86, pS88, pT95, nT234, nS242). In some embodiments of the compositions and methods described herein, the antibody or antigen-binding fragment thereof binds to the ischemic-induced phosphorylated form of the NPM polypeptide (i.e., having the phosphorylation status of one or more of pT86, pS88, pT95, nT234, nS242) can bind to block or target amino acids 78-103 of SEQ ID NO: 4 or amino acids 226-246 of SEQ ID NO: 4, and preferably both amino acids 78-103 of SEQ ID NO: 4 or amino acids 226-246 of SEQ ID NO: 4, i.e., NPM(78-103) and/or NPM(226-246) respectively of SEQ ID NO: 4. In some embodiments of the compositions and methods described herein, the antibody or antigen-binding fragment thereof binds to or blocks the Bax-NPM interaction. In some embodiments of the compositions and methods described herein, the antibody or antigen-binding fragment thereof binds to or blocks the Bax-binding site of NPM polypeptide.

Antibodies specific for or that selectively bind the ischemic-induced phosphorylated form of the NPM polypeptide (i.e., having the phosphorylation status of one or more of pT86, pS88, pT95, nT234, nS242) suitable for use in the compositions and for practicing the methods described herein are preferably monoclonal, and can include, but are not limited to, human, humanized or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain antigen or target binding sites or "antigen-binding fragments." The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art.

Accordingly, in some embodiments of the compositions and methods described herein, an inhibitor of the formation of the Bax-NPM complex, or a NPM inhibitor agent as described herein is a monoclonal anti-NPM antibody or antigen-binding fragment.

In some embodiments of the compositions and methods described herein, an inhibitor of the formation of the Bax-NPM complex, or a NPM inhibitor agent as described herein is an anti-NPM antibody fragment or antigen-binding fragment. In some embodiments, the anti-NPM antibody specifically binds to the ischemic-induced phosphorylated form of the NPM polypeptide (i.e., having the phosphorylation status of one or more of pT86, pS88, pT95, nT234, nS242) and does not bind to the normal NPM polypeptide (having a phosphorylation status of nT86, nS88, nT95, pT234, pS242). The terms "antibody fragment," "antigen binding fragment," and "antibody derivative" as used herein, refer to a protein fragment that comprises only a portion of an intact antibody, generally including an antigen binding site of the intact antibody and thus retaining the ability to bind antigen. Examples of antibody fragments encompassed by the terms antibody fragment or antigen-binding fragment include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having VH and $C_H1$ domains; (iv) the Fd' fragment having VH and $C_H1$ domains and one or more cysteine residues at the C-terminus of the $C_H1$ domain; (v) the Fv fragment having the VL and VH domains of a single arm of an antibody; (vi) a dAb fragment (Ward et al., Nature 341, 544-546 (1989)) which consists of a VH domain or a VL domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10):1057-1062 (1995); and U.S. Pat. No. 5,641,870); and modified versions of any of the foregoing (e.g., modified by the covalent attachment of polyalkylene glycol (e.g., polyethylene glycol, polypropylene glycol, polybutylene glycol) or other suitable polymer).

In some embodiments of the compositions and methods described herein, an inhibitor of the formation of the Bax-NPM complex, or a NPM inhibitor agent or antagonist is a chimeric antibody derivative of a an antibody that specifically binds to the ischemic-induced phosphorylated form of the NPM polypeptide (i.e., having the phosphorylation status of one or more of pT86, pS88, pT95, nT234, nS242) and does not bind to the normal NPM polypeptide (having a phosphorylation status of nT86, nS88, nT95, pT234, pS242) or antigen-binding fragment thereof. In some embodiments, an inhibitor of the formation of the Bax-NPM complex, or a NPM inhibitor agent or antagonist antibodies and antigen-binding fragments thereof described herein can also be, in some embodiments, a humanized antibody derivative.

In some embodiments, an inhibitor of the formation of the Bax-NPM complex, or a NPM inhibitor agent or antagonist antibodies and antigen-binding fragments thereof described herein include derivatives that are modified, i.e., by the covalent attachment of any type of molecule to the antibody, provided that the covalent attachment does not prevent the antibody from binding to the target antigen, e.g., the ischemic-induced phosphorylated form of the NPM polypeptide (i.e., having the phosphorylation status of one or more of pT86, pS88, pT95, nT234, nS242).

In some embodiments of the compositions and methods described herein, completely human antibodies are used, which are particularly desirable for the therapeutic treatment of human patients.

In some embodiments of the compositions and methods described herein, an inhibitor of the formation of the Bax-NPM complex, or a NPM inhibitor agent comprises at least one antisense molecule capable of blocking or decreasing the expression of a particular functional NPM polypeptide by targeting nucleic acids encoding NPM, or relevant domains thereof. In some embodiments of the compositions and methods described herein, the at least one antisense molecule targets nucleic acids encoding the Bax binding domain of the ischemic-induced phosphorylated form of the NPM polypeptide (i.e., having the phosphorylation status of one or more of pT86, pS88, pT95, nT234, nS242). In some embodiments of the compositions and methods described herein, the at least one antisense molecule targets nucleic acids encoding the Bax binding domain. Methods are known to those of ordinary skill in the art for the preparation of antisense oligonucleotide molecules that will specifically bind NPM mRNA without cross-reacting with other polynucleotides. Exemplary sites of targeting include, but are not limited to, the initiation codon, the 5' regulatory regions, including promoters or enhancers, the coding sequence, including any conserved consensus regions, and the 3' untranslated region. In some embodiment of these aspects and all such aspects described herein, the antisense oligonucleotides are about 10 to about 100 nucleotides in length, about 15 to about 50 nucleotides in length, about 18 to about 25 nucleotides in length, or more. In certain embodiments, the antisense oligonucleotides further comprise chemical modifications to increase nuclease resistance and the like, such as, for example, phosphorothioate linkages and 2'-O-sugar modifications known to those of ordinary skill in the art.

In some embodiments of the compositions and methods described herein, an inhibitor of the formation of the Bax-NPM complex, or a NPM inhibitor agent comprises at least one short interfering RNA (siRNA) molecule capable of blocking or decreasing the expression of functional NPM by targeting nucleic acids encoding SEQ ID NO: 4 (e.g., SEQ ID NO: 7), or relevant domains thereof. In some embodiments of the compositions and methods described herein, the at least one siRNA molecule targets nucleic acids encoding the Bax binding domain of NPM.

In some embodiments of the compositions and methods described herein, the at least one siRNA molecule targets nucleic acids encoding the Bax binding domain of NPM polypeptide. In some embodiments of the compositions and methods described herein, the at least one siRNA molecule targets nucleic acids encoding the regions of the NPM polypeptide comprising at least one or more of amino acids T86, S88, T95, T234, S242. It is routine to prepare siRNA molecules that will specifically target NPM mRNA without cross-reacting with other polynucleotides. siRNA molecules for use in the compositions and methods described herein can be generated by methods known in the art, such as by typical solid phase oligonucleotide synthesis, and often will incorporate chemical modifications to increase half-life and/or efficacy of the siRNA agent, and/or to allow for a more robust delivery formulation. Alternatively, siRNA molecules are delivered using a vector encoding an expression cassette for intracellular transcription of siRNA.

In some embodiments of the compositions and methods described herein, a RNA or DNA aptamer binds to or physically interacts with the ischemic-induced phosphorylated form of the NPM polypeptide (i.e., having the phosphorylation status of one or more of pT86, pS88, pT95, nT234, nS242), i.e., NPM (78-103) of SEQ ID NO: 4 or NPM(226-246) of SEQ ID NO: 4. In some embodiments of the compositions and methods described herein, the RNA or DNA aptamer binds to or physically interacts with or blocks the ichemic-induced phosphorylated form of the NPM polypeptide from binding to Bax.

In some embodiments of the compositions and methods described herein, an inhibitor of Bax-NPM complex formation comprises at least one NPM structural analog, such as a dominant negative NPM polypeptide. In some embodiments of the compositions and methods described herein, an inhibitor of Bax-NPM complex formation comprises at least one soluble NPM peptide or fusion polypeptide thereof, such as, for example, a NPM inhibitory polypeptide. In some such embodiments, the NPM inhibitory polypeptide is a dominant negative NPM fusion protein. In some embodiments of the compositions and methods described herein, the NPM inhibitory polypeptide comprises amino acids 78-103 of SEQ ID NO: 4 or amino acids 226-246 of SEQ ID NO: 4 of variants having at least 50%, or 60%, or at least 70%, or at least 80%, or at least 90% or at least 95% or at least 98% sequence identity thereto.

An inhibitor of Bax-NPM complex formation or a NPM peptide inhibitor, as described herein, for use in the compositions and methods described herein can be identified or characterized using methods known in the art, such as protein-protein binding assays, biochemical screening assays, immunoassays, and cell-based assays, which are well known in the art, including, but not limited to, those described herein in the Examples.

Such identified inhibitors of Bax-NPM complex formation or a NPM peptide inhibitors s can further be tested using in vivo animal models of chronic kidney disease, such as glomerular and interstitial injury models (e.g., animal models of lupus nephritis, including mice of the NZB, (NZB× NZW) F1 hybrid (termed NZB/W), and congenic derivatives thereof, MRL/lpr and BXSB strains), animal models of aging (e.g., aged Sprague Dawley rats and aged C57BL/6 mice); spontaneously hypertensive rats (SHR); Buffalo/mna rats, which are a model of human idiopathic nephrotic syndrome; Munich Wistar Fromter (MWF) rats, which are a genetic model related to a congenital deficit in nephron number being predisposed to the development of hypertension and salt sensitivity in adulthood; primary podocyte-specific genetic FSGS models; HIV-associated nephropathy (HIVAN) transgenic mouse models; animal models of Alport syndrome, which comprise mutations of the α3, α4, or α5 chains of type IV collagen (COL4A3, COL4A4, and COL4A5); immune-induced models, such as the Thy-1 nephritis model, which is an experimental rat model of mesangioproliferative glomerulonephritis (MsPGN), anti-glomerular basement membrane (GBM) models; and non-immune induced models.

One aspect of the technology described herein relates to a method to treat a subject any of: acute kidney injury (AKI) or ischemia, comprising administering a subject a composition comprising at least one peptide selected from the group consisting of: TVTIFVAGVLTASLTIWKKMG (SEQ ID NO: 1); TLKMSVQPTVSLGGFEITPPVVLRLK (peptide #2) (SEQ ID NO: 2) and ESFKKQEKTPKTPKGPSSVEDIKAK (peptide #3) (SEQ ID NO: 3), or a peptide with at least 85% or 90% or 95% sequence identity to any of SEQ ID NO: 1-3. In some embodiments, the peptides of SEQ ID NO: 1-3 are conjugated or attached to renal targeting moieties or peptides, including renal targeting nuclear localization sequences (NLS), so the peptides target the kidney.

Accordingly, in some aspects, provided herein are methods for the treatment of chronic kidney disease in a subject in need thereof, such method comprising administering to a subject having or at risk for a kidney disease, including chronic kidney disease a therapeutically effective amount of a composition comprising a NPM peptide.

Also provided herein, in some aspects, are methods for the reduction of proteinuria in a subject in need thereof, comprising administering to a subject having or at risk for proteinuria a therapeutically effective amount of a composition comprising a NPM peptide. In other aspects, provided herein are methods for preventing kidney diseases or promoting prophylaxis of kidney diseases in a subject in need thereof, comprising administering to a subject a therapeutically effective amount of a composition comprising a NPM peptide so as to prevent or promote prophylaxis of kidney disease in the subject.

Also provided herein, in some aspects, are methods for mitigating the effects of kidney disease, reducing the severity of kidney disease, reducing the likelihood of developing kidney disease and/or slowing the progression of kidney disease in a subject in need thereof.

Accordingly, in some embodiments of the methods described herein, an effective amount of a composition comprising an inhibitor of Bax-NPM complex formation or a NPM peptide inhibitor, as described herein is administered to a subject in order to alleviate a symptom of chronic kidney disease. As used herein, "alleviating a symptom chronic kidney disease" is ameliorating any condition or symptom associated with the chronic kidney disease. Alternatively, alleviating a symptom of a chronic kidney disease can involve reducing one or more symptoms of the chronic kidney disease in the subject relative to an untreated control suffering from chronic kidney disease or relative to the subject prior to the treatment. As compared with an equivalent untreated control, or the subject prior to the treatment with an inhibitor of Bax-NPM complex formation or a NPM peptide inhibitor, as described herein, such reduction or degree of prevention is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more, as measured by any standard technique. Desirably, the chronic kidney disease is significantly reduced or undetectable, as detected by any standard method known in the art, in which case the chronic kidney disease is considered to have been treated. A patient who is being treated for a chronic kidney disease is one who a medical practitioner has diagnosed as having such a condition. Diagnosis can be by any suitable means known to one of ordinary skill in the art. Diagnosis and monitoring can involve, for example, detecting the level of specific proteins or molecules in a urine, blood, or serum sample, such as, for example, albumin, calcium, cholesterol, complete blood count (CBC), electrolytes, magnesium, phosphorous, potassium, sodium, or any combination thereof; assays to detect, for example, creatinine clearance; creatinine levels; BUN (blood urea nitrogen); through the use of specific techniques or procedures, such as an abdominal CT scan, abdominal MRI, abdominal ultrasound, kidney biopsy, kidney scan, kidney ultrasound; via detection of changes in results of assays or tests for erythropoietin, PTH; bone density test, or Vitamin D; or any combination of such detection methods and assays.

A. NPM Peptide Inhibitors for Treatment of Kidney Injury, AKI and Ischemia

Accordingly, one aspect of the technology described herein relates to a method to treat a subject any of: acute kidney injury (AKI) or ischemia, comprising administering a subject a composition comprising an agent that blocks Bax from interacting with the ischemic-induced phosphorylated form of the NPM polypeptide (i.e., having the phosphorylation status of one or more of pT86, pS88, pT95, nT234, nS242.

In some embodiments, the agent is a NPM inhibitory peptide, e.g., a peptide or fragment from SEQ ID NO: 4. In some embodiments, a NPM inhibitory peptide does not inhibit the oligomeric form of NPM polypeptide. In some embodiments, a NPM inhibitory peptide specifically inhibits the monomeric form of NPM polypeptide that binds or complexes with Bax.

In some embodiments, a NPM peptide is selected from a peptide comprising any of: TVTIFVAGVL-TASLTIWKKMG (SEQ ID NO: 1); TLKMSVQPTVSLGGFEITPPVVLRLK (peptide #2) (SEQ ID NO: 2) and ESFKKQEKTPKTPKGPSSVEDIKAK (peptide #3) (SEQ ID NO: 3), or a peptide with at least 85% or 90% or 95% sequence identity to any of SEQ ID NO: 1-3.

In some embodiments, a NPM inhibitory peptide comprises an amino acid sequence having at least 50% amino acid identity, at least 55% identity, at least 60% identity, at least 65% identity, at least 70% identity, at least 75% identity, at least 80% identity, preferably at least 85% identity, at least 90% identity, at least 95% amino acid identity, at least 96% amino acid identity, at least 97% amino acid identity, at least 98% amino acid identity, or at least 99% amino acid sequence identity to any of SEQ ID NO: 1 or SEQ ID NO: 2 or SEQ ID NO: 3. In some embodiments, a NPM inhibitory peptide comprises an amino acid sequence having at least 70% identity, at least 75% identity, at least 80% identity, preferably at least 85% identity, at least 90% identity, at least 95% amino acid identity, at least 96% amino acid identity, at least 97% amino acid identity, at least 98% amino acid identity, or at least 99% amino acid sequence identity to any of SEQ ID NO: 1 or SEQ ID NO: 2 or SEQ ID NO: 3, and having at least a 80% of the biological activity of SEQ ID NO: 1 or SEQ ID NO: 2 or SEQ ID NO: 3, respectively, with respect to inhibiting the Bax-NPM complex formation, or treating or preventing AKI-mediated effects in a mouse model in vivo (see, the methods described in the Examples herein and FIG. 8).

In some embodiments, a NPM inhibitory peptide comprises amino acids 78-103 of SEQ ID NO: 4, or amino acids 226-246 of SEQ ID NO: 4, or a fragment or variant with at least 85% or 90% or 95% sequence identify thereto.

In some embodiments, a NPM inhibitory peptide comprises a fragment of the NPM polypepide comprising any one or more of the phosphorylation sites of T86, S88, T95, T234 or S242. In some embodiments, a NPM inhibitory peptide comprises at least consecutive 10 amino acids selected from any of amino acids 1-50, 40-60, 60-80, 60-120, 130-200, 200-250, 220-250 of SEQ ID NO: 4. In some embodiments, if the NPM inhibitor peptide comprises any one of amino acids T86, S88, T95 of SEQ ID NO: 4, then each can exist as the phosphorylated forms (i.e., pT86, pS88, pT95). In alternative embodiments, if the NPM inhibitor peptide comprises any one of amino acids T86, S88, T95 of SEQ ID NO: 4, then each the can exist as the nonphosphorylated forms (i.e., nT86, nS88, nT95). In some embodiments, if the NPM inhibitor peptide comprises any one of amino acids T234 or S242 of SEQ ID NO: 4, then the can each exist as the non-phosphorylated forms (i.e., nT234 or nS242). In alternative embodiments, if the NPM inhibitor peptide comprises any one of amino acids T234 or S242 of SEQ ID NO: 4, then the can each exist as the phosphorylated forms (i.e., pT234 or pS242). It is envisioned that if an NPM inhibitory peptide comprises more than one phosphorylation amino acid of T86, S88, T95, T234 or S242, the NPM inhibitory peptide can comprise any combination of phosphorulation states.

In some embodiments of the compositions and methods described herein, an inhibitor of Bax-NPM complex formation comprises at least one NPM structural analog, such as a dominant negative NPM peptide. Exemplary dominant negative NPM peptides are NPM (78-103) of SEQ ID NO: 4 or NPM(226-246) of SEQ ID NO: 4. In some embodiments, amino acids T86, S88 and T95 of a NPM(78-103) peptide are phosphorylated. In some embodiments, amino acids T234 or S242 of a NPM(226-246) peptide are non-phosphorylated. In some embodiments of the compositions and methods described herein, the RNA or DNA aptamer binds to or physically interacts with or blocks the ichemic-induced phosphorylated form of the NPM polypeptide from binding to Bax.

In some embodiments of the compositions and methods described herein, an inhibitor of Bax-NPM complex formation comprises at least one soluble NPM peptide or fusion polypeptide thereof, such as, for example, a NPM inhibitory polypeptide. In some such embodiments, the NPM inhibitory polypeptide is a dominant negative NPM fusion protein. In some embodiments of the compositions and methods described herein, the NPM inhibitory polypeptide comprises amino acids 78-103 of SEQ ID NO: 4 or amino acids 226-246 of SEQ ID NO: 4 of variants having at least 50%, or 60%, or at least 70%, or at least 80%, or at least 90% or at least 95% or at least 98% sequence identity thereto.

B. Modifications of NPM Peptide Inhibitors

In some embodiments, a NPM inhibitory peptides of SEQ ID NO: 1-3 are conjugated or attached to renal targeting moieties or peptides, including renal targeting nuclear localization sequences (NLS), so the peptides target the kidney. In some embodiments, a NPM peptide mimic further comprises a targeting sequence selected from the group consisting of: Ac-KKKRKV-(βA) (SEQ ID NO: 5), and AC-PKKKRKV-(βA) (SEQ ID NO: 6), or a variant at least 85% or at least 90% or at least 95% sequence identity to SEQ ID NO: 5 or 6. In some embodiments, the NPM inhibiting peptide can comprise a cell penetrating peptide (referred to herein as "CPP") as disclosed in the Examples. Any CPP commonly known in the art is envisioned for use, for example exemplary CPPs are disclosed in US patent and patent applications U.S. Pat. Nos. 7,579,318; 8,242,081; 8,372,951; 8,575,305; 8,044,019; 2008/0234183, 2003/0229202; 2013/0164219, each of which are incorporated herein in their entirety by reference.

A NPM inhibitory peptide disclosed herein, e.g. SEQ ID NO: 1-3 as disclosed herein, may be synthesized by methods familiar to those skilled in the art or purchased commercially (#CG51068 RayBiotech, Inc. Norcross, Ga.).

Variations and modifications to a NPM inhibitory peptide can are envisioned to provide means for targeting. For example, a NPM inhibitory peptide as disclosed herein, can be linked with a molecular counter-ligand, for example but not limited to, molecules which target the kidney, to make a NPM inhibitory peptide tissue specific.

In one embodiment, a NPM inhibitory peptide as disclosed herein is linked to a carrier to enhance its bioavailability. Such carriers are known in the art and include poly (alkyl) glycol such as poly ethylene glycol (PEG) or methoxypolyethylene glycol (mPEG) which can increase the in vivo half life of proteins to which they are conjugated. Methods of PEGylation of a peptide are well known by one of ordinary skill in the art, and are considerations of, for example, how large a PEG polymer to use. In some embodiments, a peptide can be fused to serum albumin to increase the serum half-life of therapeutic polypeptides and peptides.

It will be appreciated that a NPM inhibitory peptide as disclosed herein, useful in the methods and composition as disclosed herein can optionally contain amino acids other than the 20 amino acids commonly referred to as the 20 naturally occurring amino acids.

In some embodiments, any of the amino acids of a NPM inhibitory peptide as disclosed herein, such as SEQ ID NO: 1-3 or a peptide having at least 80% sequence identity thereto, including the terminal amino acids, can be modified either by natural processes such as glycosylation and other posttranslational modifications, or by chemical modification techniques which are well known in the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which can be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, 1. E. Creighton, Proteins-Structure and Molecular Properties, 2nd Ed., W.H. Freeman and Company, New York, 1993. Many detailed reviews are available on this subject, such as, for example, those provided by Wold, F., in Posttranslational Covalent Modification of Proteins, B. C. Johnson, Ed., Academic Press, New York, pp 1-12, 1983; Sifter et al., Meth. Enzymol. 182: 626-646, 1990 and Rattan et al., Protein Synthesis: Posttranslational Modifications and Aging, Ann. N.Y. Acad. Sci. 663: 48-62, 1992.

It will also be appreciated, as is well known and as noted above, that peptides and polypeptides are not always entirely linear. For instance, polypeptides can be branched as a result of ubiquitination, and they can be circular, with or without branching, generally as a result of posttranslational events, including natural processing events and events brought about by human manipulation which do not occur naturally. Circular, branched and branched circular polypeptides can be synthesized by non translational natural processes and by entirely synthetic methods.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and; synthetic polypeptides and such modifications can be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylation host, generally a eukaryotic cell. Insect cells often carry out the same posttranslational glycosylation as mammalian cells and, for this reason, insect cell expression systems have been developed to efficiently express mammalian proteins having native patterns of glycosylation, inter alia. Similar considerations apply to other modifications.

It will be appreciated that the same type of modification can be present to the same or varying degree at several sites in a given polypeptide. Also, a given peptide or polypeptide can contain many types of modifications.

In some embodiments, N-methyl and hydroxy-amino acids can be substituted for conventional amino acids in solid phase peptide synthesis. However, production of polymers with reduced peptide bonds requires synthesis of the dimmer of amino acids containing the reduced peptide bond. Such dimers are incorporated into polymers using standard solid phase synthesis procedures. Other synthesis procedures are well known in the art.

Accordingly, functional derivatives of a NPM inhibitory peptide as disclosed herein, may be prepared by modification of the amino acids of SEQ ID NO: 1-3e are encompassed for use in the methods and compositions as disclosed herein. Modifications may occur anywhere in the NPM inhibitory peptide as disclosed herein, e.g., a modification of any amino acid in the sequences of any of SEQ ID NO; 1, SEQ ID NO: 2 or SEQ ID NO: 3 or its functional derivative polypeptide, including the peptide backbone, the amino acid side-chains and the amino or carboxyl termini. Modifications may include, for example, acetylation, acylation, ADP-ribosylation, amidation, covalent attachment of other functional moiety, covalent attachment of a lipid or lipid derivative, covalent attachment of phosphotidylinositol, cross-linking, cyclization, disulfide bond formation, demethylation, formation of covalent cross-links, formylation, gamma-carboxylation, glycosylation, glycophosphatidylinositol (GPI) anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. See, for instance, E. Creighton Proteins-Structure and Molecular Properties, 2nd Ed., W. H. Freeman and Company, New York (1993); B. C. Johnson, Post Translational Covalent Modification of Proteins, Academic Press, New York, (1983); Seifter et al., Meth. Enzymol. 182: 626-646 (1990); Rattan et al., Ann. N.Y. Acad. Sci. 663: 48-62 (1992). Preparation of these modified derivatives may, for example, be useful if direct administration of the GHK peptide is contemplated.

In some embodiments a NPM inhibitory peptide as disclosed herein, can be conjugated to a second entity, for example, to promote stability or for specific cell type targeting. In some embodiments, a NPM inhibitory peptide as disclosed herein, or fragments, derivatives or variants thereof can be conjugated to a first fusion partner (i.e. IgG1 Fc). The conjugation can be a non-covalent or covalent interaction, for example, by means of chemical crosslinkage or conjugation. As discussed herein, in some embodiments, a NPM inhibitory peptide as disclosed herein, is fused to serum albumin to increase the serum half-life of the a NPM inhibitory peptide, e.g., SEQ ID NO: 1-3.

In some embodiments, a NPM inhibitory peptide as disclosed herein, can also be fused to a second fusion partner, for example, to a polypeptide that targets the product to a desired location, or, for example, a tag that facilitates its purification, if so desired. Tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use.

As used herein, the term "conjugate" or "conjugation" refers to the attachment of two or more entities to form one entity. For example, the methods of the present invention provide conjugation of a NPM inhibitory peptide as disclosed herein, or fragments, derivatives or variants thereof joined with another entity, for example a moiety such as a first fusion partner that makes the NPM inhibitory peptide stable, such as Ig carrier particle, for example IgG1 Fc. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention.

According to the present invention, a NPM inhibitory peptide as disclosed herein, or fragments, derivatives or variants thereof, can be linked to the first fusion partner via any suitable means, as known in the art, see for example U.S. Pat. Nos. 4,625,014, 5,057,301 and 5,514,363, which are incorporated herein in their entirety by reference. For example, the GHK peptide e can be covalently conjugated to the IgG1 Fc, either directly or through one or more linkers. In one embodiment, a NPM inhibitory peptide as disclosed herein is conjugated directly to the first fusion partner (e.g. Fc), and in an alternative embodiment, a NPM inhibitory peptide as disclosed herein can be conjugated to a first fusion partner (such as IgG1 Fc) via a linker, e.g. a transport enhancing linker.

A large variety of methods for conjugation of a NPM inhibitory peptide as disclosed herein, with a first fusion partner (e.g. Fc) are known in the art. Such methods are e.g. described by Hermanson (1996, Bioconjugate Techniques, Academic Press), in U.S. Pat. Nos. 6,180,084 and 6,264,914 which are incorporated herein in their entirety by reference and include e.g. methods used to link haptens to carriers proteins as routinely used in applied immunology (see Harlow and Lane, 1988, "Antibodies: A laboratory manual", Cold Spring Harbor Laboratory Press, Cold Spring Harbor, N.Y.). It is recognized that, in some cases, a NPM inhibitory peptide as disclosed herein can lose efficacy or functionality upon conjugation depending, e.g., on the conjugation procedure or the chemical group utilized therein. However, given the large variety of methods for conjugation the skilled person is able to find a conjugation method that does not or least affects the efficacy or functionality of the entities, such as the NPM inhibitory peptide to be conjugated.

Suitable methods for conjugation of a NPM inhibitory peptide as disclosed herein with a first fusion partner (e.g. Fc) include e.g. carbodimide conjugation (Bauminger and Wilchek, 1980, Meth. Enzymol. 70: 151-159). Alternatively, a moiety can be coupled to a targeting agent as described by Nagy et al., Proc. Natl. Acad. Sci. USA 93:7269-7273 (1996), and Nagy et al., Proc. Natl. Acad. Sci. USA 95:1794-1799 (1998), each of which are incorporated herein by reference. Another method for conjugating one can use is, for example sodium periodate oxidation followed by reductive alkylation of appropriate reactants and glutaraldehyde crosslinking.

One can use a variety of different linkers to conjugate a NPM inhibitory peptide as disclosed herein, with a first fusion partner (e.g. Fc), for example but not limited to aminocaproic horse radish peroxidase (HRP) or a heterobiofunctional cross-linker, e.g. carbonyl reactive and sulfhydryl-reactive cross-linker Heterobiofunctional cross linking reagents usually contain two reactive groups that can be coupled to two different function targets on proteins and other macromolecules in a two or three-step process, which can limit the degree of polymerization often associated with using homobiofunctional cross-linkers. Such multi-step protocols can offer a great control of conjugate size and the molar ratio of components.

The term "linker" refers to any means to join two or more entities, for example a NPM inhibitory peptide as disclosed herein, with a first fusion partner (e.g. Fc). A linker can be a covalent linker or a non-covalent linker Examples of covalent linkers include covalent bonds or a linker moiety covalently attached to one or more of the proteins to be linked. The linker can also be a non-covalent bond, e.g. an organometallic bond through a metal center such as platinum atom. For covalent linkages, various functionalities can be used, such as amide groups, including carbonic acid derivatives, ethers, esters, including organic and inorganic esters, amino, urethane, urea and the like. To provide for linking, the effector molecule and/or the probe can be modified by oxidation, hydroxylation, substitution, reduction etc. to provide a site for coupling. It will be appreciated that modification which do not significantly decrease the function of the a NPM inhibitory peptide as disclosed herein or the first fusion partner (e.g. Fc) are preferred.

The dosage ranges for the administration of a NPM inhibitory peptide as disclosed herein, e.g., a peptide of SEQ ID NO: 1-3 or a peptide with at least 80% sequence identity thereto depend upon the form of the protein, and its potency, as described further herein, and are amounts large enough to produce the desired effect in which the symptoms, markers, or signs of kidney disease or AKI are reduced. The dosage should not be so large as to cause adverse side effects. Generally, the dosage can vary with the age, condition, and sex of the patient and can be determined by one of skill in the art. The dosage can also be adjusted by the individual physician in the event of any complication. Typically, the dosage ranges from 0.001 mg/kg body weight to 1000 mg/kg body weight. In one embodiment, the dose range is from 0.5 µg/kg body weight to 25 mg/kg body weight. The doses can be given once a day, less than once a day or multiple times a day in order to achieve a therapeutically effective dose.

With respect to the therapeutic methods of the invention, it is not intended that the administration of a NPM inhibitory peptide as disclosed herein, be limited to a particular mode of administration, dosage, or frequency of dosing; the present invention contemplates all modes of administration, including intramuscular, intravenous, inhalation, intraperitoneal, intravesicular, intraarticular, intralesional, subcutaneous, or any other route sufficient to provide a dose adequate to treat the ischemic injury and/or kidney injury or AKI. The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, therapeutically effective amounts of a NPM inhibitory peptide as disclosed herein, can be provided at a dose of 0.0001, 0.01, 0.01 0.1, 1, 5, 10, 25, 50, 100, 500, or 1,000 mg/kg. Effective doses may be extrapolated from dose-response curves derived from in vitro or animal model test bioassays or systems.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the NPM inhibitory peptide as disclosed herein, or functional derivatives thereof, and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising a NPM inhibitory peptide as disclosed herein, or functional derivatives thereof are optionally tested in one or more appropriate in vitro and/or in vivo animal models of disease, such as mice exposed to cigarette smoke (Shapiro Chest 2000 117:2235-75), to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the NPM inhibitory peptide as disclosed herein, or functional derivatives thereof at various concentrations, e.g., as applied to the mass and overall health of the patient. Administration can be accomplished via single or divided doses.

In determining the effective amount of a NPM inhibitory peptide as disclosed herein, or functional derivatives thereof to be administered in the treatment or prophylaxis of disease the physician evaluates circulating plasma levels, formulation toxicities, and progression of the disease.

C. Pharmaceutical Compositions and Modes of Administration

An inhibitor of Bax-NPM complex formation or a NPM peptide inhibitor, as described herein can be administered to a subject in need thereof by any appropriate route which results in an effective treatment in the subject. As used herein, the terms "administering," and "introducing" are used interchangeably and refer to the placement of an inhibitor of Bax-NPM complex formation or a NPM peptide inhibitor, as described herein into a subject by a method or route which results in at least partial localization of such agents at a desired site, such that a desired effect(s) is produced.

In some embodiments, an inhibitor of Bax-NPM complex formation or a NPM peptide inhibitor, as described herein is administered to a subject having a chronic kidney disease by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, an inhibitor of Bax-NPM complex formation or a NPM peptide inhibitor, as described herein for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of an inhibitor of Bax-NPM complex formation or a NPM peptide inhibitor, as described herein, other than directly into a target site, tissue, or organ, such as a tumor site, such that it enters the subject's circulatory system and, thus, is subject to metabolism and other like processes.

For the clinical use of the methods described herein, administration of an inhibitor of Bax-NPM complex formation or a NPM peptide inhibitor, as described herein, can include formulation into pharmaceutical compositions or pharmaceutical formulations for parenteral administration, e.g., intravenous; mucosal, e.g., intranasal; ocular, or other mode of administration. In some embodiments, an inhibitor of Bax-NPM complex formation or a NPM peptide inhibitor, as described herein can be administered along with any pharmaceutically acceptable carrier compound, material, or composition which results in an effective treatment in the subject. Thus, a pharmaceutical formulation for use in the methods described herein can contain an inhibitor of Bax-NPM complex formation or a NPM peptide inhibitor, as described herein, as described herein, in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an inhibitor of Bax-NPM complex formation or a NPM peptide inhibitor, as described herein. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

An inhibitor of Bax-NPM complex formation or a NPM peptide inhibitor, as described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, an inhibitor of Bax-NPM complex formation or a NPM peptide inhibitor, as described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

In some embodiments, an inhibitor of Bax-NPM complex formation or a NPM peptide inhibitor as disclosed herein is administered within 48 hrs of an ischemic insult or injury, or within 36 hours, or 24 hours, or 12 hrs, or within 6 hours of an ischemic insult or injury. In some embodiments, an inhibitor of Bax-NPM complex formation or a NPM peptide inhibitor as disclosed herein is administered within 0-3 hours, or 0-6 hours of an ischemic insult or injury, or within 6-12 hrs, or 12-24 hrs of an ischemic injury or insult.

Further embodiments of the formulations and modes of administration of the compositions comprising an inhibitor of Bax-NPM complex formation or a NPM peptide inhibitor, as described herein, that can be used in the methods described herein are described below.

Parenteral Dosage Forms.

Parenteral dosage forms of an inhibitor of Bax-NPM complex formation or a NPM peptide inhibitor, as described herein can also be administered to a subject with a chronic kidney condition by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments, compositions comprising an effective amount of an inhibitor of Bax-NPM complex formation or a NPM peptide inhibitor, as described herein are formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary. In some embodiments, oral dosage forms are not used for the antibiotic agent.

Typical oral dosage forms of the compositions comprising an effective amount of an inhibitor of Bax-NPM complex formation or a NPM peptide inhibitor, as described herein are prepared by combining the pharmaceutically acceptable salt of the inhibitor of Bax-NPM complex formation or the NPM peptide inhibitor, as described herein in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Binders suitable for use in the pharmaceutical formulations described herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical formulations described herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions described herein is typically present in from about 50 to about 99 weight percent of the pharmaceutical composition.

Disintegrants are used in the oral pharmaceutical formulations described herein to provide tablets that disintegrate when exposed to an aqueous environment. A sufficient amount of disintegrant that is neither too little nor too much to detrimentally alter the release of the active ingredient(s) should be used to form solid oral dosage forms of an inhibitor of Bax-NPM complex formation or a NPM peptide inhibitor, as described herein. The amount of disintegrant used varies based upon the type of formulation, and is readily discernible to those of ordinary skill in the art. Disintegrants that can be used to form oral pharmaceutical formulations include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form oral pharmaceutical formulations of an inhibitor of Bax-NPM complex formation or a NPM peptide inhibitor, as described herein, include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In other embodiments, lactose-free pharmaceutical formulations and dosage forms are provided, wherein such compositions preferably contain little, if any, lactose or other mono- or di-saccharides. As used herein, the term "lactose-free" means that the amount of lactose present, if any, is insufficient to substantially increase the degradation rate of an active ingredient. Lactose-free compositions of the disclosure can comprise excipients which are well known in the art and are listed in the USP (XXI)/NF (XVI), which is incorporated herein by reference.

The oral formulations of an inhibitor of Bax-NPM complex formation or a NPM peptide inhibitor, as described herein further encompass, in some embodiments, anhydrous pharmaceutical compositions and dosage forms comprising the ROBO2 inhibitors described herein as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Aerosol Formulations.

An inhibitor of Bax-NPM complex formation or a NPM peptide inhibitor, as described herein can be packaged in a pressurized aerosol container together with suitable propellants, for example, hydrocarbon propellants like propane, butane, or isobutane with conventional adjuvants. An inhibitor of Bax-NPM complex formation or a NPM peptide inhibitor, as described herein can also be administered in a non-pressurized form such as in a nebulizer or atomizer. An inhibitor of Bax-NPM complex formation or a NPM peptide inhibitor, as described herein inhibitor can also be administered directly to the airways in the form of a dry powder, for example, by use of an inhaler.

Suitable powder compositions include, by way of illustration, powdered preparations of an inhibitor of Bax-NPM complex formation or a NPM peptide inhibitor, as described herein, thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S, and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of an inhibitor of Bax-NPM complex formation or a NPM peptide inhibitor, as described herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms.

In some embodiments of the aspects described herein, an inhibitor of Bax-NPM complex formation or a NPM peptide inhibitor, as described herein can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the ROBO-2 inhibitors described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUO-LITE® A568 and DUOLITE® AP143 (Rohm & Haas, Spring House, Pa. USA).

In some embodiments of the methods described herein, an inhibitor of Bax-NPM complex formation or a NPM peptide inhibitor, as described herein for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has chronic kidney disease. Each pulse dose can be reduced and the total amount of a ROBO-2 inhibitor described herein administered over the course of treatment to the subject or patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In some embodiments, sustained-release preparations comprising an inhibitor of Bax-NPM complex formation or a NPM peptide inhibitor, as described herein can be prepared. Suitable examples of sustained-release preparations include semipermeable matrices of solid hydrophobic polymers containing the inhibitor, in which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid.

The formulations comprising an inhibitor of Bax-NPM complex formation or a NPM peptide inhibitor, as described herein to be used for in vivo administration are preferably sterile. This is readily accomplished by filtration through, for example, sterile filtration membranes, and other methods known to one of skill in the art.

IV. Diagnostic Assays for Detection of AKI

In one aspect, the invention provides for methods, compositions and kits for detecting ischemic-stress induced phosphorylation status of NPM. In particular, one aspect relates to a diagnostic assay, method and composition to assess if a subject has AKI, wherein the method comprises assessing the phosphorylation status of the NPM polypeptide, and detecting a change of at least one of the phosphorylation sites as follows: T86, S88, T95, T234 or S242. In particular, under normal conditions (e.g., non-stress conditions) T86, S88, T95 of the NPM polypeptide are unphosphorylated, and become phosphorylated under stressful conditions to become phospho-T86, phospho-S88, phospho-T95. In contrast, under normal conditions (e.g., non-stress conditions) T234 and S242 of the NPM polypeptide are phosphorylated, and become dephosphorylated under stressful conditions. That is, under normal conditions, the phosphorylation state of the NPM polypeptide is T86, S88, T95, phospho-T234, phospho-S242, and under stressful conditions, or after AKI, the phosphorylation state of the NPM polypeptide is phospho-T86, phospho-S88, phospho-T95, T234, S242.

Accordingly, in some embodiments, an assay can comprise a method to detect at least one or more of: phospho-T86, phospho-S88, phospho-T95, unphosporylated-T234 and unphosporylated-S242 of a NPM polypeptide in a biological sample obtained from a subject, wherein detection of at least one, or at least 2, or at least 3 or at least 4 of the above phosphorylation states of NPM polypeptide identifies a subject with kidney injury or AKI. Detection of the phosphorylation states can be by any means, e.g., mass spectrometry, antibodies or antibody fragments, including but not limited to, pan-specific phospho-Ser (anti-pSer) or phospho-Thr (anti-pThr) antibodies, as well as phospho-specific antibodies, e.g., anti-phospho-T86, anti-phospho-S88, anti-phospho-T95, anti-phospho-T234 and anti-phospho-S242 antibodies, or antibody fragments or antigen binding fragments thereof.

Exemplary biological samples include, but are not limited to, a kidney biopsy sample, serum, blood, plasma and urine. Additionally, the inventors have also discovered that interruption of the stress-induced NPM phosphorylation events, e.g., using one of three different blocking peptides, can decrease cell death in the kidney due to metabolic stress (including ischemic stress and hypoxic stress), and can be used as treatment, including therapeutic treatment to treat a subject with AKI, or alternatively, as a prophylactic treatment to prevent the subject developing AKI.

A. Stress- and Ischemia-Induced Phosphorylation States of NPM

In one aspect, the invention provides a method for diagnosing kidney injury, e.g., acute kidney injury (AKI) in a subject by measuring the ischemic-induced, or stress-induced phosphorylation of NPM polypeptide in a biological sample, e.g., a blood sample or urine sample obtained from the subject. As discussed herein, under normal (non-stressful) conditions, the phosphorylation state of the NPM polypeptide is T86, S88, T95, phospho-T234, phospho-S242. In contrast, under stressful conditions, or after AKI, the phosphorylation state of the NPM polypeptide changes to phospho-T86, phospho-S88, phospho-T95, T234, S242. That is, after ischemic or hypoxic stress, one or more of amino acid residues T86, S88, T95 of the NPM polypeptide become phosphorylated, and one or both of phospho-T234, phospho-S242 on the NPM polypeptide become dephosphorylated (to T234 and S242). It is envisioned that not all these phosphorylation events necessarily occur under ischemic or stress-induced conditions as described herein in the Examples, and therefore, in some embodiments, at least 2, or at least 3, or at least 4 or at least 5 of the phosphorylation events can be measured.

For simplicity purposes herein, non-phosphorylated Ser or Thr residues are represented as nS or nT respectively. Therefore, the stress-induced phosphorylation status of NPM can be represented as having at least 1 or at least 2, or at least 3, or at least 4 or at least 5 of the following phosphorylation states: pT86, pS88, pT95, nT234, nS242, and the under normal conditions, the phosphorylation status of NPM can be represented as having at least 1 or at least 2, or at least 3, or at least 4 or at least 5 of the following phosphorylation states nT86, nS88, nT95, pT234, pS242.

In some embodiments, one can measure at least one, or at least 2 or at least 3, or at least 4 or at least all 5 phosphorylation changes, e.g., at least one, or at least 2 or at least 3, or at least 4 or at least all 5 phosphorylation changes of T86 to pT86, S88 to pS88, T95 to pT95, pT234 to T234, pS242 to S242.

In some embodiments, one can measure at least one, or at least 2 or all three of: T86 to pT86, S88 to pS88, T95 to pT95, and also measure at least one of pT234 to T234 and/or pS242 to S242.

In some embodiments, if in a biological sample obtained from a subject, at least one of, or at least two of, or at least three of: pT86, pS88, pT95 is detected, and at least one of: nT234 or nS242 is detected, then the subject can be selected for having, or at risk of having kidney injury, including but not limited to AKI, or can be selected as having ischemia or organ toxicity.

In some embodiments, if in a biological sample obtained from a subject, at least one of, or at least two of, or at least three of, at least 4 of or at least 5 of: pT86, pS88, pT95, nT234, nS242 is detected, then the subject can be selected for having, or at risk of having kidney injury, including but not limited to AKI, or can be selected as having ischemia or organ toxicity. Any combination is envisioned, for example, Table 1 shows exemplary combinations of different phosphorylation states of NPM in a biological sample from a subject can be used to select as having, or at risk of having kidney injury, including but not limited to AKI, or can be selected as having ischemia or organ toxicity.

TABLE 1

Exemplary combinations of phosphorylation states of the NPM polypeptide that can be detected in a method or assay that identify a subject, (or can be used to select a subject) as having, or risk of having kidney injury, AKI, ischemia or organ toxicity herein. "X" shows any combination of measurement of at least one, or at least 2 or at least 3, or at least 4 or at least all 5 phosphorylation states of pT86, pS88, pT95, nT234, and nS242 (where nT234 and nS242 identifies non-phosphorylated T234 and S242 respectively).

| pT86 | pS88 | pT95 | nT234 | nS242 |
|------|------|------|-------|-------|
| X    |      |      |       |       |
| X    |      |      |       | X     |
| X    |      |      | X     |       |
| X    |      |      | X     | X     |
| X    | X    |      |       |       |
| X    | X    |      | X     |       |
| X    | X    |      |       | X     |
| X    | X    |      | X     | X     |
| x    |      | X    |       |       |
| X    |      | X    | X     |       |
| X    |      | X    |       | X     |
| X    |      | X    | X     | X     |
| X    | X    | X    |       |       |
| X    | X    | X    | X     |       |
| X    | X    | X    |       | X     |
| X    | X    | X    | X     | X     |
|      | X    |      |       |       |
|      | X    |      | X     |       |
|      | X    |      |       | X     |
|      | X    |      | X     | X     |
|      | X    | X    |       |       |
|      | X    | X    | X     |       |
|      | X    | X    |       | X     |
|      | X    | X    | X     | X     |
|      |      | X    |       |       |
|      |      | X    | X     |       |
|      |      | X    |       | X     |
|      |      | X    | X     | X     |
|      |      |      | X     |       |
|      |      |      | X     | X     |
|      |      |      |       | X     |

In another embodiment, the methods disclosed herein can be used to measure a combination of at least one, or at least 2, or at least 3, or at least 4 or at least 5 of phosphorylation states of NPM polypeptide as shown in Table 2, where if their presence is detected, it identifies a subject, or can be used to select a subject, as having, or risk of having kidney injury, AKI, ischemia or organ toxicity as described herein

TABLE 2

Exemplary combinations of phosphorylation states of the NPM polypeptide assessed in a method or assay to identify a subject, (or can be used to select a subject) as having, or risk of having kidney injury, AKI, ischemia or organ toxicity as described herein.

| Combination of any one maker | Combo of any 2/5 NPM phosphorylation sites | Combo of any 3/5 NPM phosphorylation sites | Combo of any 4/5 NPM phosphorylation sites | All five NPM phosphorylation sites |
|---|---|---|---|---|
| pT86 | pT86, pS88 | pT86, pS88, pT95 | pT86, pS88, pT95, nT234 | pT86, pS88, pT95, nT234, nS242 |
| pS88 | pT86, pT95 | pT86, pS88, nT234 | pT86, pS88, pT95, nS242 | |
| pT95 | pT86, nT234 | pT86, pS88, nS242 | pT86, pS88, nT234, nS242 | |
| nT234 | pT86, nS242 | pT86, pT95, nT234 | pT86, pT95, nT234, nS242 | |
| nS242 | pS88, pT95 | pT86, pT95, nS242 | pS88, pT95, nT234, nS242 | |
|  | pS88, nT234 | pT86, nT234, nS242 | | |
|  | pS88, nS242 | pS88, pT95, nT234 | | |
|  | pT95, nT234 | pS88, pT95, nS242 | | |
|  | pT95, nS242 | pS88, nT234, nS242 | | |

TABLE 2-continued

Exemplary combinations of phosphorylation states of the NPM polypeptide assessed in a method or assay to identify a subject, (or can be used to select a subject) as having, or risk of having kidney injury, AKI, ischemia or organ toxicity as described herein.

| Combination of any one maker | Combo of any ⅖ NPM phosphorylation sites | Combo of any ⅗ NPM phosphorylation sites | Combo of any ⅘ NPM phosphorylation sites | All five NPM phosphorylation sites |
|---|---|---|---|---|
| | nT234, nS242 | pT95, nT234, nS242 | | |

In alternative embodiments, if in a biological sample obtained from a subject, at least three of, at least 4 of or at least 5 of: nT86, nS88, nT95, pT234, pS242 is detected, then the subject is not selected or identified as having, or at risk of having kidney injury, including but not limited to AKI, or is not selected as having ischemia or organ toxicity. For example, in such an embodiment, the methods disclosed herein can be used to measure a combination of at least 3, or at least 4 or at least 5 of phosphorylation states of NPM polypeptide as shown in Table 3, where if their presence is detected, it identifies a subject, or can be used to select a subject, as not having, or not at risk of having kidney injury, AKI, ischemia or organ toxicity.

TABLE 3

Exemplary combinations of phosphorylation states of the NPM polypeptide assessed in a method or assay to identify a subject, or to select a subject, as not having, or not risk of having kidney injury, AKI, ischemia or organ toxicity.

| Combo of any ⅗ NPM phosphorylation sites | Combo of any ⅘ NPM phosphorylation sites | All five NPM phosphorylation sites |
|---|---|---|
| nT86, nS88, nT95 | nT86, nS88, nT95, pT234 | nT86, nS88, nT95, pT234, pS242 |
| nT86, nS88, pT234 | nT86, nS88, nT95, pS242 | |
| nT86, nS88, pS242 | nT86, nS88, pT234, pS242 | |
| nT86, nT95, pT234, | nT86, nT95, pT234 pS242 | |
| nT86, nT95, pS242 | nS88, nT95, pT234, pS242 | |
| nT86, pT234, pS242 | | |
| nS88, nT95, pT234 | | |
| nS88, nT95, pS242 | | |
| nS88, pT234, pS242 | | |
| nT95, pT234, pS242 | | |

In some embodiments, the diagnostic method comprises measuring and detecting the phosphorylation of at least one of serine or threonine residue selected from: T86, S88, or T95 of the nucleophosmin (NPM) polypeptide; or the absence of phosphorylation of at least one of at least one serine residue selected from T234 or S242 on a nucleophosmin (NPM) polypeptide.

In some embodiments, the diagnostic method comprises measuring and detecting, in a biological sample obtained from the subject, at least one of: the presence of phosphorylation of at least one of serine or threonine residue selected from: T86, S88, or T95 of the nucleophosmin (NPM) polypeptide; or the absence of phosphorylation of at least one of at least one serine residue selected from T234 or S242 on a nucleophosmin (NPM) polypeptide.

In some embodiments, a method to determine if a subject has kidney injury or acute kidney injury (AKI), comprises (a) using an assay to detect at least on of: (i) the presence of phosphorylation of at least one of serine or threonine residue selected from: T86, S88, or T95 of the nucleophosmin (NPM) polypeptide in a biological sample obtained from a subject; and/or (ii) the absence of phosphorylation of at least one of at least one serine residue selected from T234 or S242 on a nucleophosmin (NPM) polypeptide; and (b) selecting the subject as having kidney injury or acute kidney injury (AKI), if the subject has the presence of phosphorylation of at least one of: T86, S88, or T95 of the nucleophosmin (NPM) polypeptide is detected, or the absence of phosphorylation of at least one of at least one serine residue selected from T234 or S242 on a nucleophosmin (NPM) polypeptide, or both. For example, in some embodiments, one can use antibodies or antigen-binding fragments thereof which specifically bind to any one or more of pT86, pS88, or pT95, and/or pT234 or pS242, and where specific binding of one or more antibody or antigen-binding fragment to pT86, pS88, or pT95 is detected, and binding is not detected with the antibodies or antigen-binding fragments to pT234 or pS242, it identifies a subject to have kidney injury, and in some embodiments, AKI, or other ischemic tissue stress, or organ injury.

In some embodiments, the method further comprises administering an effective amount of a treatment for kidney injury or AKI to the subject diagnosed and selected as having kidney injury or acute kidney injury (AKI) in step (b). In some embodiments, an effective amount of a treatment for kidney injury or AKI is administering to the subject an agent which inhibits the phosphorylation of at least one of: T86, S88, T95 of the NPM polypeptide, and/or inhibits the dephsporylation of at least one of: T232 or S240 of the NPM polypeptide, thereby inhibiting the formation of a NPM-Bax complex. In alternative embodiments, an effective amount of a treatment for kidney injury or AKI is administering to the subject wherein the treatment for kidney injury or AKI is administering to a subject a composition comprising at least one peptide from any peptide comprising the amino acid sequences of: TVTIFVAGVL-TASLTIWKKMG (SEQ ID NO: 1); TLKMSVQPTVSLGGFEITPPVVLRLK (SEQ ID NO: 2) and ESFKKQEKTPKTPKGPSSVEDIKAK (SEQ ID NO: 3), or peptide with at least 85% or 90% or 95% sequence identity to any of SEQ ID NO: 1-3.

In some embodiments, a method to determine if a subject has kidney injury or acute kidney injury (AKI), comprises obtaining a biological sample from a subject, and measuring for the presence of phosphorylation of at least one serine or threonine residue on the nucleophosmin (NPM) polypeptide at residues T86, S88, or T95, or measuring the absence of phosphorylation of at least one serine residue T234 and S242 on the nucleophosmin (NPM) polypeptide, or both.

In some embodiments, a method comprises obtaining a biological sample from a subject, and measuring for the presence of phosphorylation of at least one serine or threonine residue on the nucleophosmin (NPM) polypeptide at residues T86, S88, or T95, and measuring the absence of phosphorylation of at least one serine residue T234 and S242 on the nucleophosmin (NPM) polypeptide.

The diagnostic methods, assays and kits can be performed on any biological sample obtained from the subject, including but not limited to urine samples, blood samples, biopsy samples and the like. In some embodiments, the sample is selected from the group consisting of; a whole blood sample a plasma sample, a serum sample or a fractionated blood sample.

In some embodiments, the presence of phosphorylation of at least one residues on the NPM polypeptide at residues T86, S88, or T95 is determined by measuring and detecting the presence of binding of a phosphorylation specific antibody that preferentially bind to any one of: phospho-T86, phopho-S88 or phospho-T95 on the NPM polypeptide. In some embodiments, the absence of phosphorylation of at least one serine residue T234 and S242 on NPM polypeptide is determined by measuring and detecting the absence of binding of a phosphorylation specific antibody that preferentially bind to any one of: phospho-T234 or phopho-S242 on the NPM polypeptide.

In some embodiments, the presence of phosphorylation of at least one residues on the NPM polypeptide at residues T86, S88, or T95 is determined by measuring the presence of binding with at least one of: (i) a phosphorylation specific antibody or antigen-binding fragment thereof that specifically binds to phospho-T86 on the NPM polypeptide; (ii) a phosphorylation specific antibody or antigen-binding fragment thereof that specifically binds to phospho-S886 on the NPM polypeptide; or (iii) a phosphorylation specific antibody or antigen-binding fragment thereof that specifically binds to phospho-T95 on the NPM polypeptide.

In some embodiments, the absence of phosphorylation of at least one serine residue or threonine residue selected from T234 and S242 on the NPM polypeptide is determined by the absence of binding with at least one of: (i) a phosphorylation specific antibody or antigen-binding fragment thereof that specifically binds to phospho-T234 on the NPM polypeptide; or (ii) a phosphorylation specific antibody or antigen-binding fragment thereof that specifically binds to phospho-S242 on the NPM polypeptide.

B. Diagnosis of Kidney Injury

In some embodiments, the diagnostic methods disclosed herein, can be used to accurately and reliably detect ischemic injury of tissues, organ toxicity and kidney injury, including but not limited to acute kidney injury (AKI) and chronic kidney disease (CKD) in subjects, and subjects, (e.g., type I diabetic subjects) at risk of end stage renal disease (ESRD).

For example, in some embodiments where phospho-specific antibodies are used, e.g., phospho-specific antibodies to at least one of pT86, pS88, pT95, and phospho-specific antibodies to one or both of pT234, pS242, the presence of binding of a phospho-specific antibody to at least one of pT86, pS88, pT95, and the absence of binding of a phospho-specific antibody to at least one of pT234, pS242 can be used to identify a subject with any one of: ischemia, organ toxicity, kidney injury, AKI or CKD.

In alternative embodiments, where phospho-specific antibodies are used, e.g., phospho-specific antibodies to at least one of pT86, pS88, pT95, and antibodies that specifically bind to one or both of nT234, nS242, the presence of binding of a phospho-specific antibody to at least one of, or at least 2 of pT86, pS88, pT95, and the presence of binding of a specific antibody to at least one of nT234, nS242 can be used to identify a subject with any one of: ischemia, organ toxicity, kidney injury, AKI or CKD.

In some embodiments, where the phosphorylation status of one, or 2 or 3 or 4 or 5 of pT86, pS88, pT95, nT234, nS242 of the NPM polypeptide are detected, in particular, at least one of pT86, pS88, pT95 is detected and at least one of nT234, nS242 of the NPM polypeptide are detected, the subject from whom the biological sample was obtained can be treated with an appropriate treatment for kidney injury or AKI as disclosed herein.

C. Methods and Assays to Detect Phosphorylation States of any of the 5 Ischemic-Induced Phosphorylation/Dephosphorylation States of NPM Polypeptide (i.e., Methods to Detect pT86, pS88, pT95, nT234, nS242 on NPM Polypeptide).

In some embodiments, an agent which specifically binds to any one or more of amino acid residues: pT86, pS88, pT95, pT234 or pS242 on the NPM polypeptide is an antibody or antibody fragment (e.g., an antigen-binding Ab fragment), or a protein-binding molecule. Suitable antibodies include, but are not limited to, polyclonal, monoclonal, chimeric, humanized, recombinant, single chain, $F_{ab}$, $F_{ab'}$, $F_{sc}$, $R_v$, and $F_{(ab')2}$ fragments, and an $F_{ab}$ expression library. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies. In general, an antibody molecule obtained from humans can be classified in one of the immunoglobulin classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies provide high binding avidity and unique specificity to a wide range of target antigens and haptens. Monoclonal antibodies useful in the practice of the methods disclosed herein include whole antibody and fragments thereof and are generated in accordance with conventional techniques, such as hybridoma synthesis, recombinant DNA techniques and protein synthesis.

The ischemic-induced phosphorylated form of the NPM polypeptide (i.e., having the phosphorylation status of one or more of pT86, pS88, pT95, nT234, nS242), or a portion or fragment thereof, can serve as an antigen, and additionally can be used as an immunogen to generate antibodies that immunospecifically bind the antigen, using standard techniques for polyclonal and monoclonal antibody preparation. Preferably, the antigenic peptide comprises at least 10 amino acid residues, or at least 15 amino acid residues, or at least 20 amino acid residues, or at least 30 amino acid residues.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

Anti-NPM antibodies are also commercially available from vendors such as Biorbyt (Cambridge, UK), GeneTex (Irvine, USA), Aviva Systems Biology (Beijing, CN), Bioss Inc. (Woburn, USA), Sino Biological (Beijing CN), *Acris* Antibodies GmbH (San Diego, USA), Raybiotech, Inc. (Norcross, USA), OriGene Technologies (Rockville, USA), Enzo Life Sciences (Farmingdale, USA), and Abcam (Cambridge, UK).

(i) Phospho-Specific NPM Antibodies:

Exemplary antibodies which can be used to identify an ischemic-induced phosphorylated form of the NPM polypeptide (i.e., having the phosphorylation status of one or more of pT86, pS88, pT95, nT234, nS242) can be generated by one of ordinary skill in the art. In particular, one can make antibodies or antibody fragments or antigen-binding fragments thereof that specifically bind to any of pT86, pS88, pT95, or pT234, pS242 according to the methods disclosed in U.S. Pat. No. 5,559,681, which is incorporated herein in its entirety by reference.

Generation of antibodies or antigen-binding fragments thereof that specifically bind to any of pT86, pS88, pT95, or pT234, pS242 (or nT234 or nS242) of the NPM polypeptide can be generated using activation-specific phosphorptein immunodetection (APHID). In particular, peptides of the ischemic-induced phosphorylated form of the NPM polypeptide (i.e., having the phosphorylation status of one or more of pT86, pS88, pT95, nT234, nS242) can be generated, and coupled (via an amino terminal cysteine residue) to a carrier protein (e.g., hemocyanin), combined with adjuvant and inoculated into rabbits. Following raising of polyclonal antisera, antibodies to the phosphorylated peptide can be purified in a reverse-purification process by adsorption of non-activation-specific antibodies to an unphosphorylated peptide of the same sequence. Where necessary, contaminating non-receptor-specific antiphosphotyrosine antibodies can be removed by adsorption to phosphotyramine or phosphoserine.

APHID technology is generally applicable to the identification of protein isoforms characterized by varying phosphorylation states. A typical scheme for preparing polyclonal antibodies for activation-state-specific phosphoprotein immunodetection is shown in FIG. 1 of U.S. Pat. No. 5,559,681 which is incorporated herein in its entirety by reference. A skilled artisan can use the APHID technology to generate phospho-specific NPM polypeptides (e.g., antibodies that specifically bind NPM polypeptides that have one or more pT86, pS88, pT95 residues), or can detect dephosphorylation of specific residues of NPM (e.g., antibodies that specifically bind to NPM polypeptides that have one or both of nT234 or nS242).

(ii) Assays for Detection of Ischemic-Induced Phosphorylated Form of the NPM Polypeptide (i.e., Having the Phosphorylation Status of One or More of pT86, pS88, pT95, nT234, nS242).

RIA and ELISA provide the benefit of detection sensitivity, rapidity, accuracy, possible automation of procedures, and the like, for the determination of the presence of, or concentration or level of the phosphorylation state of any one of amino acid residue (i.e., T86, S88, T95, T234, S242) of the NPM polypeptide (Modern Rheumatology 13: 22-26 (2003)), Ohkuni et al., (International Congress Series 1289: 71-74 (2006)), and Mitchell et al., (Mol Microbiol. 5: 1883-8 (1991)). Radioimmunoassay (Kashyap, M. L. et al., J. Clin. Invest. 60:171-180 (1977)) is a technique in which detection antibody can be used after labeling with a radioactive isotope such as 125I. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

Immunoassays

The most common enzyme immunoassay is the "Enzyme-Linked Immunosorbent Assay (ELISA). There are different forms of ELISA which are well known to those skilled in the art, e.g. standard ELISA, competitive ELISA, and sandwich ELISA. The standard techniques for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904. ELISA is a technique for detecting and measuring the concentration of an antigen, such as an acute kidney injury biomarker, using a labeled (e.g. enzyme linked) form of the antibody.

In a "sandwich ELISA", an antibody is linked to a solid phase (i.e. a microtiter plate) and exposed to a biological sample containing antigen (e.g. an acute kidney injury biomarker). The solid phase is then washed to remove unbound antigen. A labeled antibody (e.g. enzyme linked) is then bound to the plate bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", a specific concentration of an antibody specific for the phosphorylation state of any one of amino acid residue (i.e., T86, S88, T95, T234, S242) of the NPM polypeptide is incubated with a biological sample. The antibody mixture is then contacted with a solid phase (e.g.

a microtiter plate) that is coated with NPM polypeptide. Where there the antibody binds to a phosphorylated residue on the NPM polypeptide, (e.g., any one of amino acid residue p T86, pS88, pT95, pT234, pS242), the less free antibody that will be available to bind to the solid phase. A labeled (e.g., enzyme linked) secondary antibody is then added to the solid phase to determine the amount of primary antibody bound to the solid phase.

In some embodiments, the phosphorylation states of one or more amino acid residues of: T86, S88, T95, T234, S242 of the NPM polypeptide can be determined simultaneously, in a multiplex fashion, by ELISA (enzyme-linked immunosorbent assay). The biological sample, e.g., urine sample can be, for example, one of a plurality of biological samples obtained at one of the various timepoints from a subject in need. In some embodiments, the biological sample is a human urine sample or blood sample from a subject, to be tested for determining the phosphorylation states of one or more residues T86, S88, T95, T234, S242 of the NPM polypeptide according to the methods described herein. The urine or blood sample (e.g., plasma, serum etc.) from the individual may further be serially diluted, according to the needs of the assay, and as known to one of ordinary skill in the art. In some embodiments, one or more of a plurality of antibodies or antigen-binding fragments specific for the phosphorylation state of each of T86, S88, T95, T234, S242 are assayed in a single sample which is contacted with the biological sample, thus forming an antibody-NPM complex or NPM-antigen-binding fragment complex. In some embodiments, each antibody or antigen-binding fragment specific for each phosphorylated residue of T86, S88, T95, T234, S242 of NPM polypeptide is labeled with a different label. In some embodiments, each different label is a fluorescent label. In all such embodiments, each different label has a unique emission spectra, such that each antibody can be detected individually. Therefore, for example, one can determine if the individual antibodies or antigen-binding fragments bind to each of the phosphorylated amino acid residues pT86, pS88, pT95, and where the individual antibodies or antigen-binding fragments do not bind to phosphorylated amino acid residues pT234 or pS242. Therefore, the phosphorylation state of each amino acid of T86, S88, T95, T234, S242 can then be determined by calculating different or changes in the emission spectrum, wherein the relative intensity of signal from each of the fluorescent labels correlates with the binding of, and number of antibodies against the particular amino acid residue (i.e., T86, S88, T95, T234, S242) being assayed. For example, if looking at only 2 phosphorylation residues, T86 and S88, if pT86 is identified with a red fluorescent signal and pS88 is identified with a yellow signal, a red signal would identify phosphorylation of just pT86, a yellow signal would identify just phosphorylation of pS88, and an orange signal would identify both pT86 and pS88 (which would identify that there is likely AKI). In alternative embodiments, antibodies or antigen binding fragments to detect the phosphorylation state of each amino acid residue (i.e., T86, S88, T95, T234, S242) can be assayed in a separate well. The wells can be normalized to a well comprising all of the necessary ELISA reagents with the exception of the sample. A series of standards having known concentrations of each of the various biomarkers being assayed permits actual quantification of the concentration of each of the biomarkers in the sample.

In some aspects, the phosphorylation state of any one or more of amino acid residues (i.e., T86, S88, T95, T234, S242) of the NPM polypeptide can be assayed can be determined alone, or in combination with other biomarkers (e.g., other biomarkers for AKI such as for example, albuimin or serum creatinine, KIM-1 or other disease pathologies, or a normalizing protein biomarker) simultaneously, in a multiplex fashion, using a multiplex bead assay. For example, in one embodiment, beads of different sizes or colors (emission spectra) are used for multiplexed immunoassays to determine the phosphorylation state of each amino acid residue (i.e., T86, S88, T95, T234, S242) of the NPM polypeptide and optionally, one or more other blood biomarkers. In some embodiments of this aspect, a plurality of beads of different sizes are coated with different antibodies, wherein each bead of a specific size is conjugated to an antibody specific for a single biomarker (e.g., a bead of one size is conjugated to an antibody for pT86 and beads of different sizes are conjugated to different antibodies that are either specific to the other phosphorylation residues (e.g., S88, T95, T234, S242) or specific to different blood biomarkers, or antibodies specific to normalizing proteins). Accordingly, each bead can be differentiated by its unique light scatter characteristics. A biological sample, such as a urine, or plasma or serum sample, to be assayed for the phosphorylation state of at least one or more amino acid residue (i.e., T86, S88, T95, T234, S242) of the NPM polypeptide and optionally at least one other biomarker is then contacted with a plurality of beads of different sizes, forming a bead-biomarker conjugate, and the phosphorylation state of each amino acid residue (i.e., T86, S88, T95, T234, S242) of the NPM polypeptide and the concentration of other AKI biomarker can then be ascertained by, for example, performing flow cytometric analyses on the bead bound-sample. In some embodiments, one of the other biomarkers assessed in a multiplex bead assay is a normalizing protein to detect the level of protein in the biological sample.

In some embodiments of this aspect, such bead-based technology can be employed wherein bead populations are identified by one type of fluorescence, while the biomarker-dependent signal is generated by detection reagents carrying a second type of fluorescent signal, thus creating a bead set specific for detecting the phosphorylation states of each amino acid residue (i.e., T86, S88, T95, T234, S242) of the NPM polypeptide. In some embodiments, the bead-based technology can be used to detect additional biomarkers, e.g., one or more other normalizing proteins, and/or other biomarkers (e.g., normalizing proteins and/or total NPM polypeptide or other AKI biomarker, e.g., KIM-1, albuiminura and/or creatinine etc). In some embodiments, the distinguishable bead populations are prepared by staining the beads with two or more fluorescent dyes at various ratios. Each bead having a specific ratio of the two or more fluorescent dyes is conjugated to an antibody specific for one of a plurality of biomarkers, thus assigning each bead a unique fluorescent signature. The immunoassay signal is generated by detection reagents, coupled to a third type of fluorescent dye. A sample to be assayed for the phosphorylation states of each amino acid residue (i.e., T86, S88, T95, T234, S242) of the NPM polypeptide and optionally the total NPM polypeptide, is then contacted with the plurality of beads with unique fluorescent signatures and specific detection of pT86, pS88, pT95, pT234, pS242, forming a bead-biomarker conjugate for NPM or other biomarker present in the sample. That way, the presence of signal for antibodies that specifically bind to pT86, pS88, pT95, and the absence of a signal of antibodies that specifically bind to pT234 or pS242 can be detected. Thus the phosphorylation states of each amino acid residue (i.e., T86, S88, T95, T234, S242) of the NPM polypeptide by the presence or absence of a signal, as well as the concentration of the NPM polypeptide can be ascertained by flow cytometric analyses on the bead bound-sample. For example, in some embodiments, beads are dyed with fluorochromes having different fluorescence intensities. In some embodiments, the beads are 7.5 µm in diameter. In some embodiments, the fluorescent dye incorporated in the beads fluoresces strongly at 650 nm upon excitation with an argon laser. Each bead population of a given fluorescence intensity represents a discrete population for constructing an immunoassay for a single biomarker. Each bead population having a given fluorescence intensity upon excitation is covalently coupled with an antibody directed against a specific biomarker, e.g., an antibody or antigen binding fragment that specifically binds to each of pT86, pS88, pT95, pT234, pS242. These antibody-bound bead populations, each of which are unique in their fluorescence emission intensity, serve as capture beads for a combination of detection of any one of the phosphorylation states of each amino acid residue (i.e., T86, S88, T95, T234, S242) of the NPM polypeptide in a sample. That is, as stated above, the biological sample can be detected with as many as 7 different beads; each bead having an antibody that is specific for one of pT86, pS88, pT95, pT234, pS242, total NPM polypeptide, and a control housekeeping gene. The presence of a signal from the beads that specifically detect or bind to pT86, pS88, pT95, and the absence of the signal from the beads that specifically detect or bind to pT234, pS242 can be used to determine if the biological sample comprises the ischemic-induced phospho-NPM polypeptide. Beads that specifically detect the total NPM polypeptide and the housekeeping gene can serve as positive controls and/or normalizing controls. In alternative embodiments, the beads can comprise antibodies that specifically detect or bind to nT234 and/or nS242, where a presence of a signal from such beads can be used to determine if the biological sample comprises the ischemic-induced phospho-NPM polypeptide. It is envisioned that any combination of antibodies can be used, that are specific for the phosphorylated pT86, pS88, pT95, pT234, pS242 residues on the NPM polypeptide, or are specific for the non-phosphorylated residues (e.g., nT86, nS88, nT95, nT234, nS242).

Accordingly, as defined herein a "capture bead" is a bead having a unique fluorescence emission intensity conjugated to an antibody specific for the phosphorylation states of each amino acid residue (i.e., T86, S88, T95, T234, S242) of the NPM polypeptide. When these capture beads specific for different biomarkers are used as a mixture, the levels of individual biomarkers, the phosphorylation states of each amino acid residue (i.e., T86, S88, T95, T234, S242) of the NPM polypeptide, can be simultaneously measured within a given biological sample. In some embodiments, detection is further mediated by the binding of a specific detection antibody, for example, an antibody that detects any bead-biomarker complex present in a sample, that is directly conjugated with phycoerythrin (PE), to each of the corresponding capture bead-biomarker complexes present in the sample, thus providing a second fluorescent signal for each capture bead. The fluorescent signal is proportional to the concentration of the biomarker in the sample. Separately established calibration curves can be used to determine the concentration of each biomarker in the test sample, using dedicated analysis software, such as CBA software. The data collected using a flow cytometer include information about the physical and spectral parameters of the beads, such as size and the fluorescence emission characteristics of each bead population. These fluorescence emission characteristics include the fluorescent emission of the dyed beads, and the potential fluorescent emissions of the detection fluorochrome (for example, phycoerythrin). When samples are analyzed using a flow cytometer in conjunction with a typical data acquisition and analysis package (for e.g., BD CellQuest™ software), a list-mode data file is saved using a flow cytometry standard file format, FCS. The data stored in the FCS files can be reanalyzed to determine the median fluorescence intensities (MFI) of the various bead populations, defined by their unique physical and spectral characteristics, to then compare reference samples with unknowns. The level of the phosphorylation states of each amino acid residue (i.e., T86, S88, T95, T234, S242) of the NPM polypeptide being assayed within individual biological samples can then be calculated from calibration curves generated by serial dilutions of standard analyte solutions of known concentration. An automated or semiautomated analysis method can be used for rapid reanalysis of the data stored in each FCS file. For example, BD CBA Software is written in the Microsoft® Excel Visual Basic for Applications (VBA) programming language. The CBA Software can recognize FCS 2.0 and 3.0 format data files and automates the identification of CBA bead populations and the determination of detector fluorochrome MFI values for each bead population within the data file for a single sample. Using this data analysis function of the CBA Software for multiple standard files, the MFI values for standards are then determined and plotted. From the plotted standard curve and complex mathematical interpolation, values for unknown samples can be rapidly determined in comparison to known standards using the software.

Other techniques can be used to detect the phosphorylation states of each amino acid residue (i.e., T86, S88, T95, T234, S242) of the NPM polypeptide as required to practice the methods described herein, according to a practitioner's preference, and based upon the present disclosure. The suitability of a given method for measuring the phosphorylation states of each amino acid residue (i.e., T86, S88, T95, T234, S242) of the NPM polypeptide will depend on the ability of that method or assay to distinguish between each phosphorylation state, total NPM protein levels and other proteins in the biological sample. Thus, an immunoassay can distinguish on the basis of selective binding to the phosphorylation states of each amino acid residue (i.e., T86, S88, T95, T234, S242) of the NPM polypeptide and not another ser/thr/tyr (phosphorylated or non-phosphorylated) residue of the NPM polypeptide, or other protein in the biological sample. Spectrometric approaches can be applied when a given agent will have a distinct spectrum or profile in the assay relative to others. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Detectably labeled antibodies that specifically bind to the phosphorylation states of each amino acid residue (i.e., T86, S88, T95, T234, S242) of the NPM polypeptide can then be used to detect the presence or absence of phosphorylation at each site (e.g., amino acid residues, T86, S88, T95, T234, S242), as well as the levels or concentrations of NPM polypeptide, where the intensity of the signal from the detectable label corresponds to the amount of phosphorylation of each amino acid residue (i.e., T86, S88, T95, T234, S242) of the NPM protein assessed as well as, in some embodiments, the amount of NPM protein present. Levels can be quantitated, for example by densitometry.

The prognostic methods of the invention also are useful for determining a proper course of treatment for a patient having AKI. A course of treatment refers to the therapeutic measures taken for a patient after diagnosis or after treatment for injury.

The present invention is also directed to commercial kits for the detection and prognostic evaluation of AKI. The kit can be in any configuration well known to those skilled in the art and is useful for performing one or more of the methods described herein for the detection of the phosphorylation states of each amino acid residue (i.e., T86, S88, T95, T234, S242) of the NPM polypeptide in a biological sample obtained from a subject. The kits are convenient in that they supply many, if not all, of the essential reagents for conducting an assay for the detection of the phosphorylation states of each amino acid residue (i.e., T86, S88, T95, T234, S242) of the NPM polypeptide, such as described herein. In addition, the assay may be performed simultaneously with a standard or multiple standards included in the kit, such as a predetermined amount of a NPM polypeptide, or positive or negative controls for detection of any one or more of pT86, pS88, pT95, pT234 (or nT234), pS242 (or nS242) so that the results of the test can be quantified or validated.

In one embodiment, the kit comprises a means for detecting the phosphorylation states of each amino acid residue (i.e., T86, S88, T95, T234, S242) of the NPM polypeptide in a biological sample obtained from the subject. The kit can comprise a "dot blot" or a "dipstick" with at least one antibody, antigen-binding fragment or binding agent immobilized thereon, which specifically binds to one or more the phosphorylation states of each amino acid residue (i.e., T86, S88, T95, T234, S242) of the NPM polypeptide. Specifically bound NPM protein can then be detected using, for example, a second antibody that is detectably labeled with a calorimetric agent or radioisotope.

In some embodiments, a kit comprises a paper-based assay to determine the phosphorylation states of each amino acid residue (i.e., T86, S88, T95, T234, S242) of the NPM polypeptide in a biological sample. Such paper-based assays are well known in the art, e.g., as disclosed in International Application WO 2011097412 and U.S. Pat. No. 8,821,810 and US application US 2014/0193840 and published documents by Martinez et al., (2007), Patterned Paper as a Platform for Inexpensive, Low-Volume, Portable Bioassays. Angewandte Chemie International Edition. 2007; 46(8): 1318-1320, and Chung et al., (2010) Paper-Based ELISA. Angewandte Chemie International Edition; 2010; 49(28): 4771-4774, which are all incorporated herein in their entireties by reference.

In other embodiments, the assay kits may contain components for competitive and non-competitive assays, radioimmunoassay (RIA), multiplex bead assays, bioluminescence and chemiluminescence assays, fluorometric assays, sandwich assays, immunoradiometric assays, dot blots, enzyme linked assays including ELISA, microtiter plates, or immunocytochemistry. For each kit the range, sensitivity, precision, reliability, specificity, and reproducibility of the assay are established by means well known to those skilled in the art.

In one embodiment, methods to detect the phosphorylation state of any one or more of amino acid residues (i.e., T86, S88, T95, T234, S242) of the NPM polypeptide as disclosed herein include ELISA (enzyme linked immunosorbent assay), western blot, immunoprecipitation, immunofluorescence using detection reagents such as an antibody or protein binding molecules or protein-binding agents. Alternatively, the phosphorylation states of each amino acid residue (i.e., T86, S88, T95, T234, S242) of the NPM polypeptide can be detected in a subject by introducing into a subject a labeled antibody that specifically binds to at least one or more of the phosphorylation states of each amino acid residue (i.e., T86, S88, T95, T234, S242) of the NPM polypeptide and other types of detection agent. For example, the antibody can be labeled with a radioactive marker whose presence and location in the subject is detected by standard imaging techniques, particularly useful are methods that detect the phosphorylation states of each amino acid residue (i.e., T86, S88, T95, T234, S242) of the NPM polypeptide in a subject or in a biological sample.

Methods to detect the phosphorylation states of each amino acid residue (i.e., T86, S88, T95, T234, S242) of the NPM polypeptide in a biological sample are well known to persons skilled in the art, and are encompassed for use in this invention. Commercially available antibodies and/or ELISA kits for detection of one or more of the phosphorylation states of each amino acid residue (i.e., T86, S88, T95, T234, S242) of the NPM polypeptide in a biological sample are also useful in the methods of this invention. Some examples of such protein-binding molecules useful to detect the one or more phosphorylation states of each amino acid residue (i.e., T86, S88, T95, T234, S242) of the NPM polypeptide are commercially available, and include, but are not limited to, commercially available antibodies such as anti-phospho-Thr95 NPM antibody from AbCam, Bioss Antibodies, Cell Signaling Technologies (MA, USA), which can be found at world wide web site: "cellsignal-dot-com". In some embodiments, antibodies from other antibody companies, such as for example, Abnova corporation, Anogen, Alpco Diagnostics, Ray Biotech, alphagenix, autogen, R&D Systems, Pepro Tech EC Ltd, cytolab, Bender MedSystems GmbH, Biovision Research Products, EBD biosciences, Chemicon, Axxora Platform, Promo Cell Distrubuters, Cell Science, Santa Cruz Biotechnology, Sigma etc. can be used. In alternative embodiments, antibodies directed against the ischemia-induced phospho-NPM polypeptide with one or more phosphorylation states: T86, S88, T95, T234, S242 can also be used in disease diagnostics and prognostics.

In another embodiment, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change color, upon encountering the targeted molecules. In some instances, signal amplification can be integrated into the particular protocol, wherein a secondary antibody, that includes the marker stain or marker signal, follows the application of a primary specific antibody.

In some embodiments, the methods as described herein can be performed, for example, by utilizing pre-packaged diagnostic kits, such as those described above, comprising at least one probe which can be conveniently used, e.g., to determine whether a subject has or is at risk of developing disease such as AKI, CKD, ESRD and/or renal cell carcinoma (RCC), in particular clear cell renal cell carcinoma.

The term "protein-binding molecule" or "antibody-based binding moiety" or "antibody" includes immunoglobulin molecules and immunologically active determinants of immunoglobulin molecules, e.g., molecules that contain an antigen binding site which specifically binds (i.e. immunoreacts with) to the Psap proteins. The term "antibody-based binding moiety" is intended to include whole antibodies, e.g., of any isotype (IgG, IgA, IgM, IgE, etc.), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-based binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled.

The term "labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of Psap or Tsp-1 present in the tissue samples correlate to the intensity of the signal emitted from the detectably labeled antibody.

In one embodiment, the antibody-based binding moiety is detectably labeled by linking the antibody to an enzyme. The enzyme, in turn, when exposed to it's substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection can also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audioradiography. Isotopes which are particularly useful for the purpose of the present invention are $^3H$, $^{131}I$, $^{35}S$, $^{14}C$, and preferably $^{125}I$.

It is also possible to label an antibody with a fluorescent compound. When the fluorescently labeled antibody is exposed to light of the proper wavelength, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as 152Eu, or others of the lanthanide series. These metals can be attached to the antibody using such metal chelating groups as diethylenetriaminepentaacetic acid (DTPA) or ethylene diaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, levels of enzyme protein can be detected by immunoassays, such as enzyme linked immunoabsorbant assay (ELISA), radioimmunoas say (RIA), Immunoradiometric assay (IRMA), Western blotting, immunocytochemistry or immunohistochemistry, each of which are described in more detail below. Immunoassays such as ELISA or RIA, which can be extremely rapid, are more generally preferred. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

The most common enzyme immunoassay is the "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g. anti-enzyme) is linked to a solid phase (i.e. a microtiter plate) and exposed to a biological sample containing antigen (e.g. enzyme). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e. enzyme). The antigen-antibody mixture is then contacted with a solid phase (e.g. a microtiter plate) that is coated with antigen (i.e., enzyme). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analysed microscopically, most preferably by light microscopy of a sample stained with a stain that is detected in the visible spectrum, using any of a variety of such staining methods and reagents known to those skilled in the art.

Alternatively, "Radioimmunoassays" can be employed. A radioimmunoassay is a technique for detecting and measuring the concentration of an antigen using a labeled (e.g. radioactively or fluorescently labeled) form of the antigen. Examples of radioactive labels for antigens include 3H, 14C, and 125I. The concentration of antigen enzyme in a biological sample is measured by having the antigen in the biological sample compete with the labeled (e.g. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed $S.$ $aureus$. Yet another method for separating the antigen-antibody complex from the free antigen is by performing a "solid-phase radioimmunoas say" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

Other techniques can be used to detect the phosphorylation state of any one or more of amino acid residues (i.e., T86, S88, T95, T234, S242) of the NPM polypeptide in a biological sample according to a practitioner's preference, and based upon the present disclosure and the type of biological sample (i.e. plasma, urine, tissue sample etc). One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Detectably labeled anti-enzyme antibodies can then be used to assess enzyme levels, where the intensity of the signal from the detectable label corresponds to the amount of enzyme present. Levels can be quantified, for example by densitometry.

Immunological methods are particularly useful in the methods as disclosed herein, because the require only small quantities of biological material, and are easily performed and at multiple different locations. In some embodiments, such an immunologic method useful in the methods as disclosed herein uses a "lab-on-a-chip" device, involving a single device to run a single or multiple biological samples and requires minimal reagents and apparatus and is easily performed, making the "lab-on-a-chip" devices which detect the phosphorylation status, in particular the phosphorylation status of S10 residue of a topo I protein is ideal for rapid, on-site diagnostic tests to identify if a biological sample obtained from a subject is likely to be responsive to a topo I inhibitor. In some embodiments, the immunological methods can be done at the cellular level and thereby necessitate a minimum of one cell. Preferably, several cells are obtained from a subject affected with or at risk for developing cancer and assayed using the methods, kits, machines, computer systems and media as disclosed herein.

Mass Spectrometry

In other embodiments, the phosphorylation state of any one or more of amino acid residues (i.e., T86, S88, T95, T234, S242) of the NPM polypeptide present in a biological sample (e.g., urine, kidney biopsy whole blood, plasma or serum etc.) can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 2003/0199001, 2003/0134304, 2003/0077616, which are herein incorporated by reference in their entirety.

The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., "Proteinchip surface enhanced laser desorption/ionization (SELDI) mass spectrometry: a novel protein biochip technology for detection of prostate cancer biomarkers in complex protein mixtures," Prostate Cancer and Prostatic Diseases 2: 264-76 (1999); and Merchant and Weinberger, "Recent advancements in surface-enhanced laser desorption/ionization-time of flight-mass spectrometry," Electrophoresis 21: 1164-67 (2000), each of which is hereby incorporated by reference in its entirety, including all tables, figures, and claims. Mass spectrometry methods are well known in the art and have been used to quantify and/or identify biomolecules, such as proteins and hormones (see, e.g., Li et al., (2000), Tibtech. 18:151-160; Starcevic et. al., (2003), J. Chromatography B, 792: 197-204; Kushnir M M et. al. (2006), Clin. Chem. 52:120-128; Rowley et al. (2000), Methods 20: 383-397; and Kuster and Mann (1998), Curr. Opin. Structural Biol. 8: 393-400). Further, mass spectrometric techniques have been developed that permit at least partial de novo sequencing of isolated proteins. Chait et al., (1993), Science, 262:89-92; Keough et al., (1999), Proc. Natl. Acad. Sci. USA. 96:7131-

6; reviewed in Bergman (2000), EXS 88:133-44. Various methods of ionization are known in the art. For examples, Atmospheric Pressure Chemical Ionisation (APCI) Chemical Ionisation (CI) Electron Impact (EI) Electrospray Ionisation (ESI) Fast Atom Bombardment (FAB) Field Desorption/Field Ionisation (FD/FI) Matrix Assisted Laser Desorption Ionisation (MALDI) and Thermospray Ionisation (TSP) In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait). In SELDI, the substrate surface is modified so that it is an active participant in the desorption process. In one variant, the surface is derivatized with adsorbent and/or capture reagents that selectively bind the biomarker of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material. For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094. Detection and quantification of the biomarker will typically depend on the detection of signal intensity. For example, in certain embodiments, the signal strength of peak values from spectra of a first sample and a second sample can be compared (e.g., visually, by computer analysis etc.), to determine the relative amounts of particular biomarker. Software programs such as the Biomarker Wizard program (Ciphergen Biosystems, Inc., Fremont, Calif.) can be used to aid in analyzing mass spectra. The mass spectrometers and their techniques are well known to those of skill in the art. The various assays are described herein in terms of the detection of the phosphorylation state of any one or more of amino acid residues (i.e., T86, S88, T95, T234, S242) of the NPM polypeptide in a biological sample, e.g., urine sample. It is understood that the assays can be readily adapted to detect other analytes as needed e.g., for various other embodiments and or to detect protein levels and depending on the sample type, such as biopsy sample, whole blood, plasma or serum.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the phosphorylation state of any one or more of amino acid residues (i.e., T86, S88, T95, T234, S242) of the NPM polypeptide in a biological sample will typically depend on the detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

D. Biological Samples

In some embodiments, the detection of one or more phosporylations states of amino acid residues T86, S88, T95, T234, S242 of the NPM polypeptide is assessed in a biological sample obtained from a subject. In some embodiments, a biological sample is a sample of biological fluid, tissue, or cells, in a healthy and/or pathological state obtained from a subject. Such samples include, but are not limited to, urine, whole blood, serum, plasma, sputum, saliva, amniotic fluid, lymph fluid, tissue or fine needle biopsy samples (including kidney biopsy samples), peritoneal fluid, cerebrospinal fluid, nipple aspirates, and includes supernatant from cell lysates, lysed cells, cellular extracts, and nuclear extracts. In some embodiments, the whole blood sample is further processed into serum or plasma samples. In some embodiments, a sample is taken from a human subject, e.g., a subject selected for diagnosis as discussed in section IV.E herein.

Accordingly, in one embodiment of this aspect and all other aspects described herein, a biological sample as defined herein can include a human biological sample, preferably a urine sample or a microdissected human samples, are derived from a small tissue fraction, particularly from a kidney tissue fraction. In some embodiments, the human samples are preferably harvested by biopsy and/or surgical extraction, and in some embodiments, the human sample can be stored, for example as frozen biological sample prior to subjecting to the detection of phosphorylation status of the NPM polypeptide using the methods, kits, and media as disclosed herein.

In some embodiments of these methods and all such methods described herein, the biological sample is a kidney biopsy, urine, blood, serum sample, or cells pelleted from a urine sample.

In some embodiments, the biological sample is treated after it is obtained from a subject to "fix" the phosphorylation status of NPM polypeptide, such that there is not a change in phosphorylation status (i.e. a dephosphorylation or increase in phosphorylation) of NPM polypeptide from the time the tissue (i.e. biological sample) was harvested from the subject and the time it is analysed by the methods and kits as disclosed herein. In some embodiments, this is important, because phosphorylation status can rapidly alter (i.e. dephosphoryle or phosphorylate) if the phosphorylation status is not stable after removal of a biological sample or tissue from a subject, thus dephosphorylation may increase or phosphorylation may increase leading to inaccuracies (i.e. false positives or false negatives) in the detection and analysis as disclosed herein. Accordingly, in some embodiments, a biological sample, such as urine or tissue biopsy is optionally treated to "fix" the phosphorylation status of topo1 polypeptide before the biological sample is subject to analysis by the methods, kits, machines, computer systems and computer readable media as disclosed herein. Methods to fix a biological sample, such as a tissue biopsy are well known by a skilled artisan, and include formaldehyde, formalin, FAA fixative and other fixatives and methods commonly known by a skilled artisan.

E. Subjects Amenable for Diagnosis of Kidney Injury or Treatment with NPM Peptides In all aspects of the invention, the assays, kits and methods, e.g., methods for treating acute stress, ischemia or kidney injury, including AKI in a subject, or diagnosis methods disclosed herein, e.g., methods for monitoring the effectiveness of a treatment (e.g., method to monitor treatment progress) is performed on a subject who is suspected to have, or has been previously diagnosed with or identified as suffering from or having a kidney injury, e.g., AKI, or injury to the proximal tubule of the kidney. In some embodiments, the diagnosis methods are performed on a biological sample obtained from a subject who has been selected to be diagnosed with, or suspected to have a condition in need of treatment (e.g. acute kidney injury, chronic kidney disease, end-stage renal disease, or diabetic nephropathy) or one or more complications related to such a condition, or optionally, having undergone, or to undergo a cardiopulmonary bypass (CBP), or have already undergone treatment for such a condition. The subject can also have been selected as being risk of developing a condition associated with kidney fibrosis. For example, acute kidney injury is now appreciated to be significantly associated with increased risk of future chronic kidney disease and end-stage renal disease.

In some embodiments, the biological sample (e.g., urine sample or blood sample) used in the assays, methods and kits as disclosed herein is from a subject selected to be assessed, where the subject has been identified to suffer from an insult or injury to the kidney, e.g., an injury to the proximal tube of the kidney.

In some embodiments, the biological sample (e.g., urine sample or blood sample) used in the assays, methods and kits as disclosed herein is from a subject selected to be assessed, where the subject has been identified to suffer from acute kidney injury, and the methods described herein are used to treat the subject from developing chronic kidney disease. In some embodiments, the method as used herein are used to prevent the worsening of a symptom of AKI, and/or monitoring the progression of AKI.

In some embodiments, the biological sample (e.g., urine sample or blood sample) used in the assays, methods and kits as disclosed herein is from a subject selected to be assessed, where the subject has been identified to suffer from chronic kidney disease or after a cardiopulmonary bypass (CBP) operation, and the methods described herein are used to prevent the subject from progressing to end-stage renal disease.

Common symptoms of chronic kidney disease include tiredness, nausea, urine-like odor to the breath, bone pain, abnormally dark or light skin, itching, restless leg syndrome, blood in stools, bruising easily, pedal edema, and peripheral edema. Chronic kidney disease can be diagnosed through, e.g., medical history, a blood test that measures complete blood count, BUN level, or creatinine level, renal flow and scan, and renal ultrasound.

In some embodiments, the biological sample (e.g., urine sample or blood sample) used in the assays, methods and kits as disclosed herein is from a subject selected to be assessed, where the subject has been identified to have diabetes, e.g., type 1 diabetes. In some embodiments, the methods described herein are used to monitor the kidney injury in such a subject, and to monitor and optionally treat the subject prevent the subject from progressing to end-stage renal disease.

When the kidneys are clearly beginning to shut down, it is called end stage renal disease. Symptoms of end-stage renal disease include, but are not limited to, a decrease in urine output, inability to urinate, fatigue, headaches, unexplained weight loss, loss of appetite, nausea and vomiting, dry skin and itching, changes in skin color, bone pain, confusion and difficulty concentrating, bruising easily, numbness in hands and feet, bad breath, excessive thirst, and frequent hiccups. End-stage renal disease can be diagnosed through, e.g., a physical examination and blood tests to check kidney function.

In some embodiments, the biological sample (e.g., urine sample or blood sample) used in the assays, methods and kits as disclosed herein is from a subject selected to be assessed, where the subject has been identified to have diabetic neuropathy. Symptoms of diabetic nephropathy include, but are not limited to, lomerular hypertrophy, basement membrane thickening, and mesgangial expansion. Diabetic nephropathy can be diagnosed and/or monitored using blood or urine tests, as well as by kidney biopsy. Such tests may be used to monitor improvement of symptoms during or following treatment. By way of example, diabetic nephropathy can be diagnosed and/or assessed by evaluating blood and/or protein content in the urine. Diabetic nephropathy can also be diagnosed and/or assessed by evaluating creatinine and/or urea level in blood, and/or by estimates of glomerular filtration rate based on creatinine score.

In some embodiments, the biological sample (e.g., urine sample or blood sample) in the assays, methods and kits as disclosed herein is from a subject selected to be assessed, where the subject has been identified to have kidney fibrosis or is at risk of developing kidney fibrosis. For example, the risk of developing kidney fibrosis is increased if the kidney suffers from an injury or insult. A condition associated with kidney fibrosis can be diagnosed by a blood test that measures the level of waste products such as creatinine and urea, a urine test that looks for abnormalities, an imaging test using ultrasound to assess kidney's structure and size, or a kidney biopsy.

F. Appropriate Therapy for the Treatment of Kidney Injury or Kidney Disease or AKI In some embodiments, the methods and assays further comprise providing an appropriate treatment to the subject for kidney injury, e.g., where the biological sample obtained from subject is identified to have a NPM polypeptide having the phosphorylation state of any one or more of amino acids: pT86, pS88, pT95, nT234, nS242. The management of acute kidney injury hinges, in part, on identification and treatment of the underlying cause. In addition to treatment of the underlying disorder, management of acute kidney injury can include the avoidance of substances that are toxic to the kidneys, or "nephrotoxins," which include, but are not limited to, non-steroidal anti-inflammatory drugs (NSAIDs), such as ibuprofen, iodinated contrasts, such as those used for CT scans, and others. Therefore, in some embodiments, an appropriate treatment for kidney injury or disease is to avoid nephrotoxins, including the subject reducing or stopping alcohol consumption and administration of drugs e.g., NSAIDS and/or other non-necessary pharmaceutical compounds.

The choice of a specific therapeutic treatment for acute kidney injury is dependent, in part, on the cause of the acute renal injury, i.e., whether the cause of the acute kidney injury is pre-renal, renal instrinsic, or post-renal. For example, in pre-renal acute kidney injury in the absence of fluid overload, administration of intravenous fluids is typically the first step to improve renal function. Fluid administration may be monitored, for example, with the use of a central venous catheter to avoid over- or under-replacement of fluid. In situations where low blood pressure is a persistent problem in the fluid replete patient, inotropes, such as norepinephrine and dobutamine, may be given to improve cardiac output and hence renal perfusion. In some embodiments, dopamine may be administered. In cases of prerenal acute kidney injury induced by toxins, discontinuation of the offending agent, such as aminoglycoside, penicillin, NSAIDs, or acetaminophen, can be an effective treatment. If the cause of acute kidney injury is obstruction of the urinary tract, relief of the obstruction (with a nephrostomy or urinary catheter) may be necessary.

In cases where the acute kidney injury has renal intrinsic causes, specific therapies and treatment regimens are administered based on the nature of the renal intrinsic cause. For example, intrinsic acute kidney injury due to Wegener's granulomatosis may respond to steroid medication.

Renal replacement therapy, such as hemodialysis or continuous venovenous hemofiltration (CVVH), may be instituted in some cases of acute kidney injury. Metabolic acidosis and hyperkalemia, the two most serious biochemical manifestations of acute renal failure, may require medical treatment with sodium bicarbonate administration and antihyperkalemic measures, unless dialysis is required.

In some cases of acute kidney injury, lack of improvement after treatment with fluid resuscitation, therapy-resistant hyperkalemia, metabolic acidosis, or fluid overload may necessitate artificial support in the form of dialysis or hemofiltration.

Accordingly, in some embodiments, an appropriate treatment for kidney injury or disease is any of, or a combination of; intravenous fluid administration (e.g. fluid resuscitation or fluid overload), hyperkalemia, metabolic acidosis, administration of inotropes (e.g., norepinephrine and dobutamine), administration of dopamine, discontinuation of an offending agent, e.g., aminoglycoside, penicillin, NSAIDs, or acetaminophen and/or alcohol, dialysis, administration of steroids, hemodialysis or continuous venovenous hemofiltration (CVVH), administration of sodium bicarbonate administration, and/or antihyperkalemic measures.

In some cases of acute kidney injury, in which end-stage renal failure has occurred, an appropriate treatment involves a kidney transplant. As defined herein, a "kidney transplant" or "renal transplant" is the organ transplant of a kidney into a patient with end-stage renal disease. Kidney transplantation is typically classified as deceased-donor (formerly known as cadaveric) or living-donor transplantation depending on the source of the recipient organ. Living-donor renal transplants are further characterized as genetically related (living-related) or non-related (living-unrelated) transplants, depending on whether a biological relationship exists between the donor and recipient.

In some embodiments, an appropriate treatment for kidney injury can comprise administration of a treatment to the subject, e.g., alone or as part of a combinatorial therapy. For example, TGF-β inhibitors can be administered to hamper the progression of kidney fibrosis. Non-limiting examples of agents and/or therapies which can be used to treat chronic kidney disease, end-stage renal disease, or diabetic nephropathy include any, or any combination of angiotensin converting enzyme inhibitors (ACEIs), angiotensin II receptor antagonists (ARBs), bardoxolone methyl, olmesartan medoxomil, sulodexide, avosentan, and renal replacement therapy.

The efficacy of a given treatment for acute kidney injury can be determined by the skilled clinician, for example, using the criteria discussed herein. However, a treatment is considered "effective treatment," as the term is used herein, if any one or all of the signs or symptoms of acute kidney injury, such as in one example, urine creatinine levels, are altered in a beneficial manner, other clinically accepted symptoms or markers of disease are improved, or even ameliorated, e.g., by at least 10% following treatment. Efficacy can also be measured by a failure of an individual to worsen as assessed by hospitalization or need for medical interventions (i.e., progression of the disease is halted or at least slowed). Methods of measuring these indicators are known to those of skill in the art and/or are described herein. Treatment includes any treatment of a acute kidney injury disease in an individual or an animal (some non-limiting examples include a human, or a mammal) and includes: (1) inhibiting the disease, e.g., arresting, or slowing the progression of acute kidney injury or acute kidney injury complications; or (2) relieving the disease, e.g., causing regression of symptoms, e.g., normalizing or reducing urine creatinine levels; and (3) preventing or reducing the likelihood of the development of a further acute kidney injury complication, or the need for administration of a further treatment, such as for example, a renal transplant.

In some embodiments of these methods and all such methods described herein, the method further comprises administering to the subject an additional therapeutic agent, in addition to the inhibitor of Bax-NPM complex formation or NPM peptide as described herein. Such an additional therapeutic agent can be co-administered with the inhibitor of Bax-NPM complex formation or NPM peptide. As used herein, the phrase "co-administering" or to "co-administer" means the administration of an inhibitor of Bax-NPM complex formation or NPM peptide inhibitor described herein and another compound, e.g., a therapeutic agent, separately, simultaneously, and/or sequentially over a period of time as determined by a qualified care giver.

In some such embodiments, the additional therapeutic agent is an angiotensin-converting enzyme (ACE) inhibitor, an angiotensin II receptor blocker (ARB), or a mineralocorticoid receptor (MR) antagonist.

ACE inhibitors for use with an inhibitor of Bax-NPM complex formation or NPM peptide described herein include, but are not limited to, benazepril (marketed in the U.S. as LOTENSIN™), captopril (marketed in the U.S. as CAPOTEN™), enalapril/enalaprilat (marketed in the U.S. as VASOTEC™ oral and injectable), fosinopril (marketed in the U.S. as MONOPRIL™), lisinopril (marketed in the U.S. as ZESTRIL™ and PRINIVIL™), moexipril (marketed in the U.S. as UNIVASC™), perindopril (marketed in the U.S. as ACEON™), quinapril (marketed in the U.S. as ACCUPRIL™), ramipril (marketed in the U.S. as ALTACE™), and trandolapril (marketed in the U.S. as MAVIK™). ARBs for use with the ROBO2 inhibitors described herein include candesartan (marketed in the U.S. as ATACAND™), irbesartan (marketed in the U.S. as AVAPRO™), olmesartan (marketed in the U.S. as BENICAR™), losartan (marketed in the U.S. as COZAAR™), valsartan (marketed in the U.S. as DIOVAN™), telmisartan (marketed in the U.S. as MICARDIS™), and eprosartan (marketed in the U.S. as TEVETEN™).

In some embodiments of these methods and all such methods described herein, the method further comprises administering to the subject an effective amount of a diuretic, in addition to an inhibitor of Bax-NPM complex formation or NPM peptide. Diuretics include, but are not limited to, torsemide (marketed in the U.S. as DEMADEX™), furosemide (marketed in the U.S. as LASIX™), bumetanide (marketed in the U.S. as BUMEX™), ethacrynic acid (marketed in the U.S. as EDECRIN™), torsemide (marketed in the U.S. as DEMADEX™), amiloride, (marketed in the U.S. as MIDAMOR™), acetazolamide (marketed in the U.S. as DIAMOX™), pamabrom (marketed in the U.S. as AQUA-BAN™), mannitol (marketed in the U.S. as ARIDOL™ or OSMITROL™), traimterene (marketed in the U.S. as DYRENIUM™), spironolactone (marketed in the U.S. as ALDACTONE™), amiloride (marketed in the U.S. as MIDAMOR™), indapamide (marketed in the U.S. as LOZOL™), hydrochlorothiazide (marketed in the U.S. as HYDRODIURIL™) metolazone (marketed in the U.S. as ZAROXOLYN™ or MYKROX™), methylclothiazide (marketed in the U.S. as AQUATENSEN™ or ENDURON™), hydrocholorthiazide (marketed in the U.S. as AQUAZIDE H™ or ESIDRIX™ or MICROZIDE™), chlorothiazide (marketed in the U.S. as DIURIL™) bendroflumethiazide (marketed in the U.S. as NATURETIN™), polythiazide (marketed in the U.S. as RENESE™), hydroflumethiazide (marketed in the U.S. as SALURON™), and chlorthalidone (marketed in the U.S. as THALITONE™). For a complete listing also see, e.g., Physician's Desk Reference, 2012 Edition, PDR Network (2011).

An effective amount for the treatment of a disease means that amount which, when administered to a mammal in need thereof, is sufficient to result in effective treatment as that term is defined herein, for that disease.

G. Determination of Stress-Induced Phosphorylation of NPM for Determining Chemotherapy Efficacy and Toxicity.

In the research context, embodiments of the invention may provide a method for drug screening and reporting of drug effects in preclinical and clinical trials. The diagnostic methods disclosed herein can be used to identify which subjects are being effectively treated with a cancer treatment or chemotherapy, assess the effectiveness of cancer treatment or chemotherapy in a population of subjects, improve the quality and reduce costs of clinical trials, improve therapeutic success rates, and/or reduce sample sizes, trial duration and costs of clinical trials.

In particular, in one embodiment measuring NPM phosphorylation and cell localization are useful to predict the severity and prognosis of acute tissue injury, and that NPM leakage into blood and/or urine represents a novel measure of acute cell death (a primary and desirable endpoint) in cancer patients. In some embodiments, detection of NPM phosphorylation states as well as presence of urinary NPM (and well as determining its phosphorylated from) can be used for titration of chemo- and radiation therapies. In some instances, detection of urinary NPM can be used to determine if the subject should discontinue the nephrotoxic medications (including cancer treatments) or limit procedures in which renal ischemia predictably occurs. In another instance, the leakage of NPM or phospho-NPM into the serum can be used as a biomarker of myocardial infarction (MI) and/or ischemic stroke and can be used to determine the severity and/or prognosis of each.

In some embodiments, the diagnostic assays and methods disclosed herein for detecting the different NPM phosphorylation states us useful to titrate chemotherapy and radiation to improve treatment efficacy. In some embodiments, measuring urinary NPM leakage can be used to tract the suitability of donated kidneys for transplantation. In some embodiments, detection of urinary NPM, including the phosphorylation states of the NPM polypeptide can be used to guide the discontinuation of nephrotoxin medications (e.g., antibitoics, etc.) and predict tissue injury during procedures in which renal ischemia is predicted (e.g., bypass procedures). In some embodiments, detection of NPM staining and phosphorylated forms of NPM polypeptide in renal biopsy samples is useful for diagnosis and prognosis of acute tubular injury and other forms of AKI (acute kidney injury). In some embodiments, detection of NPM mutations in diverse cancer types can be used to predict sensitivity to chemotherapy and/or radiation.

Accordingly, one can use the diagnostic methods and kits disclosed herein for determining the effectiveness of cancer treatment and/or anticancer agents by determining the phosphorylation state of the NPM polypeptide in urine from the subject, at any time before, during and after anti-cancer treatments. If the cancer treatment appears excessively toxic, one can stop or decrease the cancer treatment. Alternatively, if the cancer treatment is not appearing effective, a different cancer treatment can be selected and/or the dose of the anti-cancer agent can be increased. Exemplary methods described in U.S. Pat. No. 7,344,829, which is incorporated herein in its entirety by reference, to titrate the cancer treatment based can be adapted to the methods disclosed herein based on the detection of the phosphorylation state of the NPM polypeptide.

In the health care context, embodiments of the invention may provide a service to physicians that will enable the physicians to tailor optimal personalized patient therapies. For example, a biological sample taken from a subject can be sent by the pathologist and/or clinical oncologist to a laboratory facility, for example, one such lab is operated by Theranostics Health, LLC. The laboratory may analyze the phosphorylation states of one or more amino acid residues of: T86, S88, T95, T234, S242 of the NPM polypeptide in the biological sample and provide a report to the physician or health care provider. The laboratory may provide the treating pathologist or clinical oncologist with a report indicating if the subject from which the biological sample was taken has, or is at risk of having ischemic stress, kidney injury or AKI as disclosed herein and optionally provide a recommendation on if the subject should be treated for kidney injury, ischemia etc. This may enable a physician to tailor therapy to the individual subject, e.g., prescribe the right therapy to the right patient at right time, provide a higher treatment success rate, spare the patient unnecessary toxicity and side effects, reduce the cost to patients and insurers of unnecessary or dangerous ineffective medication, and improve patient quality of life, eventually making cancer a managed disease, with follow up assays as appropriate. Physicians can use the reported information to tailor optimal personalized patient therapies instead of the current "trial and error" or "one size fits all" methods used to prescribe chemotherapy under current systems. The inventive methods may establish a system of personalized medicine.

Cancer Treatments

Several cancer therapies are known in the art and the use one or more of the various anticancer agents know will comprise in the context of this invention as a cancer treatment. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

A. Chemotherapeutic Agents

The term "chemotherapy" refers to the use of drugs to treat cancer. A "chemotherapeutic agent" is used to connote a compound or composition that is administered in the treatment of cancer. Some examples of chemotherapeutic agents include antibiotic chemotherapeutics such as, Doxorubicin, Daunorubicin, Mitomycin (also known as mutamycin and/or mitomycin-C), Actinomycin D (Dactinomycin), Bleomycin, Plicomycin. Plant alkaloids such as Taxol, Vincristine, Vinblastine. Miscellaneous agents such as Cisplatin, VP16, Tumor Necrosis Factor. Alkylating Agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine. And other agents for example, Cisplatin (CDDP), Carboplatin, Procarbazine, Mechlorethamine, Camptothecin, Ifosfamide, Nitrosurea, Etoposide (VP16), Tamoxifen, Raloxifene, Estrogen Receptor Binding Agents, Gemcitabien, Navelbine, Farnesyl-protein transferase inhibitors, Transplatinum, 5-Fluorouracil, and Methotrexate, Temazolomide (an aqueous form of DTIC), or any analog or derivative variant of the foregoing. Table 1 in U.S. Pat. No. 7,344,829, which is incorporated herein in its entirety, lists numerous chemotherapeutics and their use in different cancer types.

Several chemotherapeutic agents change the phosphorylation state of growth factor receptors in cancer cells. For example the protein kinase inhibitor PKI166 decreases the amount of phosphorylated EGFR in cancer cells, which is indicative of tumor shrinkage and decrease of metastasis. Thus, protein kinase inhibitor drugs are another major class of chemotherapeutic compounds important in the context of the present invention.

B. Radiotherapeutic Agents

Radiotherapeutic agents include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these agents effect a broad range of damage DNA, on the precursors of DNA, the replication and repair of DNA, and the assembly and maintenance of chromosomes.

Radiotherapeutic agents and methods of administration, dosages, etc., are well known to those of skill in the art, and may be combined with the invention in light of the disclosures herein. For example, dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

C. Surgery

Approximately 60% of persons with cancer will undergo surgery of some type, which includes, for example, preventative, diagnostic or staging, curative and palliative surgery. Surgery, and in particular a curative surgery, may be used in conjunction with other therapies, such as the present invention and one or more other agents.

Curative surgery includes resection in which all or part of cancerous tissue is physically removed, excised and/or destroyed. It is further contemplated that surgery may remove, excise or destroy superficial cancers, precancers, or incidental amounts of normal tissue. Treatment by surgery includes for example, tumor resection, laser surgery, cryosurgery, electrosurgery, and miscopically controlled surgery (Mohs' surgery). Tumor resection refers to physical removal of at least part of a tumor. Upon excision of part of all of cancerous cells, tissue, or tumor, a cavity may be formed in the body.

D. Immunotherapeutic Agents

An immunotherapeutic agent generally relies on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (e.g., a chemotherapeutic, a radionuclide, a ricin A chain, a cholera toxin, a pertussis toxin, etc.) and serve merely as a targeting agent. Such antibody conjugates are called immunotoxins, and are well known in the art (see U.S. Pat. Nos. 5,686,072, 5,578,706, 4,792,447, 5,045,451, 4,664,911, and 5,767,072, each incorporated herein by reference). Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

E. Genetic Therapy Agents

A tumor cell resistance to agents, such as chemotherapeutic and radiotherapeutic agents, represents a major problem in clinical oncology. Improvement of the efficacy of one or more anti-cancer agents is possible by combining such an agent with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). Gene therapy agents could encode proteins or antisense molecules that change NPM polypeptide phosphorylation, for example genes encoding growth factors. In the context of the present invention, it is contemplated that gene therapy could be used similarly alone or in conjunction with other anticancer agents and one may determine the efficacy of such a treatment using methods of the present invention.

F. Combination Anticancer Therapies

A variety of cancer therapies such as those described above may be used in context of the present invention. Generally, in order to increase the effectiveness of the cancer therapy, it may be desirable to combine two or more anticancer agents.

Administration of one anticancer agent may precede or follow the other anticancer agent by intervals ranging from minutes to days to weeks. In embodiments where both anticancer agents are administered together, one would generally ensure that a significant period of time did not expire between the time of each delivery. In such instances, it is contemplated that one would administer to a patient both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either agent will be required to achieve complete cancer cure. Various combinations may be employed, where the one anticancer agent is "A" and another is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations also are contemplated an assay of improvement or reduction of phosphorylation state of the NPM polypeptide as described in the present invention can be performed at any stage during these combination treatments to determine the efficacy of the treatment and to readjust the administration of drugs as required.

V. Kits

In further embodiments, the invention provides kits for use in detecting the ischemic-induced phosphorylated form of the NPM polypeptide (i.e., having the phosphorylation status of one or more of pT86, pS88, pT95, nT234, nS242, in biological samples obtained from a subject. Such kits will generally comprise one or more antibodies that have immunospecificity for the phosphorylated NPM polypeptide as described in the present invention.

The kits will thus comprise, in suitable container means, (a) components for preserving the phosphorylation state of the NPM protein in a biological and (b) components for determining the phosphorylation states of one or more amino acid residues of: T86, S88, T95, T234, S242 of the NPM polypeptide.

Kits comprising antibodies, such as site specific anti-phospho antibodies that specifically bind to one or more of pT86, pS88, pT95, pT234, pS242 on the NPM polypeptide, or site specific antibodies which specifically binds to the nT234 or nS242 residues on the NPM polypeptide, are envisioned. In some embodiments, it is contemplated that the antibodies will be those that bind to the ischemic-induced phosphorylated form of the NPM polypeptide (i.e., having the phosphorylation status of one or more of pT86, pS88, pT95, nT234, nS242) in a biological sample. Monoclonal antibodies are readily prepared and will often be preferred.

The immunodetection reagents of the kit may take any one of a variety of forms, including those detectable labels that are associated with, or linked to, the given antibody or antigen itself. Detectable labels that are associated with or attached to a secondary binding ligand are also contemplated. Exemplary secondary ligands are those secondary antibodies that have binding affinity for the first antibody or antigen.

The present invention can further be defined in any of the following numbered paragraphs:

1. A method of treating a subject with ischemia, or a subject after an ischemic injury, the method comprising administering to a subject a composition comprising at least one peptide selected from the group consisting of: Ac-KKKRKV-(βA)-TVTIFVAGVLTASLTIWKKMG-COOH; AC-PKKKRKV-(βA)-TLKMSVQPTVSLGG-FEITPPVVLRLK-COOH (peptide #2) and AC-PKKKRKV-(βA)-ES-FKKQEKTPKTPKGPSSVEDIKAK-COOH (peptide #3), or functional variants thereof 2. A method for inhibiting the formation of a nucleophosmin (NPM)-Bax complex, the method comprising contacting a cell with at least one peptide selected from the group consisting of: Ac-KKKRKV-(βA)-TVTIFVAGVLTASLTIWKKMG-COOH; AC-PKKKRKV-(βA)-TLKMSVQPTVSLGG-FEITPPVVLRLK-COOH (peptide #2) and AC-PKKKRKV-(βA)-ES-FKKQEKTPKTPKGPSSVEDIKAK-COOH (peptide #3), or functional variants thereof.

3. A method for inhibiting stress induced cell death, the method comprising the method comprising contacting a cell with at least one peptide selected from the group consisting of: Ac-KKKRKV-(βA)-TVTIFVAGVL-TASLTIWKKMG-COOH; AC-PKKKRKV-(βA)-TLKMSVQPTVSLGGFEITPPVVLRLK-COOH (peptide #2) and AC-PKKKRKV-(βA)-ES-FKKQEKTPKTPKGPSSVEDIKAK-COOH (peptide #3), or functional variants thereof.

4. A method to inhibit nucleosphosmin (NPM) forming a complex with Bax, the method comprising contacting a cell with an agent which inhibits the phosphorylation of any of T86, S88, T95, T232 or S240, thereby inhibiting the formation of a NPM-Bax complex.

5. A method of treating a subject with ischemia, or having had an ischemic injury, the method comprising administering to a subject a composition comprising an agent which inhibits the phosphorylation of any of T86, S88, T95, T232 or S240, thereby inhibiting the formation of a NPM-Bax complex.

6. A method for inhibiting stress induced cell death, the method comprising contacting a cell with an agent which inhibits the phosphorylation of any of T86, S88, T95, T232 or S240, thereby inhibiting the formation of a NPM-Bax complex.

7. The method of any of paragraphs 4-6, wherein the agent is at least one peptide selected from the group consisting of: Ac-KKKRKV-(βA)-TVTIFVAGVL-TASLTIWKKMG-COOH; AC-PKKKRKV-(βA)-TLKMSVQPTVSLGGFEITPPVVLRLK-COOH (peptide #2) and AC-PKKKRKV-(βA)-ES-FKKQEKTPKTPKGPSSVEDIKAK-COOH (peptide #3), or functional variants thereof 8. The method of any of the above, wherein the peptide is fused to a renal targeting nuclear localization sequence (NSL).

9. The method of any of the above, wherein the peptide is administered within 1-2 days of an ischemic event.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure. The present invention is further illustrated by the following Examples. These Examples are provided to aid in the understanding of the invention and are not construed as a limitation thereof.

EXAMPLES

The examples presented herein relate to the methods, kits, and compositions for diagnosing a subject with ischemic AKI and methods of treatment of ischemic AKI using NPM inhibitor peptides a described herein. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Materials and Methods

Animals

All animals were maintained under the guidance and policies of the Boston University Animal Core facility using National Institutes of Health (NIH) and Institutional Animal Care and Use Committee guidelines. Male and female C57BL/6J mice were purchased from Jackson Laboratory (Bar Harbor, Me.), and they were housed and bred at the Boston University Animal Core facility under license number AN-15024. Four-week-old mice with mature kidneys afford more consistent results with regard to AKI severity and have superior survival after anesthesia. Animas were handled in a manner consistent with the NIH guide for their care and use under Institutional Animal Care and Use Committee approval.

Cell Culture

Primary culture of human donor kidney and murine kidney proximal tubular cells was performed as previously described. 13,24 Briefly, renal cortices were harvested. Individual cortical samples were minced and digested by collagenase IV (1 mg/ml); then, they were plated onto culture dishes in a renal epithelial cell-compatible medium (ATCC PCS-400-030). Cultures of cells that exhibited proximal tubule characteristics were maintained for 5-7 days in 5% $CO_2$ at 37° C.13,24,25 HEK293NT lentiviral packaging cells (System Biosciences, Mountain View, Calif.) were maintained in DMEM with high glucose medium (Life Technologies BRL, Carlsbad, Calif.) containing 10% bovine serum and 10% penicillin-streptomycin at 37° C. in a 5% $CO_2$ incubator. Ischemic Stress In Vitro Exposure to metabolic inhibitors is an established model of ischemic stress that reduces ATP content to, 10% of baseline values until recovery is initiated.24,26 To achieve ATP depletion, cells were washed three times in glucose-free DMEM (Invitrogen, Carlsbad, Calif.) followed by incubation in glucose-free DMEM containing sodium cyanide (5 mM) and 2-deoxy-glucose (5 mM) for the indicated times.26

Recovery was initiated by replacing the stress medium described above with complete primary cell culture medium containing glucose and substrates that support the rapid restoration of cell ATP.27

In Vivo

Mice were subjected to bilateral renal pedicle clamping after being anesthetized with 2,2,2-tribromoethanol. A midline laparotomy was performed, and nontraumatic vascular clamps were placed on both renal pedicles for 25-30 minutes, an insult that produces severe AKI.13,28,29 Slight variation in the clamp time was required to achieve similar degrees of renal dysfunction in the relatively large number of animals studied. The clamp was then removed, and reperfusion was confirmed by visual inspection of the kidneys. Sham ischemia was performed by encircling each renal pedicle with a nonocclusive ligature. The first postischemic urine was collected by gentle compression of the inferior abdominal wall.

Hypoxic Stress

To simulate insults encountered during clinical AKI, PTECs were maintained under hypoxic conditions for 70 minutes as previously described, and this is sufficient to induce cell death.15 Briefly, cells were washed with PBS, transferred to a sealed anaerobic chamber filled with 95% nitrogen and 5% CO2 and incubated in Krebs-Ringer bicarbonate buffer (catalog no. k4002; Sigma-Aldrich). This buffer was pre-equilibrated with 95% nitrogen and 5% CO2.

Human Kidneys

Samples of renal cortex were harvested for primary cell culture, and assessment of cytosolic NPM content from paired, non-transplantable human kidneys in transportable chambers perfused with chilled University of Wisconsin machine preservation solution at 4° C. was performed.30 In both kidney pairs, one kidney was normally perfused, whereas the other experienced perfusion failure and was, therefore, subjected to a prolonged period of warm ischemia.

Mapping of NPM Phosphorylation Sites by Mass Spectrometry

NPM was purified from human and murine primary renal cells and fresh kidney tissue homogenates as well as control and postischemic urine by immunoprecipitation using an established method.13 Enzyme digestion with glutamic acid and/or trypsin was performed to obtain fragments appropriate for subsequent analysis. Tandem mass spectrometry spectra obtained by fragmenting a peptide by collision-induced dissociation were acquired using a capillary liquid chromatography/tandem mass spectrometry system that consisted of a Surveyor HPLC pump, a Surveyor Micro AS autosampler, and an LTQ linear ion trap mass spectrometer. Detection and mapping of phosphorylation sites was achieved by database searching of tandem mass spectra of proteolytic peptides with specified phosphate modification (P=+80 D) on serine, threonine, and tyrosine residues against the current mouse and human protein databases. A detailed liquid chromatography/tandem mass spectrometry approach for phosphoproteomics has been previously described.31-33

Mass spectrometry was performed in primary human and renal cells at baseline and after simulated ischemic stress, in fresh human and murine kidney tissue homogenates before and after frank ischemia, and in human and murine urine from patients without AKI and patients with AKI before and after experimental AKI, respectively. At least three replicates of each purified NPM sample harvested from renal cells, kidney tissue, and fresh urine were subjected to mass spectrometry.

NPM Phosphomutant Construction and Infection

Human NPM cDNA (catalog no. 34553; Addgene, Cambridge, Mass.) and pCDH lentivector systems (System Biosciences, Mountain View, Calif.) were used to generate NPM wild-type, "NPM stress mimic" (T86E-S88E-T95E-T234A-S242A), and "NPM normal mimic" (T86A-S88A-T95A-T234E-S242E) lentiviral expression plasmids by PCR-based mutagenesis with a flag tag fused to the 59 open reading frame. PCR products were cloned into pCDH vector BamHI/EcoRI sites. All constructs were confirmed by DNA sequencing before cotransfection with pPACKG1 lentivector packaging plasmids into HEK293NT cells to generate lentipseudoviral particles. The resultant pseudoviruses were harvested and purified, and titers were determined according to the manufacturer's instructions. Cells were exposed to virus (MOI: 5-8) diluted in Opti-MEM (Invitrogen). After 6 hours incubation with virus-infected medium, a complete culture medium was substituted for an additional 16-hour incubation period.

NPM Knockdown

Clustered regularly interspaced short palindromic repeats (CRISPR) interference was used to transiently suppress NPM. After 60 hours under routine cell culture conditions, primary cells were transfected with two sgRNA targeting adjacent to the NPM transcription start site (synthesized by Synthgo, Menlo Park, Calif.) using TranslT-2020 Transfection Reagent using the manufacturer's protocol. Six hours later, five MOI of dcas9-KRAB lentivirus (catalog no. k204; abm.com, Richmond, BC, Canada) were added. The medium was then changed, and culture continued for 48 hours. The magnitude of NPM suppression was assessed by immunoblot analysis.

Dot Blot Analyses

Because relatively low NPM concentrations in urine are insufficient for routine immunoblot due to volume limitations of sample loading, a dot blot assay standard method and protocol were used (http://www.abcam.com/ps/pdf/protocols/dot %20blot %20protocol.pdf). In the dot blot assay, NPM can be easily detected, because a much larger urine volume can be loaded. Importantly, identical anti-NPM antibodies were used in both the immunoblot and dot blot assays.

Renal-Targeted NPM Peptides

For in vitro testing in primary human PTECs, peptides (200 mM) were tested that replicate the Bax domain responsible for binding NPM, 34 or two peptides designed to interfere with NPM function were compared with a random nonspecific sequence of the same length (control). Peptides intended to interfere with NPM function overlap key phosphorylation sites located at the NPM amino terminus (peptide 2) or carboxy terminus (peptide 3) detected by mass spectrometry. To improve cell uptake, all peptides contained a cell-penetrating sequence 13. For in vivo experiments, a renal-targeting sequence (NLS) was added to enhance renal peptide uptake.35 Peptides were commercially synthesized (Biomatik, Wilmington, Del.) J Am Soc Nephrol 30: ccc-ccc, 2018 Nucleophosmin in AKI 3www.jasn.org BASIC RESEARCHas follows: NPM-Bax blocking peptide: Ac-KKKRKV-(bA)-TVTIFVAGVLTASLTIWKKMG-COOH (SEQ ID NO: 8); peptide 2: AC-PKKKRKV-(bA)-TLKMSVQPTVSLGGFEITPPVVLRLK-COOH (SEQ ID NO: 9); and peptide 3: AC-PKKKRKV-(bA)-ESFKK-QEKTPKTPKGPSSVED-IKAK—COOH (SEQ ID NO: 10). A single dose (100 mg/g body wt of the NPM-Bax blocking or control peptide) was administered by tail vein injection immediately after release of the pedicle clamps (0 timepoint) as well as 1, 2, 3, 4, 5, and 6 hours later in each experimental group. A total of 42 control and 56 experimental animals were studied.

Cell Viability or Kidney Function

Transient exposure to metabolic inhibitors replicates ischemia in vivo by activating Bax and causing cell death.13, 29,36-38 Cell viability was assayed using a modified colorimetric technique (MTTassay).37 The number of surviving cells is expressed as a percentage of viable control cells detected at baseline. Serum BUN and creatinine levels were measured in tail vein blood samples for 7 days after ischemia using QuantiChrom BUN or creatinine assay kits (BioAssay Systems, Hayward, Calif.) according to the manufacturer's instructions.

Protein Isolation and Immunoprecipitation

Cell, tissue, and urinary proteins were harvested using PD buffer containing 40 mM Tris-HCl, pH 8.0, 500 mM NaCl, 0.1% Nonidet P-40, 6 mM EGTA, and a protease inhibitor cocktail (Set I; Calbiochem, San Diego, Calif.). NPM was immunoprecipitated overnight with NPM antibodies (catalog no. B0556; Sigma-Aldrich) in the presence of protein A/G-agarose beads at 4° C. NPM accumulation was measured in cytosolic samples extracted with low-dose digitonin (8 mg/ml).13 Cytosolic proteins were extracted from renal cortical tissue samples using an extraction kit (Biochain Institute, Newark, Calif.). Briefly, 50-100 mg of kidney cortex tissue was minced on ice and spin washed with 1 ml ice-cold wash buffer before adding 100-200 ml of buffer C. The mixture was rotated at 4° C. for 20 minutes and then centrifuged at 18,0003 g at 4° C. for 20 minutes before being harvested. Protein levels were measured with the bicinchoninic acid assay (Thermo Scientific, Rockford, Ill.).

Immunohistochemistry

NPM was visualized as previously reported, 13 and the protocol was performed according to the manufacturer's protocol (catalog no. B0556).

Dot Blot Assay

NPM was detected in murine urine using a dot blot assay as previously reported 39 using an antibody directed against total NPM.

Statistical Analyses

Data are expressed as means with SEM. Differences between groups were determined by a two-tailed t test using Excel (Microsoft, Redmond, Wash.). Comparisons involving more than two groups were determined by a two-way ANOVA followed by a Holm-Sidak post hoc test for nonparametric data. P, 0.05 was considered significant.

Example 1

Stress Causes NPM Translocation in Both Cells and Tissues

Figure 1C:
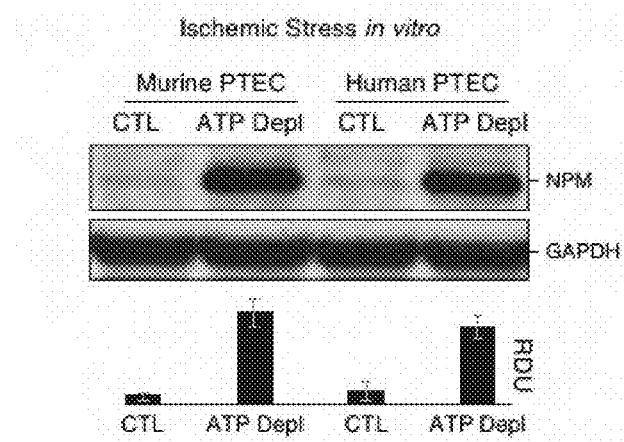
Figure 1B:
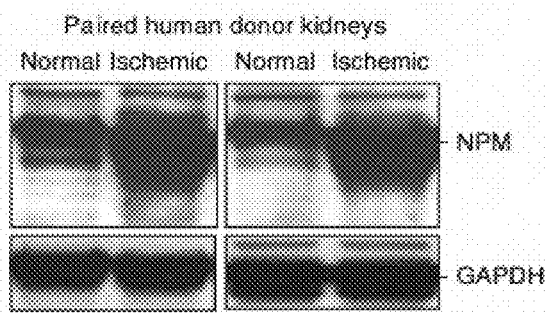

NPM translocation from the nucleus to the cytosol promotes cell death.40,41 To determine the extent to which ischemic stress causes NPM translocation, an early step in the NPM-mediated death pathway, 42 PTECs were subjected to transient ATP depletion, an established model of metabolic stress that resembles ischemia.24,26 In resting primary human PTECs, 0.95% of total cell NPM localized to the nuclear (i.e., noncytosolic) fraction. In contrast, about 15% of total cell NPM accumulated in the cytosol after stress. Compared with normal cells, only about 80% of NPM remained intracellular (15% cytosolic plus 65% nuclear) (FIG. 1A), demonstrating that extracellular NPM leakage or NPM degradation occurred. Stress caused marked cytosolic NPM translocation in ATP depleted primary murine PTECs (FIG. 1B) or renal homogenates harvested from grossly ischemic, nontransplantable human kidneys ex vivo compared with well perfused kidneys harvested from the same donor (FIG. 1C).

Figure 1D:
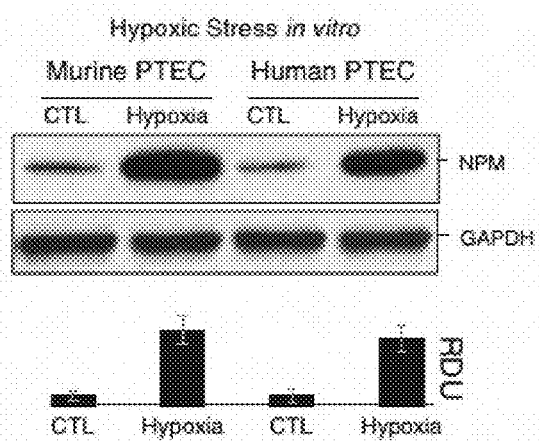

Cytosolic NPM translocation was also detected in murine and human primary PTECs after transient hypoxia (FIG. 1D). Densitometric analysis confirmed the magnitude and reproducibility of NPM translocation. Both de-energization and hypoxia contribute to renal epithelial cell injury and organ failure during human AKI.3

Stress Induces Site-Specific NPM Phosphorylation Changes

To identify the post-translational events that regulate NPM toxicity, the effect of metabolic stress on differential NPM phosphorylation was examined by mass spectrometry in purified NPM harvested from human and murine kidney cortex and human and murine primary PTECs after ischemic stress as well as after murine and human AKI. Representative tracings are shown (FIG. 2A-2C). Digestion of NPM from cells and tissue with trypsin and glutamic acid afforded positive identification of 269 of 292 (92%) potential NPM residues and yielded 100% all known serine, tyrosine, and threonine residues capable of undergoing ischemia-induced phosphorylation or dephosphorylation. Despite a two-amino acid difference in overall length, the amino acid sequences are >94% similar in murine and human NPM, and the phosphorylation consensus sequences are identical. Compared with control renal tissue and cells, five distinct phosphorylation changes at T86, S88, T95, T234, and S242 were observed after ischemic stress (FIG. 2D). Remarkably, only a single event (dephosphorylation at T86 in murine kidney tissue) differed from site-specific phosphorylation changes detected in other cell or tissue samples subjected to ischemic stress. The pattern of urinary NPM phosphorylation identically matched phosphorylation at four of five serine/threonine residues detected in ischemic cells and renal tissue (FIG. 2D). Only the peptide fragment containing S240 was not detected in NPM purified from postischemic murine urine. In a patient with Kidney Disease Improving Global Outcomes criteria for stage 3 AKI, 43 differential phosphorylation at residues T86, S88, and S242 was detected (FIG. 2D). The pattern of NPM phosphorylation in human urine during AKI resembled NPM phosphorylation changes in ischemic cells, tissue, and murine urine after experimental AKI. Total NPM was readily detected in murine urine within 6 hours after renal ischemia and disappeared within 48 hours after injury (FIG. 3)

NPM Phosphomimic Proteins Mediate NPM Toxicity

Figure 5A:
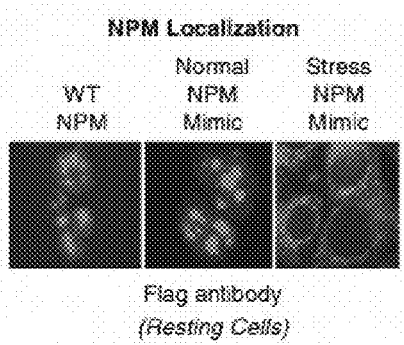
FIGS. 5A-5E shows phosphomimic nucleophosmin (NPM) proteins that replicate stress-induced phosphorylation changes regulate NPM toxicity. The biologic behavior of nucleophosmin (NPM) phosphomimic proteins assessed using functional bioassays performed in primary murine proximal tubule epithelial cells (PTECs) that express flagtagged wild type (WT), a normal (Nor-M or NrNPM) NPM mimic protein, or a stress (Stre-M, StNPM, or Stress-M) NPM mimic protein that replicates differential NPM phosphorylation.
Figure 5B:
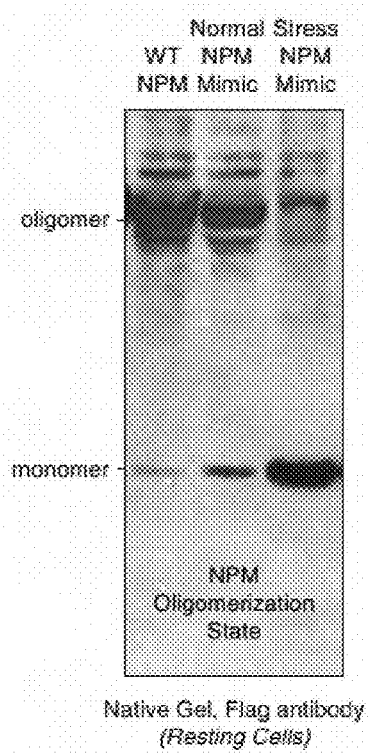
Figure 5C:
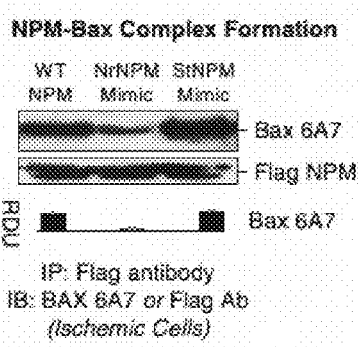
Figure 5D:
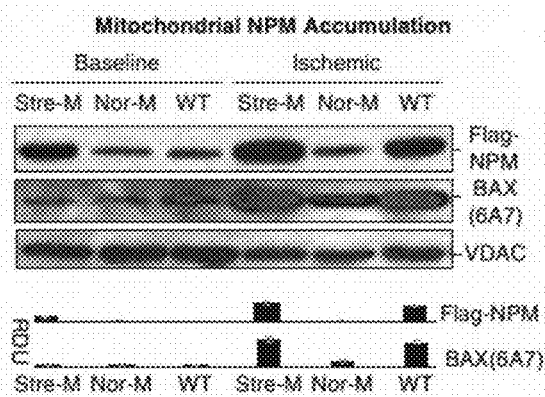

To determine the biologic role of differential NPM phosphorylation at these five serine/threonine sites and the contribution to cytotoxicity, two flag-tagged NPM phosphomutant proteins as well as wild-type NPM were generated and introduced into human proximal tubule cells. These two mimic proteins replicated the phosphorylation state of NPM in either its normal or stressed configuration at the five differentially phosphorylated sites identified by mass spectrometry (FIG. 4). Specific bioassays were then used to assess the effect of these five post-translational phosphorylation changes on toxic NPM behaviors, including translocation, deoligomerization, NPM-Bax complex formation, mitochondrial NPM and Bax accumulation, and cell death. Both the wild-type and normal NPM phosphomimic proteins accumulated in a nucleolar pattern within resting cells (FIG. 5A, left and center panels). In contrast (and in the absence of ischemic stress), only the NPM stress mimic protein localized to the cytosol (FIG. 5A, right panel). In resting cells, wild-type and normal mimic NPM formed large oligomers. In contrast, the stress mimic NPM protein accumulated as small monomers known to interact with conformationally active Bax (FIG. 5B). After ATP depletion sufficient to activate Bax, NPM-Bax complex formation was substantially greater in cells that contained stress mimic NPM (FIG. 5C). Similarly, the accumulation of both stress mimic NPM and active Bax accumulation in isolated mitochondria after ischemic stress exceeded that observed with wild-type or normal mimic NPM (FIG. 5D). Compared with control or cells that expressed either empty vector (an added transfection control) or wild-type NPM, postischemia survival was significantly lower in cells containing stress mimic NPM (FIG. 5E) (P, 0.05). Unexpectedly, normal mimic NPM expression significantly reduced cell death (P, 0.05). Compared with wild-type NPM, the expression of normal mimic NPM also decreased NPM-Bax complex formation (FIG. 5C) and the accumulation of NPM and Bax in isolated mitochondria after ischemic stress (FIG. 5D).

Example 2

NPM is a Relevant Target for Ameliorating Renal Cell Injury

Figure 6:
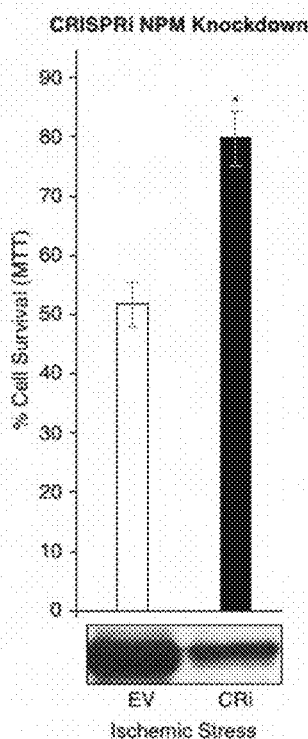
FIG. 6 shows nucleophosmin (NPM) suppression increases proximal tubule epithelial cell (PTEC) survival after ischemic stress. An inducible clustered regularly interspaced short palindromic repeats-based system suppressed NPM expression after doxycycline exposure (Cri; 2 mg/ml 372 hours; inset) versus empty sgOpti vector (EV; inset). NPM suppression significantly improved human PTEC survival after 60 minutes of ATP depletion. CRISPRi, clustered regularly interspaced short palindromic repeats interference. *P, 0.05 EV versus Cri (n=4).

To assess the causal role of NPM in renal cell death, primary human PTECs were subjected to ischemic stress before and after NPM knockout using an inducible CRISPR system. CRISPR reduced NPM expression by 80%-90% (FIG. 6, inset) and significantly increased cell survival after ischemia (FIG. 6).

Figure 7:
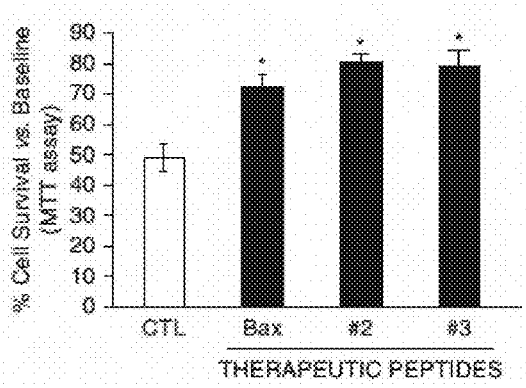
FIG. 7 shows therapeutic peptides improve renal cell survival after ischemic stress. Peptides designed to reduce nucleophosmin (NPM)-Bax complex formation (Bax peptide) (SEQ ID NO: 1) or interfere with phosphorylation changes that regulate NPM toxicity (peptides #2 (SEQ ID NO: 2) and #3 (SEQ ID NO: 3)) significantly improve cell survival after ischemic stress (n=4; upper panel). Peptide 2 replicates regulatory phosphorylation sites located at the amino terminus (T86, S88, and T95). Peptide 3 replicates regulatory phosphorylation sites located at the carboxy terminus (T234 and S242). The amino acid sequences of each of the three peptides designed to interfere with NPM function are shown (lower panel). *P, 0.05 versus control peptide (CTL).
Figure 8A:
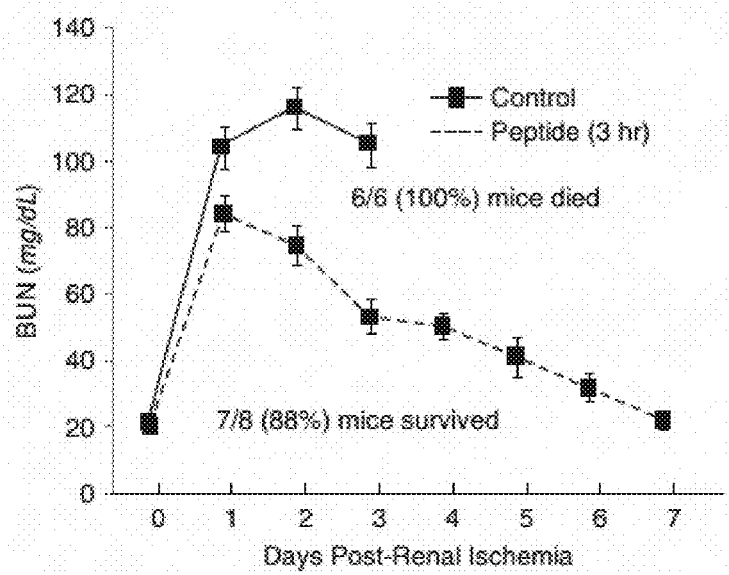
FIGS. 8A-8B show therapeutic peptide treats ischemic AKI.
Figure 8B:
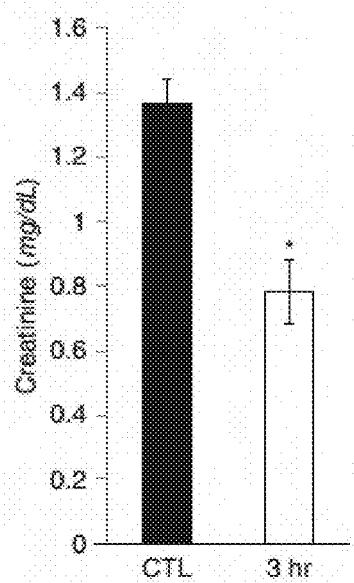
Figure 9A:
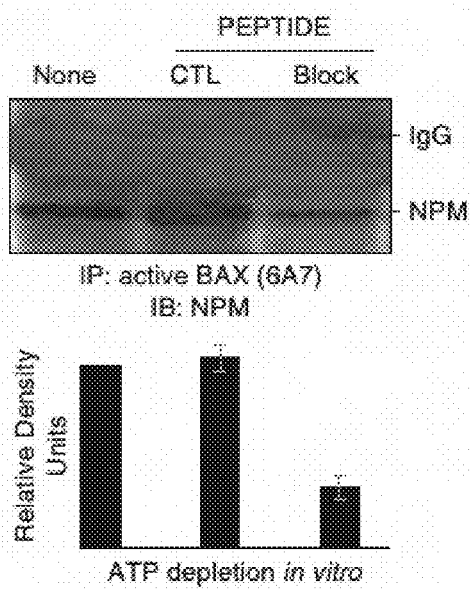
FIGS. 9A-9B shows that the NPM-Bax blocking peptide (Peptide #1) decreases nucleophosmin (NPM)-Bax interaction.
Figure 9B:
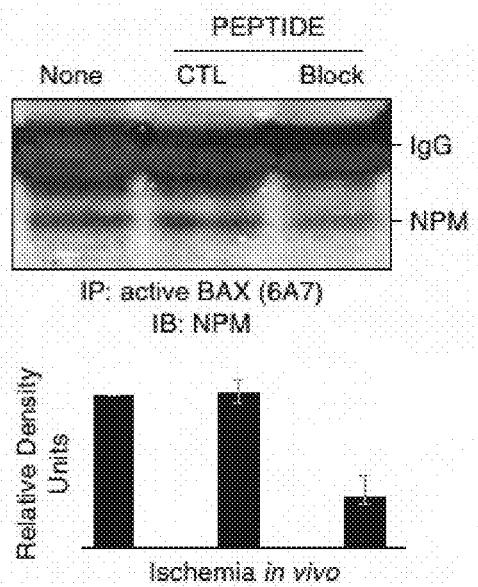

Cell and Animal Survival after Ischemic Stress is Improved by Peptides Designed to Interfere with NPM Function Identification of the key events that regulate NPM cytotoxicity raised the possibility that peptides designed to interfere with stress-induced NPM phosphorylation or NPM-Bax complex formation might have therapeutic potential. To test this hypothesis, peptides that replicate the phosphorylation consensus sequences altered by ischemic stress (FIG. 2D) at the NPM amino (amino acids 78-103) or carboxy termini (amino-acids 226-246) or likely to interfere with NPM-Bax complex formation 34 were generated and tested. After introduction into human PTECs, all three peptides significantly improved post-ischemic cell survival (FIG. 7). To assess its efficacy in treating severe ischemic AKI, a single peptide dose was intravenously administered to mice 0-3 hours after releasing bilateral renal pedicle clamps after 28 minutes of ischemia, an insult sufficient to induce lethal organ failure. All control mice that received a random peptide (six of six) died within 72 hours after pedicle clamp release (FIG. 8A). Before death, these animals had BUN concentrations that averaged 120 mg/dl, a marked degree of azotemia. In contrast, animals receiving a single dose of a renal targeted peptide designed to interfere with Bax-NPM complex formation exhibited significantly lower BUN levels and less severe organ failure on days 1-7 post-ischemia. Peptide treatment also reduced serum creatinine by nearly 50% on day 1 post-ischemia, a time point associated with marked BUN accumulation (FIG. 8B). Remarkably, seven of eight peptide-treated animals (88%) survived severe ischemic AKI. Peptide administration at 0, 1, or 2 hours post-ischemia also provided significant protection against lethal renal ischemia (P, 0.05 versus control), but no protection was observed if the same peptide dose was administered 4, 5, or 6 hours after transient renal ischemia (P.0.05) (Table 4). In peptide-treated animals, recovery of renal function was complete, and it was sustained for at least 4 weeks. Blocking peptide treatment markedly reduced Bax-NPM interaction in renal epithelial cells in vitro (FIG. 9A) as well as postischemic renal homogenates (FIG. 9B).

TABLE 4

Renoprotective effect of peptide therapy for AKI. Summary of animal survival data after transient renal ischemia; experimental conditions were identical to those described in FIG. 8. A single dose of blocking peptide or a control peptide was administered at 0, 1, 2, 3, 4, 5, and 6 h after AKI induction. Animal deaths were presumed due to AKI, and they were recorded for 7- d post-pedicle clamp release; no deaths were observed after 3 d. Significant protection by the blocking peptide on animal survival was observed for doses administered at 0, 1, 2, or 3 h post-AKI (P, 0.05); the blocking peptide was not protective if administered at 4, 5, or 6 h post-AKI (P.0.05).

| Days (Post-AKI) | Peptide Treated, n = 8 Animals at Each Time Point (Dose Post-AKI, h) | | | | | | | Control, n = 6 Animals at Each Time Point (Dose Post-AKI, h) | | | | | | |
|---|---|---|---|---|---|---|---|---|---|---|---|---|---|---|
| | 0° | 1° | 2° | 3° | 4° | 5° | 6° | 0° | 1° | 2° | 3° | 4° | 5° | 6° |
| 1 | 1 | 1 | | | 1 | 1 | 1 | 2 | | 1 | 1 | 1 | 2 | 1 |
| 2 | | 1 | 1 | 1 | 4 | 6 | 4 | 4 | 3 | 4 | 2 | 3 | 4 | 4 |
| 3 | | | | 3 | | 2 | | | 3 | | 3 | 2 | | |
| Total deaths | 1 | 2 | 1 | 1 | 8 | 7 | 7 | 6 | 6 | 5 | 6 | 6 | 6 | 5 |
| Survival, % | 88 | 75 | 88 | 88 | 0 | 13 | 13 | 0 | 0 | 17 | 0 | 0 | 0 | 17 |

Example 3

Herein, the inventors have discovered that post-translational modifications convert NPM from a highly conserved protein that is essential to cell survival to a cytotoxin and demonstrate that these post-translational phosphorylation changes link early AKI diagnostics with effective therapeutics. Mass spectrometry of purified NPM reveals five distinct serine/threonine sites that regulate NPM toxicity during ischemic stress in both primary renal cells and intact tissues of two genetically divergent mammals, showing conservation of this mediator in the stress-induced cell death pathway. Expression of an NPM phosphomimic protein that replicates the differential phosphorylation changes detected in primary renal cells, tissue, and urine after an ischemic insult reproduces NPM translocation and deoligomerization, key behaviors of the wild-type NPM observed during ischemic stress. Interestingly, two of five phosphosites identified in herein (S88 and T95) also regulate NPM deoligomerization and cytosolic translocation in human cancer cells, respectively, 40,41 and they determine responsivity to therapy in patients with acute myelogenous leukemia by enhancing their sensitivity to chemo- and radiation-induced apoptosis.44,45

Figure 5E:
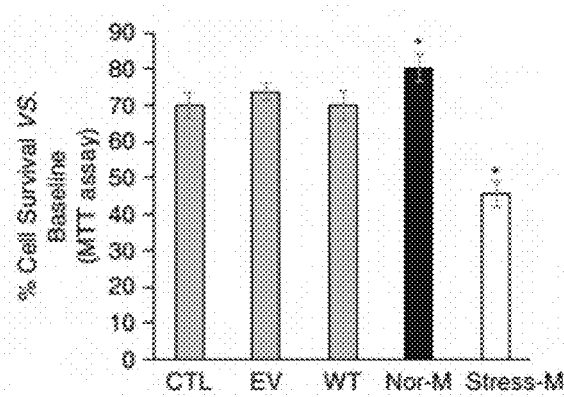

Semi-quantitative analysis of peptide abundance by mass spectrometry revealed that >80% of cytosolic NPM was differentially phosphorylated in the toxic pattern after stress. Thus, the inventors have demonstrated that differential phosphorylation positively correlates with translocation to the cytosol. In addition to S88 and T95, the inventors have also discovered three other stress-induced differential phosphorylation changes that regulate NPM toxicity in ischemic renal cells (outlined in FIG. 10). The proposed intracellular events are on the basis of the discovery that the NPM phosphomimic protein (with all five stress-induced phosphorylation changes) undergoes (1) cytosolic NPM translocation (FIG. 1 and FIG. 5A), (2) deoligomerization of large NPM pentamers to monomers capable of traversing the nuclear pore 46 (FIG. 5B), (3) complex formation with conformationally activated Bax (FIG. 5C), and (4) coaccumulation with Bax in isolated mitochondria (FIG. 5D) and cell death (FIG. 5E).

Alterations in NPM phosphorylation alone, even in the absence of cell stress, are sufficient to cause cytosolic NPM accumulation and deoligomerization. In contrast, NPM-Bax complex formation and mitochondrial NPM-Bax accumulation require both site-specific NPM phosphorylation changes and stress-induced conformational Bax activation. The inventors previously reported that mitochondrial Bax accumulation is NPM dependent 13 and that the NPM-Bax complex forms only after Bax undergoes conformational activation, 13,34,47 exposing the amino-terminal 6A7 epitope.48,49 Although increasing cytosolic NPM significantly promotes Bax-mediated cell death, increasing cytosolic NPM per se is nontoxic.13 These inventors demonstrate herein that both NPM and Bax are both required to cause stress-induced cell death, and they are analogous to Knudson "two-hit hypothesis" of cancer cell transformation.50 In a biologic twist of fate, Bax has also been implicated in releasing nuclear NPM into the cytosol, 51 further linking their toxic behaviors. Effective reagents in our experimental models are likely to be therapeutic for Baxmediated renal injury in humans, because virtually identical post-translational NPM modifications at identical consensus sequences were detected in ischemic murine and human cells and tissue and were partially replicated in urine during clinical and experimental AKI.

Several laboratories have reported that Bax-regulating kinases, including protein kinase B (Akt13,52), glycogen synthase kinase 3b13,53, and Jun N-terminal kinase, 54 activate Bax. In renal cells, conformational Bax activation is primarily due to the loss of Akt-mediated Bax serine 184 phosphorylation during ischemic stress.13 Surprisingly, the normal NPM phosphomimic protein significantly improved cell survival after stress. This is likely due to the fact the normal phosphomimic protein inhibited both stress-induced NPM-Bax complex formation (FIG. 5C) and NPM-Bax accumulation in isolated mitochondria (FIG. 5D) compared with either the wild-type or stress mimic NPM. Accordingly, the inventors have demonstrated herein that the normal NPM phosphomimic mutant protein acts as a competitive inhibitor of endogenous NPM and may itself be a therapeutic agent.

Herein, the inventors demonstrate that differential NPM phosphorylation is a potential urinary marker for renal epithelial cell injury as well as an effective target for peptide-based therapeutics directed against NPM. Within hours of renal ischemia (and at the time of first urine collection), both total and phosphorylated urinary NPM are readily detectable. This is more likely due to NPM leakage across the cell membrane than NPM degradation during the brief period of ischemia.13 Herein, the inventors demonstrate using mass spectrometry that urinary NPM exhibits the same pattern of phosphorylation and dephosphorylation as NPM harvested from renal cells and fresh issue. The discovery that both total and phosphorylated NPM are detectable within hours after renal ischemia, well before a rise in serum BUN/creatinine is evident, further validates NPM phosphorylation states as early AKI markers that can be used to initiate effective AKI treatment. Despite marked organ dysfunction, total NPM is no longer detected in urine 48 hours after the insult, demonstrating that it reflects acute renal epithelial cell injury. Although total urinary NPM could result from detached, sublethally injured renal cells, the phosphorylated NPM is specific for lethal cell injury. This is strongly demonstrated herein which shows that wild-type NPM overexpression in renal cells is nontoxic, 13 whereas stress phosphomimic NPM exacerbates ischemic cell death. The magnitude of differential NPM phosphorylation during ischemic stress is uncertain and will likely require quantitative mass spectrometry to be adequately addressed. In biology, it is unusual for protein to exist in a single form, because phosphatase and kinase activity act as opposing forces to regulate protein function.55 On the basis of compelling data gleaned from the phosphoproteomic study and peptide treatment, the inventors have discovered that NPM is a marker of acute renal cell injury that can be physiologically linked to effective AKI treatment.

NPM has been proposed by others to be a Bax chaperone, 34,47 and it is strongly implicated in regulating Bax-mediated ischemic renal cell injury.13 However, herein, the inventors demonstrate that a NPM blocking peptide (e.g., also called a NPM inhibitory peptide) designed to interfere with NPM-Bax interaction decreases NPM-Bax complex formation in vitro and in vivo by about 50% (FIG. 9), improves renal cell survival (FIG. 7), and substantially improves kidney function (i.e., reduced both BUN and creatinine) by 50%. While a single effective inhibitor is likely to afford only partial protection, a cocktail of site-specific peptides directed at multiple steps in the NPM-Bax cell death pathway could improve renoprotection. The discovery that NPM phosphorylation has interdependent regulatory effects on oligomer assembly and protein partner binding 20 (e.g., with Bax) supports the use of multiple reagents. Infact, such stratagies are useful if NPM- and Bax-independent forms of cell death contribute to organ failure after ischemia.56 However, substantial evidence suggests that Bax contributes to the forms of regulated cell death most often detected after renal ischemia, including apoptosis, necrosis, 57-59 and more recently, necroptosis, a biochemically distinct form of cell death.57,60

Inhibitory or blocking Peptides are ideal for treating renal diseases that primarily target the PTEC. Peptides have few untoward side effects partly due to their extremely short serum t1/2.61 Furthermore, peptides that contain the NLS sequence selectively accumulate in the kidney. In fact, 94% of an intravenous radiolabeled peptide attached to the NLS sequence accumulates in the murine kidney.35 It is highly likely the megalin receptor, located on the brush border of the PTEC, mediates renal peptide uptake and markedly prolongs its t1/2.62 Herein, NLS-containing NPM inhibitor peptides of SEQ ID NO: 1-3 were uniquely designed to interfere with separate NPM functions, and were demonstrated to significantly protect cells against ischemic stress (FIG. 7) as effectively as CRISPR-mediated NPM knockdown (FIG. 6). The 20%-30% improvement in cell survival is likely to significantly promote organ recovery by more rapidly replacing cells lost during ischemia, a key determinant of organ recovery after AKI.28,63 In contrast to universally lethal AKI in control, 75%-88% of animals survived after a single dose administration of a NPM inhibitor peptide, administered 0-3 hours after releasing the renal pedicle clamps, demonstrating significant efficacy of the NPM inhibitor peptides in treating ischemic AKI in vivo, which is a disease the presently lacks an effective treatment. Although NPM inhibitor peptide administration did not completely protect against AKI, treatment was sufficient to promote animal survival, equivalent to avoiding RRT in human AKI. The 3-hour therapeutic window for peptide treatment is similar to that reported for thrombolytic treatment in acute myocardial infarction 64 and ischemic stroke, 65 insults in which Bax-mediated apoptosis and necrosis have been reported. 58,66-68 Although relatively narrow, this treatment window exceeds that reported for other forms of programmed cell death in renal ischemiareperfusion injury, including necroptosis, that can only be given before the insult.69

The remarkable efficacy of interfering with a single-cell death pathway is likely due to the facts that (1) Bax-mediated apoptosis and necrosis represent a continuum of cell death rather than distinct pathways 13,70,71,72; (2) cytosolic NPM translocation, deoligomerization, and NPM-Bax complex formation occur before cells are irreversibly committed to die 13,34 (unlike blocking downstream caspases); and (3) renal cell death is partly responsible for the subsequent oxidant injury and inflammation that accompany organ failure.72 As a result, early AKI detection linked with early treatment is especially attractive.

In response to stress, approximately 75%-80% of cell Bax colocalizes with mitochondria without a known mitochondrial localizing sequence 74 or an identified outer membrane receptor, 73 indicates that Bax requires a cytosolic chaperone to target mitochondria. Herein, the inventors have demonstrated that virtually identical phosphorylation changes at specific amino acid residues convert NPM from an essential cytosolic protein to a toxic Bax chaperone in both mice and humans and the phosphorylation state of the NPM polypeptide is an early marker of ischemic renal cell injury and is also a target for therapeutic intervention. The presence of both NPM and Bax in all mammalian cells indicates that this regulatory cascade also participates in tissue injury in other ischemia-susceptible organs.

Example 4

Nucleophosmin (NPM) Phosphorylation States as a Diagnostic for MO and NPM Peptides as Therapeutic Treatment of Subjects with AKI Nucleophosmin (NPM) translocation from the nucleolar region of the nucleus into the cytosol or extracellular compartment (blood or urine) heralds cell death mediated by Bax, a toxic member of the BCL2 protein family that regulates apoptosis and regulated necrosis. Changes in NPM phosphorylation status at 5 specific sites alters NPM function and regulates early steps in the death pathway in mammalian cells subjected to stress. Peptide reagents directed against NPM reduce its toxicity, preserve organ (renal) function, and significantly improve animal survival if administered either before or within 4 hours after an ischemic insult. Similarity between human and murine NPM sequences allows for rapid translation to human disease. Mass spec reveals identical NPM phospho-changes in human and murine cells subjected to ATP depletion as well as in post-ischemic murine and human kidneys. NPM translocates into the cytosol and urinary lumen of proximal tubule cells in biopsy specimens obtained from humans with acute tubular injury and AKI and transiently appears in the urine of mice subjected to ischemic AKI before changes in renal function occurs as measured by traditional BUN/Cr assays. New bioassays will be linked to treatment with novel anti-NPM peptide(s). The inventors use immuneassays, e.g., ELISA to measure both NPM and phospho-NPM in fluids and use site specific phospho-antibodies to detect NPM in various stages of activation that result in renal and non-renal cell death.

The inventors herein have assessed individual labeled NPM phospho-proteins by Mass Spec to assess their contribution to NPM function and cell death in the presence or absence of endogenous NPM. Phospho-specific antibodies allow the phosphorylation status of NPM to be detected in tissues to determine the severity of tissue injury and predict prognosis. In particular, the detection of total nucleophosmin and nucleophosmin phosphorylation status in the blood, urine and human tissues before, during and after ischemic insults can acts as a diagnostic, as well as determines the severity of injury and determines prognosis (likelihood of organ recovery), and also guide therapeutic interventions that minimize cell death and gauge treatment efficacy, e.g., determine therapeutic efficacy of cancer treatments in real time before current clinical tests reveal tissue injury.

The inventors have discovered that the different phosphorylation states of the NPM polypeptide is useful for (1) assessing and testing for acute stress (e.g, ischemia), which is presently unavailable and occurs before current measures of tissue (e.g., kidney), (2) linking NPM diagnostics to NPM inhibitor peptide therapeutics that prevent or treat ischemic injury and kidney injury, and/or NPM mediated cell death, (3) predict the severity and prognosis of acute tissue injury, and (4) detection of NPM leakage into blood and/or urine represents a novel measure of acute cell death (a primary and desirable endpoint) in cancer patients. In an exemplary use, detection of the changes in NPM phosphorylation can be used to predict cell death in non-kidney tissues and blood, as well as AML, prognosis.

Another exemplary use of the diagnostic assays described herein is detection of the phosphorylation state of the NPM polypeptide as a measure of cancer therapy efficacy. For example, monitoring or detecting changes in the phosphorylation state of the NPM polypeptide in blood and urine biological samples can be used as a measure cell death during chemo- or radiation therapy. For example, urinary NPM may be a marker of generalized cell death during chemotherapy and evidence of effective treatment, as well as the pattern of NPM-phosphorylation in urine used to reflect cell killing by apoptosis (near 30 kDa MW filtration cutoff) during cancer treatment.

NPM Peptide Assays & Therapeutics

Small NPM inhibitor peptides (20-30AA size) can be fused to a renal specific cell penetrating peptide to markedly increase renal delivery (90%). The NPM inhibitor peptides are directed at blocking Bax-NPM interaction and/or NPM toxicity related to phosphorylation changes at 5 sites, and a single peptide dose was demonstrated to be effective at preventing ischemic-indiced cell death, and there was no detectable toxicity observed in mice in vivo.

Herein, the inventors have also demonstrated that in a preliminary study, peptide(s) that mimic NPM-phosphorylation sites improve survival in renal epithelial cells subjected to ATP depletion, and that such peptides may be useful for preventing stress-induced cell death in the kidney and other organs.

The inventors also demonstrate use of functional assays that to measure phosphorylation at each of 5 NPM sites alterations, which can be used to assess its toxicity with regard to any one of: NPM nuclear release, de-oligomerization, NPM-Bax interaction, NPM-Bax complex translocation to mitochondria, and mitochondrial injury)

The therapeutic NPM inhibitory peptides directed against NPM are also assessed by their functional role and its relative toxicity determined by distinct NPM assays of site-specific NPM phospho-changes Herein, the inventors demonstrate NPM toxicity is amenable to NPM inhibiting peptides that act that competitive inhibitors and interfere with NPM-Bax interaction (required for cell death) and/or NPM—phosphorylation that mediates toxic NPM behaviors (release from the nucleolar region, oligomerization, cytosolic translocation, interaction with Bax, and migration of the NPM-Bax complex to mitochondria), the primary target of cell death. Since Bax mediates stress-induced cell death in the heart, brain, kidney, liver and bowel it is likely that peptide therapeutics targeted to these organs will ameliorate acute ischemic tissue injury after a myocardial infarction, stroke or after an ischemic insult to the kidney, liver, or bowel. Since NPM is highly conserved in nature, it is likely that multiple stressors and tissues utilize a NPM-Bax mediated cell death pathway. Therefore, maneuvers that interfere with NPM-Bax function are highly likely to be effective therapeutics.

As such, the inventors have discovered that NPM phosphorylation states is useful in diagnostic testing for acute stress (e.g., ischemia) before current measures of tissue (e.g., kidney) injury, and that NPM diagnostics can be linked to treatment using the NPM inhibitors described herein, e.g., the NPM inhibitor peptides that prevent or treat NPM-mediated cell death and prevent or treat tissue injury. Moreover, the inventors have demonstrated that measuring NPM phosphorylation and cell localization are useful to predict the severity and prognosis of acute tissue injury, and that NPM leakage into blood and/or urine represents a novel measure of acute cell death (a primary and desirable endpoint) in cancer patients. In particular, NPM phosphorylation and urinary NPM can be used for titration of chemo- and radiation therapies. In some instances, detection of urinary NPM can be used to determine if the subject should discontinue the nephrotoxic medications (including cancer treatments) or limit procedures in which renal ischemia predictably occurs. In another instance, the leakage of NPM or phospho-NPM into the serum can be used as a biomarker of myocardial infarction (MI) and/or ischemic stroke and can be used to determine the severity and/or prognosis of each.

Example 5

As disclosed in Examples 1-2, the NPM inhibitory peptide (including the renal targeted peptide) decreased NPM-Bax complex formation in the post-ischemic renal cortex in vivo, with improved organ function. This data clearly demonstrates the therapeutic efficacy of antagonizing NPM-Bax interaction during ischemia and invites additional interventions that reduce NPM-Bax toxicity to prevent and treat AKI. Accordingly, the inventors demonstrate that NPM post-translational phosphorylation events alter NPM function and contribute to renal epithelial cell death in ischemic human kidney tissue. Inhibition of the NPM-Bax complex is therefore useful in treating ischemic-induced cell stress and AKI. In particular, detection of total NPM protein and the phosphorylated state of the NPM protein in urine is useful as an AKI biomarker and can be used to guide effective drug dosing of treatment for AKI and/or cancer therapies.

As discussed herein, NPM is an abundant, highly conserved nucleolar chaperone that is essential for normal cell function. In patients with acute myelogenous leukemia (AML), NPM mutations that alter NPM distribution (i.e., to the nucleus vs. cytosol) determine the susceptibility to chemo- and radiation therapy and therefore, prognosis. Post-translational phosphorylation sites have been reported to regulate NPM in human cancer cells.

NPM is essential mammalian phospho-protein that normally resides in the nucleolus as a homo-pentamer 15,16, a membrane-less region within nuclei. NPM is a molecular chaperone, that shuttles between the nucleus and cytosol to regulate ribosomal biogenesis, protein synthesis, centrosome duplication, cell cycle progression, and tumor suppression. NPM phosphorylation regulates cell death in both cancer and non-cancer cells. Accordingly, by assessing NPM's localization, de-oligomerization and its chaperone function, as well as its phosphorylation state, NPM can be used as a biomarker to predict a patient's prognosis by altering their susceptibility to chemotherapy-induced apoptosis.

Bax, a mitochondrial toxic BCL2 protein, mediates both apoptosis and necrosis and is a major cause of ischemic tissue injury. In the absence of mitochondrial localizing sequence, 80% of Bax localizes to the mitochondrial surface during apoptotic stress, suggesting that Bax requires a "chaperone service". Several labs, including our own, have shown that nucleophosmin (NPM or B23) accumulates in the cytosol of ischemic tissue, binds Bax only its conformationally active form and is a key as a Bax chaperone during ischemic AKI. In renal cells, neither NPM nor Bax kills alone. Overexpression of conformationally changed (i.e., conformationally active) Bax, characterized by exposure of the amino terminal 6A7 epitope, is non-lethal in the absence of exogenous stress. The inventors demonstrate that after stress, NPM rapidly complexes with Bax and localizes to mitochondria and causes cell death. Cell death is markedly enhanced by expressing a cytosol restricted NPM mutant. As such, the inventors demonstrate that cell death requires that "two hits" to form toxic NPM-Bax complexes: conformational Bax activation and cytosolic NPM chaperone accumulation.

The inventors herein demonstrate that limiting NPM-Bax complex formation ameliorates ischemic AKI. Since NPM's structure, functional domains, and regulatory sites are virtually identical in mice and humans, it allows the inventors to test novel NPM diagnostics and therapeutics in cells, as well as in intact murine and human kidney tissue. Our central hypothesis is that NPM-Bax mediated cell death can be effectively prevented and treated. This strategy can translate to effective clinical trials for human AKI.

Determine the Role of Stress-Induced NPM Phosphorylation Changes in Renal Cell Death and AKI.

In humans, both cell necrosis and apoptosis have been widely implicated in contributing to ischemic AKI. Bax, a toxic BCL2 member, triggers both apoptosis and necrosis by permeabilizing the outer mitochondrial membrane and altering mitochondrial dynamics. However, Bax lacks a mitochondrial localizing sequence, suggesting that Bax requires a "chaperone service" to translocate to mitochondria. Herein, the inventors demonstrate that NPM is a primary Bax chaperone that causes renal cell death that contributes to human ischemic AKI. In human cancer cells, the NPM chaperone function is regulated by post-translational phosphorylation. Herein, the inventors demonstrate that differential NPM phosphorylation during renal ischemia is essential for its chaperone function and mediates NPM-Bax toxicity that contributes to human AKI.

Moreover, the inventors demonstrate that NPM and Bax contribute to renal cell death during ischemic stress, and that NPM translocation occurs in both murine and human PTEC subjected to either ischemic stress (10 mM rotenone) or hypoxia (95% nitrogen 5% CO2 gas for 60 min) (data not shown). NPM translocation is regulated rather than a consequence of nuclear membrane injury. Overexpression of wild type NPM increases nuclear NPM content without increasing ATP depletion-induced death. In contrast, overexpression of cytosol restricted NPM mutant markedly increases both mitochondrial NPM and Bax accumulation, AIF and cytochrome c release, caspase 3 activation and death in ATP depleted PTEC in a Bax-dependent manner. Therefore it is cytosolic, rather than nuclear NPM content, that is the rate limiting in stress-induced PTEC death. In cell lines subjected to ischemic stress, cytosolic NPM translocation precedes mitochondrial Bax accumulation and in the ischemic kidney, results in persistent NPM-Bax complex formation. A recent report of multimeric NPM complexes in the nucleolar region of resting cells indicates that NPM pentamers likely predominate in the nuclear compartment in PTEC, whereas cytosolic NPM monomers accumulate only after ischemic stress. Fortunately, proximal tubule avidly concentrates intravenously administered peptides, a primary target of injury in ischemic AKI. Herein, a peptide that disrupts NPM-Bax interaction by mimicking the NPM binding domain of Bax has been reported to reduce mitochondrial injury, cell death and protects renal function and markedly improves animal survival, the murine equivalent of requiring renal replacement therapy. As demonstrated herein, this peptide (peptide #1) markedly decreases NPM-Bax complex formation in PTEC and in murine cortical homogenates harvested after in vivo ischemia, respectively. Interestingly, a 50% reduction in NPM-Bax complex formation improves renal function after transient ischemia by a similar degree 1 and motivates the development additional therapeutics directed against NPM-Bax.

To determine whether ischemia-induced posttranslational phosphorylation events regulate NPM-Bax toxicity as described in AML patients, primary murine and human PTEC, as well as ischemic murine and human kidney tissue (harvested from cadaveric kidneys rejected for transplantation) was subjected to mass spectrometry after protease digestion, a sensitive technique identifies site-specific phosphorylation and dephosphorylation events. Mass spec of NPM purified by IP revealed marked differential NPM phosphorylation in normal vs. ATP deplete primary mouse PTEC; sham and ischemic mouse kidney; as well as between paired kidneys harvested from 2 donors in which one kidney was normally perfused and other was ischemic. Trypsin plus glutamic acid digestion yielded positive identification of 269 of 292 (92%) of NPM residues and remarkably, included 100% all known serine, tyrosine and threonine residues capable of undergoing ischemia-induced phosphorylation or dephosphorylation.

In contrast to the 64 NPM phospho-changes predicted by PhosphoSite.Org, the inventors demonstrate that only 5 NPM serine/threonine phosphorylation events differed between normal and stress conditions. During ischemic stress in murine cells and both murine and human kidney, 3 residues were phosphorylated, whereas the other 2 sites were de-phosphorylated (FIG. 2D). Several of the site-specific and compartment-specific phosphorylation changes occurred within or adjacent to NPM functional domains (FIG. 4). Two of 5 phospho-events (S88 and T95) detected in ischemic PTEC have been reported to cause cell death by regulating NPM localization and de-oligomerization in AML patients that determine prognosis 21,69. However, the function of the other 3 NPM phospho-sites altered by stress (T86, T232 and S240) is unknown. Even more surprising, mass spec revealed identical phospho-events and NPM consensus sequences at the same 5 residues in primary murine and human PTEC after ischemic stress as detected in ischemic murine and human kidneys (FIG. 2D). Specifically, NPM phosphorylation in the healthy kidney was identical to healthy PTEC and to non-ischemic murine kidney (data not shown). In contrast, the ischemic human kidneys exhibited identical phospho-changes that replicated phospho-events in ATP depleted PTEC and ischemic murine kidney (with the single exception of T86; FIG. 2D). As a result of these exciting new findings in human kidneys it is highly likely that therapeutics proven in our animal model can translate to effective AKI clinical trials.

Based on this phospho-proteomic data, 32 site-specific, amino terminal, flag-tagged NPM proteins with differential phosphorylation were generated (see FIG. 4B) and placed in a lentiviral vector (Bax phospho-mimic proteins; ref Wang, Havasi et al. 2011). Both the plasmid sequence and protein expression were confirmed. Serine or threonine residues in each of the NPM phospho-mimics was rendered either nonphosphorylatable (alanine substitution) or phospho-mimetic (glutamic acid substitution) at each of the 5 NPM residues identified by mass spec to be altered by ischemia. These NPM phospho-mimics represent all of the possible combinations of constitutively non-phosphorylated and phosphorylated variants at all of the 5 phosphosites (25 total mimics, see table, FIG. 4B). The flag epitope facilitates immunohistochemistry for detecting NPM distribution, NPM oligomerization and immunoprecipitation (IP) for detecting interaction between Bax and each NPM phospho-mimic. To establish a causal link between phosphorylation and NPM-function, a flag-tagged NPM mimic that replicated the NPM phospho-state in healthy PTEC and kidney tissue (#10, "normal NPM mimic") or replicated NPM phosphorylation in post-ischemic cells and tissue (#11; "stress-NPM mimic"; FIG. 4B) was introduced into primary murine PTEC for further study. Dramatic differences in the biologic behavior of these 2 NPM phospho-mimics were detected. Specifically, the stress NPM mimic exclusively localized to the cytosol (FIG. 5A) and caused marked NPM de-oligomerization (FIG. 5B) in the absence of ischemic stress. During ATP depletion, the stress NPM mimic markedly increased NPM-Bax complex formation (FIG. 5C), dramatically increased NPM accumulation in isolated mitochondria (FIG. 5D) and significantly decreased PTEC survival after stress (FIG. 5E; n=4; P<0.05). In contrast, the normal NPM-phospho-mimic exclusively localized to nucleoli (FIG. 5A), remained in the oligomerized state (5B), minimally complexed with Bax during stress (FIG. 5C), and did not accumulate in isolated mitochondria (FIG. 5D). In contrast to the stress NPM phospho-mimic, the normal mimic actually improved PTEC survival, suggesting that it interfered with cell death caused by native NPM. Using this phospho-data generate 2 new therapeutic peptides that target either T86, S88 and T95 or T232 and S240 were generated (FIG. 4A) and tested (FIG. 7). Screening the remaining NPM mimic proteins can identify the specific function of all 5 phospho-sites. These results demonstrate that synthesis of peptides that interfere with a single phospho-site are useful therapeutics and provide a platform for testing the efficiency of NPM inhibitory peptides and peptide cocktails.

Determine the Functional Role of Stress-Induced NPM Phosphorylation Events and Renal Cell Death During Ischemic AKI.

First, the function of each of the 5 NPM serine/tyrosine phospho-sites identified in human and murine cells subjected to ischemic stress (ATP depletion or hypoxia) are assessed. To streamline screening, the effect of each of the NPM phospho-mimic protein on PTEC survival after ATP depletion or hypoxia is determined (FIG. 1). The 3 most protective and toxic NPM phospho-mimics are subjected to a panel of 5 bioassays of NPM function (described in FIG. 5A-5E). A chromatin binding nuclear release assay of the nuclear cell fraction 68 can be used to identify the phospho-change(s) that mediate NPM release from nucleolar DNA/histones, the first step in the cell death pathway. Since human primary PTEC are limited in supply and information in murine PTEC can guide in vivo experiment in mice, both primary cell lines are tested. To quantify compartment-specific changes in NPM phosphorylation caused by ischemic stress in vitro and in vivo, the phosphorylation mass at each phospho-site is measured in NPM harvested from primary human and murine PTEC subjected to ATP depletion or hypoxia using Stable Isotope Labeling by Amino acids in Cell culture (SILAC) as previously described. Mass tolerance can set to 0.1 Da for MS and MS/MS, respectively and a threshold for significant threshold can be set at P<0.05 to distinguish between correct and false peptide identifications in 3 separate samples from individual experiments. Cell compartment-specific analyses for the appropriate peptide size shift for site-specific serine/threonine phosphorylation can be analyzed. An understanding of the magnitude and cell compartment specificity of each NPM phospho-change was used to characterize the NPM-Bax cell death pathway and inform the development of specific peptides directed at one or more differentially phosphorylated NPM sites that regulate NPM-Bax toxicity.

Identify NPM Interacting Proteins as Therapeutic Targets in AKI.

To identify NPM binding partners (including Bax, FIGS. 9A-9B) and optimize the treatment and prevention of AKI, mass spectrometry for protein-protein interaction can be performed from resting human and murine and PTEC lysates using an NPM antibody (Abcam; Cambridge, Mass.) before and after ATP depletion or hypoxia. Specifically, proteins that interact with the 3 most toxic NPM mimic proteins and the 3 most protective NPM mimics were subjected to mass spec performed under conditions that preserve protein-protein interactions, an approach successfully used to detect protein interactions in intact cells. This approach identifies both protective and toxic NPM interacting proteins. Since NPM-Bax interaction occurs during ischemic stress, analysis of the NPM immunoprecipitates is performed to ensure detection of Bax (as a positive control) before submitting samples for mass spectrometry to identify other NPM binding partners. The stringency of the conditions used to IP NPM from PTEC can be adjusted until Bax is detected in NPM immunoprecipitates to increase the yield of other NPM binding partners that represent new therapeutic targets for interfering with the NPM cell death pathway during ischemic stress. Recently, Hsp90 and Hsp70, stress-induced proteins that regulate cell survival, have been physically linked to NPM, and are likely to regulate NPM-Bax toxicity. In addition, both BAG-1 (an Hsp70 binding protein) and CRM-176 have been reported to interact with, and regulate NPM. Therapeutics directed at NPM interacting proteins can also be selected as NPM inhibiting agents, as described herein that can ameliorate NPM-Bax complex formation and toxicity in a manner similar to the disclosed therapeutic NPM inhibitor peptides (FIG. 7).

Herein, the inventors have demonstrated the following (1) a direct link between site-specific NPM phosphorylation events of NPM polypeptide and its NPM contribution to cell death; (2) demonstrated location of quantitative phospho-site amino acids that can be blocked or interfered with for the development of NPM inhibitor peptide therapeutics; and (3) identified NPM binding partners during ischemia to identify additional therapeutic targets for testing in vitro and in vivo. Given the clear results provided by the normal and stress mimic NPM phospho-mimics in each of the 5 bioassays, the inventors tested 30 remaining NPM phospho-mimics (FIG. 4B) in murine and human PTEC to identify the specific sites(s) that regulate each NPM function (data not shown). Although a single phospho-event regulates both NPM de-oligomerization and nuclear NPM translocation in AML patients, it is likely that a combination of stress-induced phosphorylation events regulate some NPM functions, and therefore the inventos assessed all potential phosphocombinations (FIG. 4B). The inventors also envion blocking the interaction of NPM interacting proteins to inhibit NPM-Bax formation, as NPM-Bax undergoes mitochondrial translocation and NPM also lacks a mitochondrial localizing sequence. Finally, identification of NPM interacting proteins that bind to protective NPM mimics protein can be used to cytoprotection. For example, if interaction between a toxic NPM mimic and a specific protein is detected by mass spec, then one can use an established algorithm to identify its NPM interaction domain and a website is available (http://cmbi.bjmu.edu.cn/huphospho). Once identified, a NPM inhibiting or blocking peptide can be synthesized and tested.

While ischemic stress in vitro does not replicate ischemia in vivo, herein, the inventors now demonstrate show that virtually identical phospho-events occur after ischemic stress in mice and human PTEC as in ischemic murine and human kidneys (FIG. 2D), cells are appropriate for testing the efficacy of our therapeutic agents and to inform animal studies. Of the 65 potential post-translational modifications detectable by mass spectrometry, the inventors discovered that serine/threonine phosphorylation regulates NPM toxicity during cell stress. As an inexpensive and rapid alternative to mass spec, commercially available phospho-antibodies can be used to detect site-specific NPM phosphorylation. Although an anti-T95 phospho-antibody is presently available (AbCam, Cambridge, Mass.), one can of ordinary skill in the art can readily generate new NPM phospho-specific antibodies directed against T86, S88, T232 and S240 using a commercial vendor (for example, see: "thermofisher.com/us/en/home/lifescience/antibodies/custom-antibodies/custom-antibody-production/custom-monospecific-antibody-production"). Such phospho-specific Abs can be used to distinguish toxic from non-toxic forms of NPM in the urine and other biological samples from animals and patients, e.g., human subjects after renal ischemia.

To What Extent does Antagonizing NPM-Bax Prevent Renal Epithelial Cell Death and Tissue Injury?

Figures 10, 11:
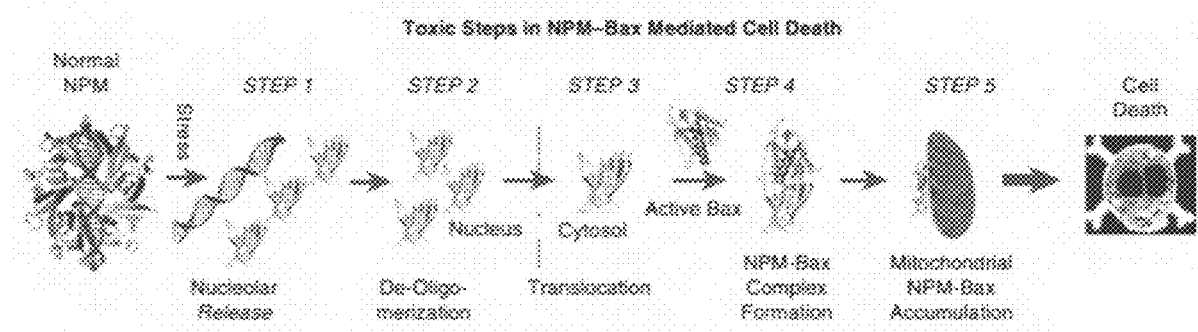
FIG. 10 shows five phosphorylation changes mediate NPM toxicity during ischemic stress. Based on the results of the NPM bioassays (FIG. 5), phosphorylation events at S88 and T9540,41 regulate steps 1-3 in the nucleophosmin-Bax cell death pathway. T95 phosphorylation also regulates cell death in response to chemotherapy and radiation therapy in acute myelogenous leukemia.40,41 Release from nucleolar binding sites is assumed to occur before NPM deoligomerization or cytosolic translocation.45,75 The function of NPM-T86, T234, and S242 phosphorylation changes during ischemic cell death also occurs.
FIG. 11 shows exemplary peptides or pharmaceuticals (e.g., small molecules) that can be used on combination with a NPM inhibitor agent as defined herein. These agents include geronylgeronylacetone (GGA), a potent Hsp70 inducer86, avrainvillamide, and NSC34888437.

The inventors have determined that ischemic stress converts NPM from a cellular friend to a cytotoxic foe that collaborates in lethal "Bax Attack" (FIG. 10). In human disease, it is unusual for single intervention to achieve therapeutic success. However, strong preliminary data show that interventions directed against NPM-Bax significantly decrease injury in primary human PTEC and participate in ischemic injury in human kidneys. However, a combination of agents that antagonize NPM-Bax will be more effective than if each is used alone. After identifying the NPM post-translational phosphorylation events responsible for NPM-Bax toxicity and NPM interacting proteins, site-specific therapeutic peptides (e.g., Peptides #1, #2 and #3 disclosed herein) can be combined with pharmacologic agents, can be used to disrupt NPM-Bax toxicity and to optimize human and murine PTEC survival as well as the viability of human and murine kidney tissue delivered either before or after ischemic stress. Exemplary compounds or agents to be combined are shown in FIG. 11. The inventors selected the reagents to be combined based on performing an in vivo study with Bax blocking peptide and GGA, reagents with distinct mechanisms of action (data not shown). A Peptide #1 and GAA combination was significantly more reno-protective than either agent alone in mice subjected to renal ischemia (data not shown).

NPM is a relevant therapeutic target in human AKI. Primary human proximal tubule epithelial cells (PTEC) derived from cadaveric kidneys were subjected to ischemic stress (transient ATP depletion) in the presence of specific NPM siRNA or non-sense siRNA. This maneuver reduced steady state NPM content by 50% in PTEC lysates and significantly increased PTEC survival after ischemic stress (FIG. 6; $P<0.05$; n=6). Thus, manipulating NPM is an effective maneuver. Using mass spec data, the inventors generated 2 new, water soluble peptides that penetrate renal cell membranes (SEQ ID NO: 8-10) and significantly improve PTEC survival after ischemic stress (synthesized by Biomatik, Cambridge, Ontario). Small peptides of 30 amino acids or less are sufficiently specific to minimize off target effects and also reduce the risk of eliciting an antibody response that causes tachyphylaxis. Peptides were commercially synthesized and fused to a nuclear localizing sequence (this NLS has no functional relationship to the "NPM NLS" that regulates NPM translocation). The NLS-CPP markedly increases renal accumulation of small peptides 8 as well as in the proximal tubule. Compared to control (a random amino acid sequence fused to the NLS and CPP), the Bax blocking peptide (#1) significantly improved cell survival by 25% ($P<0.05$; n=5). To determine its effect on NPM-Bax complex formation, active Bax was immunoprecipitated from PTEC rendered ischemic with an antibody directed against the 6A7 epitope. The precipitates were subjected to immunoblot analysis using an anti-NPM antibody. Compared to control (a size matched random peptide), the Bax blocking peptide (Peptide #1) decreased NPM-Bax complex formation by about 50% in ischemic primary murine PTEC as well as in renal cortical homogenate harvested from a murine kidney after ischemia caused by pedicle clamping (FIG. 9A-9B). NPM and Bax accumulation was measured in mitochondria isolated from human PTEC after ischemic stress. The Bax blocking peptide decreased mitochondrial Bax accumulation to a greater extent than it reduced NPM accumulation, especially after ischemic stress $P<0.05$, n=4; upper panel). This data strongly demonstrates that NPM-Bax complex formation as a prerequisite for Bax-mediated outer membrane injury that causes PTEC death1. Taken together these results show that NPM-Bax complex formation accompanies ischemic stress in vitro and in vivo and that our Bax blocking peptide partially decreases complex formation and reduces mitochondrial Bax accumulation. Thus, the inventors have demonstrated that increasing the peptide dose above 2 mg/animal (7 µM) or administering a second dose within 24 hr did not provide additional protection in ischemic PTEC or mice. This is likely due to the prolonged half-life (about 80 hr) of the peptide in vitro and in vivo due to the presence of an AC modification slows degradation.

To generate reagents for testing as a therapeutic cocktail, new peptides that either replicate all 3 amino-terminal NPM phosphorylation sites (T86, S88 and T95; FIG. 4A) or both carboxy-terminal phosphorylation sites (T232 and S240) that are altered by renal ischemia in vivo (FIG. 2D) were also tested in vitro. Both peptides significantly improved human PTEC survival after ischemic stress ($P<0.05$, n=4). Thus, renal-targeted peptides that potentially block multiple NPM phospho-sites during renal ischemia are an effective approach for ameliorating NPM-Bax toxicity and improving PTEC survival. This demonstrates additional NPM phospho-proteomics and additional peptides can be developed that interfere with NPM-Bax toxicity and ameliorate ischemic AKI in humans.

The inventors have also tested pharmacologic agents that disrupt NPM-Bax at specific steps in the cell death pathway (outlined in FIG. 11). These agents include geronylgeronylacetone (GGA), a potent Hsp70 inducer86, avrainvillamide, and NSC34888437. Importantly, exposure to the IC50 dose of these agents does not alter PTEC morphology or cause significant toxicity after 48-72 hr (data not shown). The inventors recently reported that GGA induces Hsp70 in murine PTEC and in the intact murine kidney. Hsp70 markedly reduces NPM-Bax complex formation during ischemic stress by 2 distinct mechanisms: a nucleolar-restricted Hsp70 mutant limits NPM translocation into the cytosol, whereas a cytosol restricted Hsp70 mutant sequesters cytosolic (data not shown).

Importantly, GGA-mediated cytoprotection requires Hsp70, since protection is not observed in PTEC harvested from Hsp70 knockout mice, confirming that Hsp70 itself protects against NPM-Bax toxicity. The role of Hsp70 (and Bag-1, an Hsp70 regulatory protein) as a potential NPM interacting protein is assessed by the inventors and the inventors discovered that GGA augments reno-protection afforded by the Bax blocking. Historically, therapy derived from cell culture or animal models has failed to translate to human AKI. To address this challenge, the inventors provide data in human cells and tissue. The inventors compared the degree of NPM translocation from the nuclear to the cytosolic cell fractions of primary murine and human PTEC subjected to ischemic stress (ATP depletion or hypoxia, an alternative ischemia model). In both cases, ischemic stress markedly increased cytosolic NPM content in murine and human primary PTEC. A marked increase in cytosolic NPM was also detected in renal cortical homogenates obtained from ischemic cadaveric kidneys rejected for transplantation form two donors. One kidney form each donor has perfusion failure, was grossly ischemic and exhibited severe proximal tubular injury. The other kidney in each pair was well perfused without ischemic injury. Cytosolic NPM accumulation was markedly increased in cortical homogenates harvested from the ischemic human kidneys vs. control (FIG. 3B-3C). Therefore, the inventors demonstrate that NPM leakage, the first step in the NPM-Bax cell death pathway occurs after ischemic stress in vitro and in the intact human kidney.

Combining Peptides and Pharmaceuticals to Maximally Reduce NPM-Bax Toxicity In Vitro.

To streamline the experiments, single therapeutic peptides and pharmaceuticals with distinct mechanisms of action were first be screened for their pro-survival effect in murine PTEC subjected to ischemic stress (ATP depletion or hypoxia) using a high throughput MMT assay in 96 well plates. Based on these studies, a cocktail of the most effective peptides with distinct mechanisms of action were tested (e.g., the Bax blocking peptide (peptide #1) that interferes with NPM-Bax complex formation are combined with peptides (peptides #2 and #3) that interfere with toxic NPM phospho-events. The most effective peptide cocktail are be combined with pharmaceuticals that either reduce NPM translocation (avaranillamide and GGA), de-oligomerization (NSC34884 and an specific RNA aptamer described by others) (see FIG. 11), and NPM-Bax complex formation (Bax and NPM peptides), and mitochondrial NPM-Bax translocation (peptide(s)) to improve PTEC survival after ischemic stress is assessed. The most effective therapeutic combinations are tested for their pro-survival effect in ischemic primary human PTEC. The effect of these therapeutic maneuvers on NPM-Bax toxicity is assessed using bioassays of NPM function and correlated with renal cell death caused by apoptosis and necrosis. Apoptosis is detected using assays of outer mitochondrial membrane injury (apoptosis inducing factor (AIF) and cytochrome c leakage), caspase 3 activity, and morphologic evidence of apoptosis in cells stained with Hoechst, the "gold standard" for detecting condensed chromatin and apoptotic bodies. Necrosis can also be quantified using propidium dye uptake and LDH release (markers of cell membrane injury). To more rapidly assess the type of cell death after ischemic stress, the inventors adopted a new screening technique, where the assay uses the Celigotm image cytometer to rapidly distinguish apoptotic from necrotic cells stained with propidium iodide, Hoechst dye #33342 and annexin V. The inventors demonstrate that Celigo measures of cell death (apoptosis+necrosis) replicate the MTT assay (data not shown). To assess their efficacy for treating ischemic stress, the exposure to the most effective combination(s) for preventing ischemic PTEC injury in vitro, is progressively delayed after ischemic stress. This approach inform in vivo treatment of AKI, and provides insight into the therapeutic window for AKI treatment and reduce the number of animal experiments. Effective therapeutic Interventions derived from cells culture experiments is selectively tested in fresh, 100 micron thick human and murine kidneys slices subjected to ischemic stress. This experimental model has been extensively used to simulate ischemia in vivo and has the benefit of including multiple renal cell types and intact kidney architecture 95,96. To be suitable for testing, tissue slices will require: minimal or no evidence of acute injury (minimal trypan blue staining and absent or minimal cytosolic NPM accumulation). Tissue slices will be subjected to hypoxia or exposed to metabolic inhibitors that reduce cell energy content. Measures of cell death (trypan blue, Hoechst, and annexin V staining as well as LDH release) and histologic injury score will be correlated with the effect of therapeutics on each of the NPM functional bioassays. The impact of the most effective therapeutics on NPM phosphorylation will be assessed by mass spec. To identify their target of protection in murine and human kidney tissue, fluorescent-labeled peptides (synthesized by Biomatik) will be used to assess their intra-renal distribution in 10 micron tissue sections.

Generation of Additional Peptide Therapeutics for Antagonizing NPM-Bax.

Since the Bax blocking peptide (peptide #1) reduces but does not eliminate NPM-Bax interaction, the inventors generated a new peptide that competitively inhibits the NPM binding site for Bax (described in Example 1). To selectively inhibit each regulatory NPM phospho-site, fluorescent labeled peptides that replicate their consensus sequences and the regions flanking it are designed and tested as reported for other peptides. The phospho-site (initially 10-20 amino acids in length flanking the 5-10 amino acids adjacent to each of the 5 identified phospho-sites) are produced. The competitive NPM inhibitor peptide of interest can optionally be fused to the NLS sequence and/or a cell penetrating peptide ("CPP") that markedly enhances renal uptake of our competitive Bax peptide mimotope, creating a therapeutic peptide of 20-30 residues in length. Since the ischemic phospho-NPM mimic strongly interacts with Bax, it can be used to identify the specific phospho-site that regulates NPM-Bax interaction. A peptide directed against NPM will also disrupt NPM-Bax interaction, further decreasing NPM-Bax interaction and cell toxicity.

Identification of the Mechanism of Action of Peptides and Pharmaceuticals Directed Against NPM-Bax.

The mechanism of action for each of our interventions on NPM-Bax can be assessed by complimentary approaches including mass spec to identify their impact on post-ischemic NPM phosphorylation events, NPM phosphospecific antibodies, and NPM functional bioassays. A mammalian 2-hybrid system combined with a Luciferase Reporter Assay System (CheckMate™ and Dual-Luciferase Reporter Assay System; Promega, Madison, Wis.) was used to assess interaction between the most toxic and protective NPM mimic with Bax mammalian cells and kidney tissue. This assay was used in cells and kidney slices to demonstrate the degree to which peptides and pharmaceuticals disrupt the NPM-Bax complex and characterize their mechanism of action. For example, the therapeutic peptides #2 and #3 could competitively inhibit interaction between NPM and the kinases or phosphatases that regulate NPM phosphorylation events during ischemia. Alternatively, these peptides could act as decoys for the regulatory kinase or phosphatase, without requiring them to interact with NPM. To monitor stress-induced NPM translocation in live cells and the effect of interventions to inhibit it, PTEC are infected with lentivirus that contains wild type and mimic NPM fused to DS red (Addgene, Cambridge, Mass.) at the carboxyNPM terminus. Flag or DS red tagged NPM mimics will replicate baseline vs. stress-induced changes in phosphorylation at T86, S88, T95, T232, and/or S240 singly and in all possible combinations (FIG. 4A-4B).

The inventors have developed peptides that block NPM-protein interactions regulated by NPM phosphorylation events. One can combine reagents that act on distinct steps in the NPM-Bax pathway (FIG. 11) to optimally antagonize NPM-Bax. Specifically, PTEC survival, tissue viability and histologic score can be improved by simultaneously reducing NPM translocation, de-oligomerization, NPMBax complex formation, and mitochondrial accumulation of the NPM-Bax complex. One can first identify the most effective reagent (peptide or pharmaceutical) that antagonizes each toxic step and then to combine them. NPM bioassays are correlated with PTEC survival in vitro and histologic injury in tissue slices in the most effective combinations. The mammalian 2-hybrid system can quantify the protective effect of combined peptide and pharmaceuticals for preventing and treating AKI. Although existing evidence is stronger that NPM-Bax mediates apoptosis, recent evidence shows that necrosis converges at the outer mitochondrial membrane, involve Bax, and that the latter form of cell death is regulated. Therefore, antagonism of the NPM-Bax cell death pathway will decrease both apoptosis and necrosis.

Cell death pathways other than apoptosis and necrosis exist. However, minimal evidence suggests that these pathways contribute to ischemic AKI in humans. In addition, these pathways lack a distinctive morphology (unlike apoptosis or necrosis) and at present, are either biochemically defined (e.g., by RIP3 kinase activation) or are implicated by their response to inhibitors (e.g., necrostatin). However, phosphorylation regulates some of these pathways and would be amenable to proteomic analysis by mass spec to inform the development of interfering peptides for this alternative cell death pathway. As discussed herein, proteomics is used to reveal the actual NPM binding site for Bax, to develop a peptide antagonist. In addition to use of mass spectrometry to reveal the phospho-site that regulates Bax binding, serial NPM truncation (NPM is a 292 aa protein) can be performed to evaluate the region on NPM that binds to Bax.

Example 6

Evaluate NPM Phosphorylation in the Diagnosis, Treatment and Prevention of AKI In Vivo.

Preliminary data show that NPM-Bax is a highly promising target in human AKI. Data gathered in Examples 1 and 2 can be used to improve therapeutic efficacy beyond that afforded by the Bax blocking peptide (Peptide #1) alone, extend the time window for treating AKI (currently 3 hr) and assess the impact of therapeutics on apoptosis and necrosis, forms of death detected in human AKI. Unfortunately, renal function (BUN/Cr) are imperfect for rapidly or accurately diagnosing AKI and GFR loss fails to detect nearly 45% of human AKI. Urinary biomarkers have improved AKI diagnostics but have not been clinically useful in the absence of effective human therapy. To address this concern, the Kidney Research National Dialogue sponsored by the NIDDK suggested new biomarkers and tissue assays that can be translated to human AKI and are linked to its pathogenesis would be useful.

In sum, an ideal AKI biomarker described herein: (1) rapidly and accurately detects AKI; before a change inGFR or urine output; (2) reflects AKI severity (need for renal replacement therapy and the likelihood of recovery); (3) triggers therapy; (4) guides optimal dosing of reno-protective agents. To address these challenges, the inventors have combined two newly developed in urine and in human kidneys biopsy tissue for detecting NPM. Combined with assays of differential NPM phosphorylation this novel biomarker is useful for detecting ischemic as well as nephrotoxic AKI, common diseases (aminoglycosides, vancomycin, cisplatin and radiocontrast agents) in which Bax (and therefore NPM) have been reported to play a pathogenic role.

The renal-targeted Bax blocking peptide (peptide #1) reduces AKI severity by 40-50% in mice when administered before the insult. To determine its efficacy for treating ischemic AKI, the inventors delayed IV peptide administration for 0-6 hr after releasing the pedicle clamp. Compared to control (random peptide), the Bax blocking peptide, significantly improved BUN by 15-35% on days 1-6 if given within 3 hr after 22 min bilateral renal ischemia. Although 30% of control mice died of severe AKI, 98% of peptide-treated animals survived. As intended, the Bax blocking peptide decreased NPM-Bax interaction in renal cortical homogenates by about 50%, an effect similar to the degree of reno-protection. This data demonstrates that more effective therapy directed at the NPM-Bax pathway is both rational and feasible.

To test the hypothesis that therapeutics with distinct mechanisms of action on NPM-Bax improve AKI outcome, the inventors combined a single dose of our Bax blocking peptide with GGA, a non-toxic agent widely used in Asia for dyspepsia that also induces Hsp70 and is reno-protective. This is an ideal drug combination since the Bax peptide reduces NPM-Bax complex formation (data not shown) and GGA reduces cytosolic NPM accumulation during ischemic stress exclusively by inducing Hsp70 (data not shown). After 28 min of bilateral pedicle clamping, a severe renal insult, Bax peptide plus GGA was significantly more protective than either agent alone on renal function measured on days 1-7 (data not shown). Remarkably, control mice had a mean BUN level of 140 mg/dl and all animals died within 48 hr after ischemia. In contrast, mice treated with Bax peptide, GGA or the combination of these agents had a mean peak BUN of only 100 m/dl and all survived! Thus, therapy that antagonizes NPM-Bax at multiple steps is more effective in protecting renal function than a single agent and improves survival, the rodent endpoint equivalent to a patient requiring dialysis.

To improve AKI diagnostics and assessment of its severity, the inventors herein have developed a urine assay to detect NPM released by ischemic renal cells. In brief, urine supernatant was assayed for NPM after intact cells were removed by differential centrifugation (1,500 RPM×5 min). In normal mice at baseline as well as sham operated mice (n=3), urinary NPM is virtually undetectable. In contrast, urinary NPM is abundant after 22 min bilateral pedicle clamping detected by a specific NPM antibody (Sigma-Aldrich, St. Louis, Mo.) using a semi-quantitative dot blot assay (FIG. 3A; n=9). In fact, NPM appeared within 12 hr and persisted for at least 24 hr after ischemia. NPM was also detected in the tubular lumen of an ischemic human kidney (FIG. 3B-3C). Remarkably, 4 of 9 ischemic mice with the highest urinary NPM content died within 48 hr. These data show for the first time that urinary NPM may be: (1) an effective biomarker for proximal tubule cell death; (2) predict the severity of organ injury and (3) be a suitable assay for optimizing the dose of our therapeutics in murine and human AKI. Quantitative urinary dot blot testing with phospho-specific NPM antibodies that exploit differential phosphorylation (as detected in normal and ischemic murine and human kidneys; (FIG. 3A) may be an even more accurate marker of AKI onset, severity and recovery.

To assess the feasibility of using NPM as a diagnostic marker in human AKI, NPM immunohistochemistry (IHC) and Hoechst staining was performed on fresh frozen 10 micron thick human kidney tissue sections obtained by routine biopsy. Blinded specimens from 3 patients were examined with normal appearing tubules or mild acute tubular injury or severe acute tubular injury. In this study, NPM was exclusively localized to the nuclei of healthy proximal tubule cells (FIG. 3C). In contrast, NPM was diffusely distributed in cytosol or lumen of damaged tubular cells; the nuclear region was devoid of NPM (FIG. 3C). Interestingly, the degree of cytosolic NPM staining positively correlated with tubular injury severity (data not shown), whereas NPM in medullary tubules remained nuclear. Remarkable, NPM redistribution occurred before Hoechst staining revealed evidence of either apoptosis or necrosis. Thus NPM translocation may be an early diagnostic marker that is pathophysiologically linked to renal death and organ failure.

To What Extent do Maneuvers that Antagonize NPM and Bax Ameliorate Ischemic AKI?

The prevention and treatment of in vivo renal ischemia can be based on in vitro studies of the single most effective peptide and pharmaceuticals that individually decrease each step in the NPM-Bax cell death pathway (FIG. 10) as assessed by our NPM bioassays. The reagent dose and timing is guided by in vitro experimental results, published IC50 data for GGA, the RNA aptamer dose successfully used in mice and the inventors prior experience with the Bax peptide in murine AKI. Renoprotection afforded by single or combined therapeutic is assessed by serial serum BUN/Cr measured for 7 days post-ischemia, a time frame adequate to encompass the peak severity of AKI and death or recovery. For maneuvers that afford significant reno-protection, studies were repeated and mice sacrificed at 24 hr post-ischemia to perform a comprehensive, blinded histologic injury score (including an estimate of leukocyte infiltration) as previously described. The most effective maneuvers that prevent ischemic AKI are further tested as potential AKI treatment. To establish the therapeutic window for treating AKI, combined therapy is progressively delayed for 1-12 hours post ischemia or until significant reno-protection is no longer observed. To assess the degree to which of the NPM inhibitor agents/therapeutics interfere with steps in the NPM-Bax cell death pathway, NPM bioassays described (FIG. 5A-5E plus a DNA/histone binding release assay are repeated in renal cortical homogenates (as described above). Renal uptake and the intra-renal distribution of peptides that disrupt NPM-Bax interaction is assessed using fluorescent-tagged Bax and NPM peptides (synthesized by Biomatik). Apoptosis and necrosis were quantified using multiple methods. First, blinded fresh kidney tissue sections are stained with Hoechst 33342 and PI, a vital dye, followed by fixation and TUNEL staining as described in the ischemic kidney in vivo 122.

Second, pan-caspase activity, a direct measure of active apoptosis in fixed tissue is measured with a kit (CAS-MAP by Vergent Bioscience, Minneapolis, Minn.). Since necrosis and apoptosis likely vary with the ischemia severity, renal pedicles are clamped for 25, 30 or 35 min to assess their relative contributions to progressive organ failure and mortality. After injection of paraformaldehyde in situ, the distribution of the fluorescent label is assessed by routine histochemistry in 10 micron thick frozen kidney tissue sections as described by us for a2-microglobulin. These studies identify interventions that disrupt NPM toxicity, inhibit apoptosis and necrosis, characterize their mechanism of action, identify the intra-renal structures protected by NPM and Bax peptides, and optimize therapeutics for treating and preventing ischemic AKI in a model that replicates the NPM-Bax toxicity in human AKI.

Using NPM and Differential NPM Phosphorylation in a Urine and Tissue as a Diagnostic and Prognostic Assay for AKI.

Urine collected from control, sham-operated and post-ischemic mice are accessed by simple bladder compression and analyzed for NPM content using quantitative dot blot analysis, a technique that measures total urinary NPM independent of urine volume. Total urine NPM can be correlated with kidney function (BUN/Cr), histologic injury score and animal survival. The time window for detecting urinary NPM is tested between 0-48 hr after ischemia and is compared with established urinary AKI biomarkers including KIM-1, NAG and NGAL125-128 that in combination, predict AKI with greater accuracy than GFR markers. In addition to total urinary NPM content, site-specific phosphorylation NPM phosphorylation is measured in ischemic human and murine kidneys and murine urine by quantitative dot blot using site-specific phospho-antibodies. This urinary NPM phospho-data is correlated with kidney tissue NPM bioassays, kidney function, histology, and animal survival. To determine the extent to which these new NPM assay predicts renal recovery, total and phospho-NPM is probed with site-specific NPM-phospho-antibodies in the murine urine after the administration of effective therapeutics to detect each toxic phosphorylation event (FIG. 2D). This study demonstrates that NPM and phospho-NPM with ischemic AKI severity and facilitate the use of non-invasive (urine based) assays to substitute for invasive (tissue based) testing in ischemic AKI.

To identify causes of human AKI amenable to NPM-Bax therapy, NPM redistribution into the cytosol, the first step in NPM cell death pathway, is assessed by IHC in human kidney biopsy specimens obtained from patients with ischemic or nephrotoxic AKI of diverse etiologies and compared to controls without tubular injury. Blinded tissue samples are subjected to routine IHC with semi-quantitative histologic scoring of tubular injury. Tissue samples are probed with an NPM antibody to assess NPM localization and with site-specific NPM phospho-antibodies to assess the intra-renal distribution of NPM with toxic phosphorylation events that should replicate the toxic vs. normal NPM mimic; FIG. 5A). At least 10 random fields in each specimen with be analyzed with an automated scanning microscope (BU core imaging facility) using averaged threshold measure (ATM) to objectively score tissue staining. NPM redistribution in the proximal, distal and collecting ducts are compared in renal cortex, juxtamedullary region and the medulla of ischemic mice as well as in blood vessels and endothelium to assess the effect of ischemia on renal NPM.

Given that the inventors have demonstrated that combined therapy is superior to single agent, one easily can use a strategy of a combination of agents, e.g., as shown in FIG. 11 with one or more of the NPM inhibitor agents (e.g., including but not limited to inhibitor peptides comprising SEQ ID NO: 1-3 or peptides having 85% sequence identity thereto) to increase reno-protection for preventing ischemic AKI and to extend the time window for its treatment as described for ischemic stroke or acute myocardial ischemia. Reducing NPM-Bax toxicity decreases both apoptosis and necrosis in vivo and that in combination, more accurately predicts GFR than necrosis alone. Also, urinary NPM increases the sensitivity of existing urinary AKI biomarkers. This assay detects a fall in total and phospho-urinary NPM that is likely to reflect effect therapy directed against NPM-Bax in mice and humans. Finally, NPM translocation is detected in forms of nephrotoxic AKI in which Bax has been implicated to cause tubular injury before GFR or urine output deteriorate, triggering early, effective intervention with therapeutics to ameliorate NPM-Bax toxicity. Since post-translational NPM modification uniformly detects ischemic renal injury in PTEC and kidney tissue (FIG. 2D), use of phospho-NPM is a more sensitive test for NPM-toxicity than total NPM. Since urinary NPM persists in ischemic mice for at least 24 hr (FIG. 3A), quantitative urinary total and phospho-NPM allows one to establish a threshold values to accurately predict the severity and reversibility of ischemic AKI in mice (and ultimately in humans). Since NPM distribution strikingly differs in normal vs. damaged proximal tubules (and medullary tubules), NPM also identifies the spectrum of AKI patients in whom NPM-Bax therapeutics are likely to be effective. The inventors described urine and tissue assays that provide mechanistic insight into AKI pathogenesis, and allow the subject to be administered the NPM peptide/pharmaceutical therapy as described herein and also may be useful to predict renal recovery.

Although BUN/Cr do not accurately reflect fluctuating GFR113, others have used these parameters to approximate peak GFR loss for timing histologic and biochemical analyses. One will be able to detect at least some site-specific NPM phospho-changes using phospho-antibodies. Alternatively, one of ordinary skill in the art can perform mass spec of urinary NPM as described herein (see FIG. 2A-C). Ameliorating NPM-Bax toxicity will reduce inflammation detected in kidney tissue. One can also perform further analysis of resident dendritic cell activation, infiltrating neutrophils and macrophages, CD4+ T and B cells as well as killer T cells implicated in AKI using a flow cytometry assay to identify inflammatory cells in minced fresh kidney tissue. Also, If NPM translocation is detected in kidney biopsies of patients with nephrotoxic AKI, one can assess other measures of NPM-Bax toxicity including Bax activation using a 6A7 specific Ab, and NPM-Bax complex formation (FIG. 10) in stored kidney biopsy tissue. Finally, since cell culture and rodent models of nephrotoxic AKI are readily available, one can also directly assess our NPM-Bax therapeutics for preventing and treating in nephrotoxic AKI in which NPM translocation occurs.

REFERENCES

All references cited herein and throughout the specification and Examples are incorporated herein in their entirety by reference.

1. Basile D P, Anderson M D, Sutton T A: Pathophysiology of acute kidney injury. Compr Physiol 2: 1303-1353, 2012
2. Bonventre J V, Basile D, Liu K D, McKay D, Molitoris B A, Nath K A, et al.: Kidney Research National Dialogue (KRND): AKI: A path forward. Clin J Am Soc Nephrol 8: 1606-1608, 2013
3. Bonventre J V, Yang L: Cellular pathophysiology of ischemic acute kidney injury. J Clin Invest 121: 4210-4221, 2011
4. Chertow G M, Burdick E, Honour M, Bonventre J V, Bates D W: Acute kidney injury, mortality, length of stay, and costs in hospitalized patients. J Am Soc Nephrol 16: 3365-3370, 2005
5. Wang H E, Muntner P, Chertow G M, Warnock D G: Acute kidney injury and mortality in hospitalized patients. Am J Nephrol 35: 349-355, 2012
6. van Beek S C, Legemate D A, Vahl A, Bouman C S, Vogt L, Wisselink W, et al.: Acute kidney injury defined according to the 'Risk,' 'Injury, 'Failure,' 'Loss,' and 'End-stage' (RIFLE) criteria after repair for a ruptured abdominal aortic aneurysm. J Vasc Surg 60: 1159-1167.el, 2014
7. Andreoli S P: Acute renal failure in the newborn. Semin Perinatol 28: 112-123, 2004
8. Mammen C, Al Abbas A, Skippen P, Nadel H, Levine D, Collet J P, et al.: Long-term risk of CKD in children surviving episodes of acute kidney injury in the intensive care unit: A prospective cohort study. Am J Kidney Dis 59: 523-530, 2012
9. Askenazi D J, Feig D I, Graham N M, Hui-Stickle S, Goldstein S L: 3-5 Year longitudinal follow-up of pediatric patients after acute renal failure. Kidney Int 69: 184-189, 2006
10. Sutherland S M, Ji J, Sheikhi F H, Widen E, Tian L, Alexander S R, et al.: AKI in hospitalized children: Epidemiology and clinical associations in a national cohort. Clin J Am Soc Nephrol 8: 1661-1669, 2013
11. Yang Y, Song M, Liu Y, Liu H, Sun L, Peng Y, et al.: Renoprotective approaches and strategies in acute kidney injury. Pharmacol Ther 163: 58-73, 2016
12. Linkermann A, Skouta R, Himmerkus N, Mulay S R, Dewitz C, De Zen F, et al.: Synchronized renal tubular cell death involves ferroptosis. Proc Natl Acad Sci USA 111: 16836-16841, 2014
13. Wang Z, Gall J M, Bonegio R, Havasi A, Illanes K, Schwartz J H, et al.: Nucleophosmin, a critical Bax cofactor in ischemia-induced cell death. Mol Cell Biol 33: 1916-1924, 2013
14. Parikh S M, Yang Y, He L, Tang C, Zhan M, Dong Z: Mitochondrial function and disturbances in the septic kidney. Semin Nephrol 35: 108-119, 2015
15. Yamamoto K, Tomita N, Yoshimura S, Nakagami H, Taniyama Y, Yamasaki K, et al.: Hypoxia-induced renal epithelial cell death through caspase-dependent pathway: Role of Bcl-2, Bcl-xL and Bax in tubular injury. Int J Mol Med 14: 633-640, 2004
16. Grisendi S, Bernardi R, Rossi M, Cheng K, Khandker L, Manova K, et al.: Role of nucleophosmin in embryonic development and tumorigenesis. Nature 437: 147-153, 2005
17. Frehlick U, Eirin-Lopez J M, Ausio J: New insights into the nucleophosmin/nucleoplasmin family of nuclear chaperones. BioEssays 29: 49-59, 2007
18. Amin M A, Matsunaga S, Uchiyama S, Fukui K: Depletion of nucleophosmin leads to distortion of nucleolar and nuclear structures in HeLa cells. Biochem J 415: 345-351, 2008
19. Box J K, Paquet N, Adams M N, Boucher D, Bolderson E, O'Byrne K J, et al.: Nucleophosmin: From structure and function to disease development. BMC Mol Biol 17: 19, 2016
20. Banerjee P R, Mitrea D M, Kriwacki R W, Deniz A A: Asymmetric modulation of protein order-disorder transitions by phosphorylation and partner binding Angew Chem Int Ed Engl 55: 1675-1679, 2016
21. Koike A, Nishikawa H, Wu W, Okada Y, Venkitaraman A R, Ohta T: Recruitment of phosphorylated NPM1 to sites of DNA damage through RNF8-dependent ubiquitin conjugates. Cancer Res 70: 6746-6756, 2010

22. Qi W, Shakalya K, Stejskal A, Goldman A, Beeck S, Cooke L, et al.: NSC348884, a nucleophosmin inhibitor disrupts oligomer formation and induces apoptosis in human cancer cells. Oncogene 27: 4210-4220, 2008
23. Balusu R, Fiskus W, Rao R, Chong D G, Nalluri S, Mudunuru U, et al.: Targeting levels or oligomerization of nucleophosmin 1 induces differentiation and loss of survival of human AML cells with mutant NPM1. Blood 118: 3096-3106, 2011
24. Lieberthal W, Menza S A, Levine J S: Graded ATP depletion can cause necrosis or apoptosis of cultured mouse proximal tubular cells. Am J Physiol 274: F315-F327, 1998
25. Borkan S C, Wang Y H, Lieberthal W, Burke P R, Schwartz J H: Heat stressameliorates ATP depletion-induced sublethal injury in mouse proximaltubule cells. Am J Physiol 272: F347-F355, 1997
26. Li F, Mao H P, Ruchalski K L, Wang Y H, Choy W, Schwartz J H, et al.: Heatstress prevents mitochondrial injury in ATP-depleted renal epithelialcells. Am J Physiol Cell Physiol 283: C917-C926, 2002
27. Wang Y H, Borkan S C: Prior heat stress enhances survival of renal epithelialcells after ATP depletion. Am J Physiol 270: F1057-F1065,1996
28. Gall J M, Wang Z, Bonegio R G, Havasi A, Liesa M, Vemula P, et al.: Conditional knockout of proximal tubule mitofusin 2 accelerates recoveryand improves survival after renal ischemia. J Am Soc Nephro 126: 1092-1102, 2015
29. Wang Z, Havasi A, Gall J, Bonegio R, Li Z, Mao H, et al.: GSK3betapromotes apoptosis after renal ischemic injury. J Am Soc Nephrol 21:284-294, 2010
30. Moers C, Smits J M, Maathuis M H, Treckmann J, van Gelder F, Napieralski B P, et al.: Machine perfusion or cold storage in deceaseddonorkidney transplantation. N Engl J Med 360: 7-19, 2009
31. Salih E: Phosphoproteomics by mass spectrometry and classical proteinchemistry approaches. Mass Spectrom Rev 24: 828-846, 2005
32. Czernick D, Liu J, Serge D, Salih E: Topographical distribution of phosphorylation sites of phosvitins by mass spectrometry. J Proteomics 83: 76-98, 2013
33. Salih E, Siqueira W L, Helmerhorst E J, Oppenheim F G: Large-scale phosphoproteome of human whole saliva using disulfide-thiol interchange covalent chromatography and mass spectrometry. Anal Biochem 407: 19-33, 2010
34. Kerr L E, Birse-Archbold J L, Short D M, McGregor A L, Heron I, Macdonald D C, et al.: Nucleophosmin is a novel Bax chaperone that regulates apoptotic cell death. Oncogene 26: 2554-2562, 2007
35. Sarko D, Beijer B, Garcia Boy R, Nothelfer E M, Leotta K, Eisenhut M, et al.: The pharmacokinetics of cell-penetrating peptides. Mol Pharm 7: 2224-2231, 2010
36. Gall J M, Wang Z, Liesa M, Molina A, Havasi A, Schwartz J H, et al.: Role of mitofusin 2 in the renal stress response. PLoS One 7: e31074, 2012
37. Gall J M, Wong V, Pimental D R, Havasi A, Wang Z, Pastorino J G, et al.: Hexokinase regulates Bax-mediated mitochondrial membrane injury following ischemic stress. Kidney Int 79: 1207-1216, 2011
38. Wang Z, Havasi A, Gall J M, Mao H, Schwartz J H, Borkan S C: Betacatenin promotes survival of renal epithelial cells by inhibiting Bax. J Am Soc Nephro! 20: 1919-1928, 2009
39. Daugs A, Lehmann N, Eroglu D, Meinke M C, Markhoff A, Bloch O: In vitro detection system to evaluate the immunogenic potential of xenografts. Tissue Eng Part C Methods 24: 280-288, 2018
40. Falini B, Bolli N, Liso A, Martelli M P, Mannucci R, Pileri S, et al.: Altered nucleophosmin transport in acute myeloid leukaemia with mutated NPM1: Molecular basis and clinical implications. Leukemia 23: 1731-1743, 2009
41. Ferrara F, Palmieri S, Leoni F: Clinically useful prognostic factors in acute myeloid leukemia. Crit Rev Oncol Hematol 66: 181-193, 2008 42 Khandelwal N, Simpson J, Taylor G, Rafique S, Whitehouse A, Hiscox J, et al.: Nucleolar NF-kB/RelA mediates apoptosis by causing cytoplasmic relocalization of nucleophosmin. Cell Death Differ 18: 1889-1903, 2011
43. Kellum J A, Lameire N; KDIGO AKI Guideline Work Group: Diagnosis, evaluation, and management of acute kidney injury: A KDIGO summary (Part 1). Crit Care 17: 204, 2013
44. Bacher U, Schnittger S, Haferlach C, Haferlach T: Molecular diagnostics in acute leukemias. Clin Chem Lab Med 47: 1333-1341, 2009
45. Lim M J, Wang X W: Nucleophosmin and human cancer. Cancer Detect Prev 30: 481-490, 2006
46. Marfori M, Mynott A, Ellis J J, Mehdi A M, Saunders N F, Curmi P M, et al.: Molecular basis for specificity of nuclear import and prediction of nuclear localization. Biochim Biophys Acta 1813: 1562-1577, 2011
47. Thompson J, Finlayson K, Salvo-Chirnside E, MacDonald D, McCulloch J, Kerr L, et al.: Characterisation of the Bax-nucleophosmin interaction: The importance of the Bax C-terminus. Apoptosis 13: 394-403, 2008
48. Hsu Y T, Youle R J: Nonionic detergents induce dimerization among members of the Bcl-2 family. J Biol Chem 272: 13829-13834, 1997
49. Peyerl F W, Dai S, Murphy G A, Crawford F, White J, Marrack P, et al.: Elucidation of some Bax conformational changes through crystallization of an antibody-peptide complex. Cell Death Differ 14: 447-452, 2007
50. Knudson A: Alfred Knudson and his two-hit hypothesis. (Interview by Ezzie Hutchinson). Lancet Oncol 2: 642-645, 2001
51. Lindenboim L, Blacher E, Borner C, Stein R: Regulation of stress-induced nuclear protein redistribution: A new function of Bax and Bak uncoupled from Bcl-x(L). Cell Death Differ 17: 346-359, 2010
52. Gardai S J, Hildeman D A, Frankel S K, Whitlock B B, Frasch S C, Borregaard N, et al.: Phosphorylation of Bax Ser184 by Akt regulates its activity and apoptosis in neutrophils. J Biol Chem 279: 21085-21095, 2004
53. Linseman D A, Butts B D, Precht T A, Phelps R A, Le S S, Laessig T A, et al.: Glycogen synthase kinase-3beta phosphorylates Bax and promotes its mitochondrial localization during neuronal apoptosis. J Neurosci 24: 9993-10002, 2004
54. Papadakis E S, Finegan K G, Wang X, Robinson A C, Guo C, Kayahara M, et al.: The regulation of Bax by c-Jun N-terminal protein kinase (JNK) is a prerequisite to the mitochondrial-induced apoptotic pathway. FEBS Lett 580: 1320-1326, 2006
55. Ardito F, Giuliani M, Perrone D, Troiano G, Lo Muzio L: The crucial role of protein phosphorylation in cell signaling and its use as targeted therapy (Review). Int J Mol Med 40: 271-280, 2017
56. Galluzzi L, Kepp O, Krautwald S, Kroemer G, Linkermann A: Molecular mechanisms of regulated necrosis. Semin Cell Dev Biol 35: 24-32, 2014
57. Tischner D, Manzl C, Soratroi C, Villunger A, Krumschnabel G: Necrosis-like death can engage multiple pro-apoptotic Bcl-2 protein family members. Apoptosis 17: 1197-1209, 2012

58. Whelan R S, Konstantinidis K, Wei A C, Chen Y, Reyna D E, Jha S, et al.: Bax regulates primary necrosis through mitochondrial dynamics. Proc Natl Acad Sci USA 109: 6566-6571, 2012
59. Borkan S C: The role of BCL-2 family members in acute kidney injury. Semin Nephrol 36: 237-250, 2016
60. Karch J, Kanisicak O, Brody M J, Sargent M A, Michael D M, Molkentin J D: Necroptosis interfaces with MOMP and the MPTP in mediating cell death. PLoS One 10: e0130520, 2015
61. Havasi A, Lu W, Cohen H T, Beck L, Wang Z, Igwebuike C, et al.: Blocking peptides and molecular mimicry as treatment for kidney disease. Am J Physiol Renal Physiol 312: F1016-F1025, 2017
62. Vegt E, Melis M, Eek A, de Visser M, Brom M, Oyen W J, et al.: Renal uptake of different radiolabelled peptides is mediated by megalin: SPECT and biodistribution studies in megalin-deficient mice. Eur J Nucl Med Mol Imaging 38: 623-632, 2011
63. Bonegio R, Lieberthal W: Role of apoptosis in the pathogenesis of acute renal failure. Curr Opin Nephrol Hypertens 11: 301-308, 2002
64. Ohman E M, Harrington R A, Cannon C P, Agnelli G, Cairns J A, Kennedy J W: Intravenous thrombolysis in acute myocardial infarction. Chest 119 [1 Suppl]: 253S-277S, 2001
65. Lansberg M G, O'Donnell M J, Khatri P, Lang E S, Nguyen-Huynh M N, Schwartz N E, et al.: Antithrombotic and thrombolytic therapy for ischemic stroke: Antithrombotic therapy and prevention of thrombosis, 9th ed: American College of Chest Physicians Evidence-Based Clinical Practice Guidelines. Chest 141: e601S-e636S, 2012
66. Bleicken S, Jeschke G, Stegmueller C, Salvador-Gallego R, Garcia-Sáez A J, Bordignon E: Structural model of active Bax at the membrane. Mol Cell 56: 496-505, 2014
67. Wei Q, Dong G, Chen J K, Ramesh G, Dong Z: Bax and Bak have critical roles in ischemic acute kidney injury in global and proximal tubulespecific knockout mouse models. Kidney Int 84: 138-148, 2013
68. Karch J, Kwong J Q, Burr A R, Sargent M A, Elrod J W, Peixoto P M, et al.: Bax and Bak function as the outer membrane component of the mitochondrial permeability pore in regulating necrotic cell death in mice. eLife 2: e00772, 2013
69. Linkermann A, Brasen J H, Himmerkus N, Liu S, Huber T B, Kunzendorf U, et al.: Rip1 (receptor-interacting protein kinase 1) mediates necroptosis and contributes to renal ischemia/reperfusion injury. Kidney Int 81: 751-761, 2012
70. Zeiss C J: The apoptosis-necrosis continuum: Insights from genetically altered mice. Vet Pathol 40: 481-495, 2003
71. Naga_nska E, Matyja E, Grzywaczewska E: Morphological evidence of the continuum between necrosis and apoptosis in model of anoxia in vitro. J Neurochem 85: 24-24, 2003
72. Rabb H, Griffin M D, McKay D B, Swaminathan S, Pickkers P, Rosner M H, et al.: Acute Dialysis Quality Initiative Consensus XIII Work Group: Inflammation in AKI: Current understanding, key questions, and knowledge gaps. J Am Soc Nephrol 27: 371-379, 2016
73. Brooks C, Cho S G, Wang C Y, Yang T, Dong Z: Fragmented mitochondria are sensitized to Bax insertion and activation during apoptosis. Am J Physiol Cell Physiol 300: C447-C455, 2011
74. Valentijn A J, Upton J P, Bates N, Gilmore A P: Bax targeting to mitochondria occurs via both tail anchor-dependent and -independent mechanisms. Cell Death Differ 15: 1243-1254, 2008
75. Hisaoka M, Ueshima S, Murano K, Nagata K, Okuwaki M: Regulation of nucleolar chromatin by B23/nucleophosmin jointly depends upon its RNA binding activity and transcription factor UBF. Mol Cell Biol 30: 4952-4964, 2010

References for Example 5:
1. Wang, et. al. Molecular Cell Biology; 33; 1916, 2014
2. Wang, et, al. Abstract submitted. June 2017 to the AM Society of Nephrology Annual meeting
1. Kerr, L. E., et al., Nucleophosmin is a novel Bax chaperone that regulates apoptotic cell death. Oncogene, 2007. 26(18): p. 2554-62.
2. Thompson, J., et al., Characterisation of the Bax-nucleophosmin interaction: the importance of the Bax C-terminus. Apoptosis, 2008. 13(3): p. 394-403.
3. Cha, H., et al., Phosphorylation regulates nucleophosmin targeting; to the centrosome during mitosis as detected by cross-reactive phosphorylation-specific MKK1/MKK2 antibodies. Biochem J, 2004. 378(Pt 3): p. 857-65.
4. Chou, C. C. and B. Y. Yung. Increased stability of nucleophosinin/B23 in anti-apoptotic effect of ras during serum deprivation. Mol Pharmacol, 2001. 59(1): p. 38-45.
5. Falini, B., et al., Altered nucleophosmin transport in acute myeloid leukaemia with mutated NPM1: molecular basis and clinical implications. Leukemia, 2009. 23(10): p. 1731-43.
6. Falini, B., et al., Immunohistochemistry predicts nucleophosmin (NPM) mutations in acute myeloid leukemia. Blood, 2006. 108(6): p. 1999-2005.
7. Falini., B., et al. Cytoplasmic nucleophosmin in acute myelogenous leukemia with a normal karyotype. N Engl J Med, 2005. 352(3): p. 254-66.
8. Ferrara, F., S. Palmieri, and F. Leoni, Clinically useful prognostic factors in acute myeloid leukemia. Crit Rev Oncol Hematol, 2008. 66(3): p. 181-93.
9. Lindenboim, L., et at, Regulation of stress-induced nuclear protein redistribution: a new function of Bax and Bak uncoupled from Bcl-x(L). Cell Death Differ, 2010. 17(2): p. 346-59.
10. Okuwaki, M., The structure and functions of NPM1/Nucleophsmin/B23, a multifunctional nucleolar acidic protein, J Biochem, 2008. 143(4): p. 441-8.

The invention claimed is:

1. A method of treating a subject with kidney injury, ischemia, or a subject after an ischemic injury, the method comprising administering to a subject a composition comprising at least one NPM inhibitor peptide selected from the group consisting of the amino acid sequences of:
   a. TLKMSVQPTVSLGGFEITPPVVLRLK (SEQ ID NO: 2),
   b. ESFKKQEKTPKTPKGPSSVEDIKAK (SEQ ID NO: 3),
   c. a peptide having 95% sequence identity to SEQ ID NO: 2 and having at least 85% of the activity to inhibit Bax-NMP complex formation as compared to SEQ ID NO: 2,
   d. a peptide having 95% sequence identity to SEQ ID NO: 3 and having at least 85% of the activity to inhibit Bax-NMP complex formation as compared to SEQ ID NO: 3, or
   e. a peptide of any of (i)-(iv) fused to a renal nuclear localization signal (NSL).

2. The method of claim 1, wherein the peptide is administered within about 48 hours of an ischemic event or ischemic injury.

3. The method of claim 1, wherein the kidney injury is selected from the group consisting of: injury to the proximal tubule of the kidney; acute kidney injury (AKI); chronic kidney disease (CKD); early kidney injury which will progress into chronic kidney disease (CKD).

4. The method of claim 1, wherein the subject is a human.

5. The method of claim 1, wherein the NPM inhibitor peptide is fused to a renal targeting nuclear localization sequence (NSL).

6. A method of treating a subject with kidney injury, ischemia, or a subject after an ischemic injury, the method comprising administering to a subject a composition comprising at least one NPM inhibitor peptide selected from the group consisting of the amino acid sequences of:
   a. TLKMSVQPTVSLGGFEITPPVVLRLK (SEQ ID NO: 2),
   b. ESFKKQEKTPKTPKGPSSVEDIKAK (SEQ ID NO: 3),
   c. a peptide having 95% sequence identity to SEQ ID NO: 2,
   d. a peptide having 95% sequence identity to SEQ ID NO: 3, and
   e. a peptide of any of (i)-(iv) fused to a renal nuclear localization signal (NSL).

7. A method of treating a subject with kidney injury comprising administering to a subject a composition comprising at least one NPM inhibitor peptide selected from the group consisting of:
   SEQ ID NO: 2 and
   SEQ ID NO: 2 or 3 fused to a renal targeting nuclear localization sequence (NLS).

8. The method of claim 7, wherein the NPM inhibitor peptide is administered within about 48 hours of an ischemic event or ischemic injury.

9. The method of claim 7, wherein the kidney injury is selected from the group consisting of injury to the proximal tubule of the kidney; acute kidney injury (AK1); chronic kidney disease (CKD); and early kidney injury which will progress into chronic kidney disease (CKD).

10. The method of claim 7, wherein the subject is a human.

11. The method of claim 7, wherein the NPM inhibitor peptide is fused to a renal targeting nuclear localization sequence (NSL).

* * * * *